United States Patent
Massey et al.

(10) Patent No.: US 6,916,606 B2
(45) Date of Patent: Jul. 12, 2005

(54) ELECTROCHEMILUMINESCENT ASSAYS

(75) Inventors: Richard J. Massey, Rockville, MD (US); Michael J. Powell, Gaithersburg, MD (US); Paul A. Mied, New Windsor, MD (US); Peter Feng, Rockville, MD (US); Leopoldo Della Ciana, Rockville, MD (US); Walter J. Dressick, Rockville, MD (US); Mohindar S. Poonian, Gaithersburg, MD (US)

(73) Assignee: BioVeris Corporation, Gaithersburg, MD (US)

( * ) Notice: Subject to any disclaimer, the term of this patent is extended or adjusted under 35 U.S.C. 154(b) by 0 days.

(21) Appl. No.: 10/274,079

(22) Filed: Oct. 18, 2002

(65) Prior Publication Data
US 2005/0106652 A1 May 19, 2005

Related U.S. Application Data

(60) Division of application No. 08/415,756, filed on Apr. 3, 1995, now abandoned, which is a continuation of application No. 08/195,825, filed on Feb. 10, 1994, now abandoned, which is a continuation of application No. 07/369,560, filed on Dec. 18, 1987, now abandoned, which is a continuation-in-part of application No. 06/858,354, filed on Apr. 30, 1986, now abandoned.

(51) Int. Cl.$^7$ .......................... C12Q 1/70; C12Q 1/68; G01N 33/53; G01N 33/566; A61K 38/00

(52) U.S. Cl. .................. 435/5; 435/6; 435/7.1; 435/7.2; 530/300; 530/350; 530/387.2; 546/2; 436/501

(58) Field of Search .................... 435/5, 6, 7.1, 7.2; 530/300, 350, 387.2; 546/2; 436/501

(56) References Cited

U.S. PATENT DOCUMENTS 5,221,605 A * 6/1993 Bard et al. .................... 435/4

* cited by examiner

*Primary Examiner*—Jezia Riley
(74) *Attorney, Agent, or Firm*—Finnegan, Henderson, Farabow, Garrett & Dunner L.L.P.

(57) ABSTRACT

Qualitative and quantitative electrochemiluminescent assays for analytes of interest present in multicomponent liquids are provided. These methods comprise contacting a sample with a reagent labeled with an electrochemiluminescent chemical moiety and capable of combining with the analyte of interest, exposing the resulting sample to electrochemical energy and detecting electromagnetic radiation emitted by the electrochemiluminescent chemical moiety.

Further provided are methods for detecting and identifying the presence of a multiplicity of analytes in a liquid food or food homogenate. These methods comprise immersing a diagnostic reagent holder, provided with a multiplicity of reagents, into the food or food homogenate, removing the diagnostic reagent holder from the liquid food or food homogenate, and detecting and identifying the presence of a multiplicity of analytes of interest bound to the diagnostic reagent holder, thereby detecting and identifying the presence of a multiplicity of analytes of interest in the food or food homogenate.

The invention further provides an enzyme immunoassay for coliform bacteria. This assay comprises inoculating a sample into a suitable medium for coliform reproduction, immobilizing coliforms present in the medium to a suitable surface, treating the surface with an antibody directed to the immobilized coliforms and detecting the presence of the immobilized coliforms immobilized to a suitable surface.

2 Claims, 13 Drawing Sheets

ELECTROCHEMILUMINESCENT ASSAYS

This application is a divisional of application Ser. No. 08/415,756, filed Apr. 3, 1995, now abandoned, which is a continuation of application Ser. No. 08/195,825, filed Feb. 10, 1994, now abandoned, which is continuation of application Ser. No. 07/369,560, filed Dec. 8, 1987, now abandoned, which is a continuation-in-part of application Ser. No. 06/858,354, filed Apr. 30, 1986, now abandoned. Each of these predecessor applications is incorporated herein by reference.

BACKGROUND OF THE INVENTION

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

There is a continuous and expanding need for rapid, highly specific methods of detecting and quantifying chemical, biochemical, and biological substances. Of particular value are methods for measuring small quantities of pharmaceuticals, metabolites, microorganisms and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the complexing materials.

The specific labeling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, and preferably never, found in nature. The label should be stable and detectable in aqueous systems over periods of time ranging up to months. Detection of the label should be rapid, sensitive, and reproducible without the need for expensive, specialized facilities or personnel. Quantification of the label should be relatively independent of variables such as temperature and the composition of the mixture to be assayed. Most advantageous are labels which can be used in homogeneous systems, i.e., systems in which separation of the complexed and uncomplexed labeled material is not necessary. This is possible if the detectability of the label is modulated when the labeled material is incorporated into a specific complex.

A wide variety of labels have been developed, each with particular advantages and disadvantages. For example, radioactive labels are quite versatile, and can be detected at very low concentrations. However, they are expensive, hazardous, and their use requires sophisticated equipment and trained personnel. Furthermore, the sensitivity of radioactive labels is limited by the fact that the detectable event can, in its essential nature, occur only once per radioactive atom in the labeled material. Moreover, radioactive labels cannot be used in homogeneous methods.

Thus, there is wide interest in non-radioactive labels. These include molecules observable by spectrophotometric, spin resonance, and luminescence techniques, as well as enzymes which produce such molecules. Among the useful non-radioactive labeling materials are organometallic compounds. Because of the rarity of some metals in biological systems, methods which specifically assay the metal component of the organometallic compounds can be successfully exploited. For example, Cais, U.S. Pat. No. 4,205,952 (1980) discloses the use of immunochemically active materials labeled with certain organometallic compounds for use in quantitating specific antigens. Any general method of detecting the chosen metals can be used with these labels, including emission, absorption and fluorescence spectroscopy, atomic absorption, and neutron activation. These methods often suffer from lack of sensitivity, can seldom be adapted to a homogeneous system, and as with atomic absorption, sometimes entail destruction of the sample.

Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of the luminescent species by a chemical transfer of energy. "Electrochemiluminescence" entails the creation of the luminescent species electrochemically.

These luminescent systems are of increasing importance. For example, Mandle, U.S. Pat. No. 4,372,745 (1983) discloses the use of chemiluminescent labels in immunochemical applications. In the disclosed systems, the labels are excited into a luminescent state by chemical means such as by reaction of the label with $H_2O_2$ and an oxalate. In these systems, $H_2O_2$ oxidatively converts the oxalate into a high energy derivative, which then excites the label. This system will, in principle, work with any luminescent material that is stable in the oxidizing conditions of the assay and can be excited by the high energy oxalate derivative. Unfortunately, this very versatility is the source of a major limitation of the technique: typical biological fluids containing the analyte of interest also contain a large number of potentially luminescent substances that can cause high background levels of luminescence.

Another example of the immunochemical use of chemiluminescence which suffers from the same disadvantages is Oberhardt et al., U.S. Pat. No. 4,280,815, (1981) who disclose the in situ electrochemical generation of an oxidant (e.g., $H_2O_2$) in close proximity to an immunoreactant labeled with a chemiluminescent species. The electrogenerated oxidant diffuses to the chemiluminescent species and chemically oxidizes it, resulting in the net transfer of one or more electrons to the electrogenerated oxidant. Upon oxidation, the chemiluminescent species emits a photon. In contrast, the subject invention requires the direct transfer of electrons from a source of electrochemical energy to a chemiluminescent species which is capable of repeatedly emitting photons.

The present invention is concerned with electrochemiluminescent labels. Suitable labels comprise electrochemiluminescent compounds, including organic compounds and organometallic compounds. Electrochemiluminescent methods of determining the presence of labeled materials are preferred over other methods for many reasons. They are highly diagnostic of the presence of a particular label, sensitive, nonhazardous, inexpensive, and can be used in a wide variety of applications. Organic compounds which are suitable electrochemical labels include, for example, rubrene and 9,10-diphenyl anthracene. Many organometallic compounds are suitable electrochemical labels, but of particular use are Ru-containing and Os-containing compounds.

Thus, in one embodiment, the present invention is concerned with the use of Ru-containing and Os-containing labels which can be detected by a wide variety of methods. These labels are advantageous for many reasons that will be discussed herein.

Ru-containing and Os-containing organometallic compounds have been discussed in the literature. Cais discloses that any metal element or combination of metal elements, including noble metals from group VIII such as Ru, would be suitable components of organmetallic labels detectable by atomic absorption methods. (Cais, column 11, line 20). However, ruthenium is not a preferred metal in Cais, osmium is not specifically mentioned, no data are presented on the efficiency of using Ru or Os in any of the methods disclosed, and the preferred method of detection, atomic absorption, entails destruction of the sample.

Weber, U.S. Pat. No. 4,293,310 (1981), discloses the use of Ru-containing and Os-containing complexes as electrochemical labels for analytes in immunoassays. The disclosed complexes are linked to amino groups on the analytes through a thiourea linkage. Weber also suggests the possibility of forming carboxylate esters between the labels and hydroxy groups on other analytes.

According to Weber, the presence of the labeled materials can be determined with an apparatus and method which comprises a quencher and an electrochemical flow cell with light means. The photoelectrochemically active label upon photoexcitation transfers an electron to a quencher molecule; the oxidized molecule is subsequently reduced with an electron from an electrode of the flow cell which is held at suitable potential. This electron is measured as photocurrent. The amount of free labelled analyte in the system is determined by the photocurrent signal. Note that this method is the reverse of electrochemiluminescent detection of luminescent materials.

In subsequent reports, Weber et al. discussed the problems associated with the use of this method to detect Ru-containing labels (1). In Table 2 of Weber et al. (1), the extrapolated detection limit for tris(bipyridyl)ruthenium(II) is $1.1 \times 10^{-10}$ moles/L under optimal conditions. In anticipating that the actual use of these labels would entail measurements in the presence of complex mixtures, Weber et al. tested for potential interferents in their system. Table 3 of Weber et al. lists dimethylalkyl amines, EDTA, N-methylmorpholine, N,N'-dimethylpiperazine, hydroxide, oxalate, ascorbate, uric acid, and serum as interferents which would presumably raise the practical detection limit substantially above $1.1 \times 10^{-10}$ moles/L.

These studies were performed with a simple Ru-containing compound. No studies were reported in Weber or Weber et al. regarding the limits of detection of complex substances labelled with Ru-containing labels, or whether the thiourea linkage between the labeled material and label is stable under conditions of the assay.

The particular labels with which the present invention is concerned are electrochemiluminescent. They can often be excited to a luminescent state without their oxidation or reduction by exposing the compounds to electromagnetic radiation or to a chemical energy source such as that created by typical oxalate-$H_2O_2$ systems. In addition, luminescence of these compounds can be induced by electrochemical methods which do entail their oxidation and reduction.

Extensive work has been reported on methods for detecting $Ru(2,2'$-bipyridine$)_3^{2+}$ using photoluminescent, chemiluminescent, and electrochemiluminescent means (2,3). This work demonstrates that bright orange chemiluminescence can be based on the aqueous reaction of chemically generated or electrogenerated $Ru(bpy)_3^{3+}$ (where "bpy" represents a bipyridyl ligand) with strong reductants produced as intermediates in the oxidation of oxalate ions of other organic acids. Luminescence also can be achieved in organic solvent-$H_2O$ solutions by the reaction of electrogenerated, or chemically generated, $Ru(bpy)_3^{1+}$ with strong oxidants generated during reduction of peroxydisulfate. A third mechanism for production of electrochemiluminescence from $Ru(bpy)_3^{2+}$ involves the oscillation of an electrode potential between a potential sufficiently negative to produce $Ru(bpy)_3^{1+}$ and sufficiently positive to produce $Ru(bpy)_3^{3+}$. These three methods are called, respectively, "oxidative-reduction," "reductive-oxidation," and "the $Ru(bpy)_3^{3+/+}$ regenerative system".

The oxidative-reduction method can be performed in water, and produces an intense, efficient, stable luminescence, which is relatively insensitive to the presence of oxygen or impurities. This luminescence from $Ru(bpy)_3^{2+}$ depends upon the presence of oxalate or other organic acids such as pyruvate, lactate, malonate, tartrate and citrate, and means of oxidatively producing $Ru(bpy)_3^{3+}$ species. This oxidation can be performed chemically by such strong oxidants as $PbO_2$ or a Ce(IV) salt. It can be performed electrochemically by a sufficiently positive potential applied either continuously or intermittently. Suitable electrodes for the electrochemical oxidation of $Ru(bpy)_3^{2+}$ are, for example, Pt, pyrolytic graphite, and glassy carbon. Although the oxalate or other organic acid is consumed during chemiluminescence, a strong, constant chemiluminescence for many hours can be achieved by the presence of an excess of the consumed material, or by a continuous supply of the consumed material to the reaction chamber.

The reductive-oxidation method can be performed in partially aqueous solutions containing an organic co-solvent such as, for example, acetonitrile. This luminescence depends upon the presence of peroxydisulfate and a means of reductively producing $Ru(bpy)_3^{1+}$ species. The reduction can be performed chemically by strong reductants such as, for example, magnesium or other metals. It can be performed electrochemically by a sufficiently negative potential applied either continuously or intermittently. A suitable electrode for the electrochemical reduction of $Ru(bpy)_3^{2+}$ is, for example, a polished glassy-carbon electrode. As with the oxidative-reduction method, continuous, intense luminescence can by achieved for many hours by inclusion of excess reagents, or be continuous addition of the consumed reagents to the reaction mixture.

The $Ru(bpy)_3^{3+/+}$ regenerative system can be performed in organic solvents such as acetonitrile or in partially aqueous systems, by pulsing an electrode potential between a potential sufficiently negative to reduce $Ru(bpy)_3^{2+}$ and a potential sufficiently positive to oxidize $Ru(bpy)_3^{2+}$. A suitable electrode for such a regenerative system is, for example, a Pt electrode. This system does not consume chemical reagents and can proceed, in principle, for an unlimited duration.

These three methods of producing luminescent Ru-containing compounds have in common the repetitive oxidation-reduction or reduction-oxidation of the Ru-containing compound. The luminescence of solutions containing these compounds is therefore highly dependent on the electric potential of the applied energy source, and is therefore highly diagnostic of the presence of the Ru-containing compound.

Mandle cites Curtis et al. (4) as a possible label in chemiluminescent applications. Curtis et al. reports only unpublished observations that Ru complexes can be induced to emit light when chemically excited by an oxalate/$H_2O_2$ system (Curtis et al. p. 350).

Neither Mandle nor Curtis recognized the exceptional utility of ruthenium and osmium complexes in chemiluminescent applications or the utility of electrochemiluminescent systems. Sprintschnik, G. et al. (5) have described complexes of tris (2,2'-bipyridine)ruthenium(II) esterified with octadecanol or dehydrocholesterol, and have created monolayer films of these surfactant complexes. The complexes were photoluminescent. But when the films were exposed to water, and then to light, the Ru-complexes failed to photoluminesce. This was attributed to photohydrolysis of ester groups in the presence of light.

It has been discovered, and is disclosed herein, that a wide variety of analytes of interest and chemical moieties that bind to analytes of interest may be conveniently attached to Ru-containing or Os-containing labels through amide or amine linkages. The labeled materials may then be determined by any of a wide variety of means, but by far the most efficient, reliable, and sensitive means are photoluminescent, chemiluminescent, and electrochemiluminescent means. It is also disclosed herein that electrochemiluminescent labels, including Ru-containing and Os-containing labels and organic molecules such as rubrene and 9,10-diphenyl anthracene, are particularly versatile and advantageous. The great advantages of the use of these novel labeled materials, and of the methods of detecting them, are further discussed hereinbelow.

For many years the food industry has been concerned with the presence of biological and chemical contaminants in raw food components and processed foods. While technological advances have been made in reducing the occurrence of food contamination and food borne disease outbreaks resulting therefrom, little progress has been reported in developing rapid and sensitive methods for the detection and identification of food contaminants. Existing standard methods for the detection of harmful contaminants in foods are generally very time consuming, labor intensive, and technically difficult. While the analytical methods themselves for the most part are of adequate sensitivity, the lengthy sample preparation procedures prior to the performance of the detection method often result in low yield of the contaminant in question so that false negatives are frequently encountered.

Two examples which serve to illustrate these problems are the currently recognized standard methods for detecting the presence of *Salmonella* and *Staphylococcal* enterotoxins in foods. The detection of *Salmonella* in foods involves several enrichment stages due to the fact that these bacteria, when present in foods, are usually found in low numbers and are often sublethally injured. Therefore, detection methods for *Salmonella* must be sensitive and allow for the resuscitation and growth of injured cells.

Two methods for *Salmonella* detection are currently recommended by the U.S. Food and Drug Administration. These methods appear in The Bacteriological Analytical Manual for Foods (1984), 6th ed., Association of Official Analytical Chemists, Washington, D.C. One method is a pure culture technique involving preenrichment, selective enrichment and selective plating, a procedure which requires 4 days to obtain presumptive results and 5 to 7 days to obtain complete results. The other method involves immunofluorescence after selective enrichment. This procedure is more rapid, however it can result in a high incidence of false-positive results due to problems of cross-reactivity of the polyvalent antisera used in the test (6, 7).

The procedure recommended by the U.S. Food and Drug Administration for the detection of *Staphylococcal* enterotoxitis in foods also appears in The Bacteriological Analytical Manual for Foods (1984), 6th ed. Association of Official Analytical Chemists, Washington, D.C. This method involves the concentration of an extract of a large food sample, e.g. approximately 100 grams, to a small volume, e.g. approximately 0.2 ml, by several dialysis concentration steps and an ion exchange column purification of the sample extract in order to prepare the sample for the microslide double-immunodiffusion technique. This procedure generally requires more than a week to perform.

Tests which are more rapid have recently been developed for the detection of a variety of contaminants such as bacteria, toxins, antibiotics and pesticide residues in foods. In many cases however, sample preparation prior to running the assay continues to be laborious and time consuming. Radioimmunoassays (RIA) and enzyme-linked immunosorbent assays (ELISA) have shortened the hands-on time for the analytical method itself, however these methods are still labor intensive and far from simple to perform. In addition, these methods are usually based on the use of polyclonal antisera, which is variable in specificity and sensitivity, and is generally in short supply for testing for a given food contaminant. ELISA methods have been developed for the analysis of food samples which employ monoclonal antibodies rather than polyclonal antisera. The use of monoclonal antibodies in an assay system for a food contaminant assures the constant supply of a reagent which imparts unchanging specificity and sensitivity to the test itself. Monoclonal antibodies have been used in ELISA systems to test for food contaminants such as *Salmonella* (8) and *Staphylococcal* enterotoxins (9). Commercially available products for *Salmonella* detection which employ EIA methodology (Bio-Enzabead Screen Kit, Litton Bionetics) and DNA probe technology (Gene-Trak, Integrated Genetics) are time consuming and labor intensive. Commercially available tests for detection of *Staphylococcal* enterotoxin in foods which employ reversed passive latex agglutination (SET-RPLA, Denka Seiken Co.) and EIA methodology (SET-EIA, Dr. W. Bommeli Laboratories) suffer from the same limitations.

For the past 100 years the bacterium *Escherichia coli* and the coliform group have been commonly used as indicators to monitor water quality and incidences of sewage contamination.

Current detection methodologies for *E. coli* and/or coliforms are based on the properties of acid or gas production from the fermentation of lactose. The most widely used methods are: the Most Probable Number (MPN) assay and the Membrane Filtration (MF) test. Both techniques are approved by the Environmental Protection Agency (EPA) and the American Public Health Association (APHA) for the microbiological examination of water and waste water (10), and also by the Food and Drug Administration (FDA) for the bacteriological examination of milk and foods (11).

The MPN method is actually comprised of three (12) separate assays (10). In the Presumptive test, a nonselective medium such as Lauryl Sulfate Tryptose (LST) broth or Lactose broth is used to check for gas production from the fermentation of lactose. Gas positive tubes are then subcultured into a more selective medium, Brilliant Green Lactose Bile (BGLB) broth for coliforms and E. coli (EC) broth for fecal coliforms, and again checked for gas production (confirmed test). Samples from positive Confirmatory tests are required to be tested further by plating on a selective and differential medium like Eosin Methylene Blue (EMB) agar or Endos agar, followed by Gram stain and some biochemical tests to firmly establish the presence of the indicator bacteria (Completed test). The entire MPN assay may require up to five (5) days for completion; therefore, for routine water analysis, most laboratories use only the Presumptive and the Confirmed portions of the MPN assay, which still requires 48 hours to 72 hours to complete. In addition to being time consuming and cost ineffective in terms of materials, incidences of both false positive and false negative reactions have also been commonly encountered in the MPN assays (15, 16, 20).

The MF technique for the bacteriological examination of water was introduced in the early 1950's (12). Unlike the MPN assay, which was tedious and time consuming, MF analysis could be completed in 24 hours without the need for further confirmations. The basic MF procedure is as follows: A volume of water sample, usually 100 ml is filtered through a 0.45 um pore diameter filter, and then incubated on a sterile pad saturated with selective medium. The two media most often used are the mEndo broth, selective for coliforms at 35° C., and the mFC broth, selective for fecal coliforms at 44.5° C. (10). Since the introduction of the media, numerous authors have reported that both the mEndo and the mFC broths tend to underestimate the actual numbers of indicator bacteria present, due either to the selectivity of the medium or the high temperature used for incubation (44.5° C.) (21, 22). Such incidences of false negatives have been especially prevalent when the organisms in the sample have been sublethally injured by environmental factors and/or chemicals (17, 18). Recently, modifications have been proposed by the EPA to follow up the MF test by a confirmatory procedure, whereby at least ten colonies on each filter need to be checked for gas production using the LST broth followed by BGLB broth as in the MPN assay (14). Such modifications although would reduce the incidences of both false negative and false positive reactions, it would also increase material cost as well as triple the MF assay time from 24 hours to 72 hours.

In 1982, Feng and Hartman introduced a fluorogenic assay for the detection of E. coli using the substrate 4-methyl umbelliferone glucuronide (MUG) (13). E. coli cells produced the enzyme beta-glucuronidase which would cleave the substrate releasing the fluorogenic 4-methylumbelliferone radical (19). By incorporating the compound MUG into the Presumptive LST medium, a single tube of LST-MUG medium provided both the Presumptive data (gas production) and the Confirmed data (fluorescence) for fecal coliforms within 24 hours. Although the MUG assay was rapid and simple, only 85% to 95% of the E. coli (depending on source) produced this enzyme, hence the test was not 100% reliable. Also the system was not applicable to the coliform group.

Currently, no suitable assay exists for the detection and enumeration of coliforms and fecal coliforms in a sample. The development of a simple, rapid, and reliable detection assay would not only decrease cost and time, but also greatly increase the efficency of monitoring water sanitation and food processing and handling.

SUMMARY OF THE INVENTION

The present invention provides a method of detecting in a predetermined volume of a multicomponent, liquid sample an analyte of interest present in the sample at a concentration below about $10^{-3}$ molar which comprises: a) contacting a sample with a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and the reagent combine; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation, and c) detecting electromagnetic radiation so emitted and thereby detecting the presence of the analyte of interest in the sample.

The present invention also provides a competitive method for detecting in a predetermined volume of a multicomponent, liquid sample an analyte of interest present in the sample at a concentration below about $10^{-3}$ molar which comprises: a) contacting the sample with a reagent (i) capable of being induced to repeatedly emit electromagnetic radiation upon exposure to an amount of electrochemical energy from a suitable source effective to induce the reagent to repeatedly emit radiation and (ii) capable of competing with the analyte of interest for binding sites on a complementary material not normally present in the sample, and with the complementary material, the contact being effected under appropriate conditions such that the analyte of interest and the reagent competitively bind to the complementary material; b) exposing the resulting sample to an amount of electrochemical energy from a suitable source effected to induce the reagent to repeatedly emit radiation, the exposure being effective under suitable conditions so as to induce the reagent to repeatedly emit electromagnetic radiation; and c) detecting electromagnetic radiation so emitted and thereby detecting the presence of the analyte of interest in the sample.

Additionally provided is a method for quantitatively determining in a predetermined volume of a multicomponent, liquid sample, the amount of an analyte of interest present in the sample which comprises: a) contacting the sample with a known amount of a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and reagent combine; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and c) quantitatively determining the amount of radiation so emitted and thereby quantitatively determining the amount of the analyte of interest present in the sample.

The invention further provides a competitive method for quantitatively determining in a predetermined volume of a multicomponent, liquid sample the amount of an analyte of interest present in the sample. This method comprises: a) contacting the sample with a known amount of a reagent (i) capable of being induced to repeatedly emit electromagnetic radiation upon exposure to an amount of electrochemical energy from a suitable source effective to induce the reagent to repeatedly emit radiation and (ii) capable of competing with the analyte of interest for binding sites on a complementary material not normally present in the sample, and with a known amount of the complementary material, the contact being effected under appropriate conditions such that the analyte of interest and the reagent competitively bind to the complementary material; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and c) quantitatively determining the amount of radiation so emitted and thereby quantitatively determining the amount of the analyte of interest present in the sample.

Also provided is a method for detecting and identifying the presence of a multiplicity of analytes of interest in a liquid food or food homogenate. This method comprises: a) immersing into the liquid food or food homogenate a portion of a diagnostic reagent holder suitable for immersing into a liquid or solid suspension and having immobilized to it a multiplicity of reagents, each reagent being immobilized to the diagnostic reagent holder in distinct, identifiable regions and capable of forming a complex with a single analyte of interest so as to allow the formation of immobilized reagent-analyte of interest complexes; b) removing the diagnostic reagent holder from the liquid food or food homogenate; c) rinsing the diagnostic reagent holder with a suitable rinsing solution; d) immersing the portion of the diagnostic reagent holder which contains the immobilized reagent-analyte of interest complexes into a detection solution which contains at least one detection reagent capable of forming complexes with the immobilized reagent-analyte of interest complexes so as to allow the formation of immobilized reagent-analyte of interest detection reagent complexes; and e) detecting the presence on the identifiable regions of the diagnostic reagent holder to which reagents are immobilized of immobilized reagent-analyte of interest-detection reagent complexes, thereby detecting and identifying the presence of a multiplicity of analytes of interest in the liquid food or food homogenate.

The present invention also provides a kit useful for detecting and identifying the presence of a multiplicity of enterotoxins in a sample. This kit comprises: a) a diagnostic reagent holder provided with a handle connected to a surface area suitable for immersing into a liquid or solid suspension, said surface area having at least one nitrocellulose membrane attached to it, said nitrocellulose membrane having a multiplicity of monoclonal antibodies separately and distinctly immobilized to identifiable regions on it each immobilized monoclonal antibody being specific for an antigenic determinant on one enterotoxin; b) a first rinsing solution which comprises a buffered-aqueous solution containing a surfactant; c) a detection which comprises at least one monoclonal antibody enzyme conjugate, the monoclonal antibody of which is specific for antigenic determinants different from but located on each enterotoxin for which the monoclonal antibodies immobilize to the nitrocellulose membrane attached to the diagnostic reagent holder are specific; d) a second rinsing solution which comprises a buffered-aqueous solution; e) an enzyme substrate capable of reacting with the enzyme conjugated to the detection solution monoclonal antibody; and f) a colorless dye.

A method for detecting the presence of at least one species of bacteria in a sample is also provided by the present invention. This method comprises: a) innoculating the sample into at least one receptacle which is provided with an open end and which contains a suitable medium for supporting the growth of the species of bacteria; b) coupling a cap to the end of the receptacle, the face of the cap which when coupled to the receptacle, is exposed to the interior of the receptacle being provided with a surface suitable for immobilizing at least a component of the bacteria; c) incubating the innoculated media under conditions so as to allow bacteria innoculated into the media to reproduce; d) turning each receptacle upside-down for a suitable length of time so as to allow components of the bacterium present in the medium to become immobilized to the surface of the cap which is exposed to the interior of the receptacle; e) turning the upside-down receptacle rightside-up; f) uncoupling the cap from the receptacle; g) contacting the surface of the cap which has components of the bacteria immobilized to it with a reagent capable of forming a complex with the immobilized components of the bacteria under conditions so as to allow the formation of immobilized bacterial component-reagent complexes; and h) detecting immobilized bacterial component-reagent complexes, thereby detecting the presence of the species of bacteria within the sample.

A method for detecting the presence of coliform bacteria in a sample is further provided by the invention. This method comprises: a) innoculating the sample into at least one receptacle which has an open end and contains a non-selective lactose medium and an inverted Durham; b) coupling a cap provided with a polystyrene insert to the open end of each receptacle; c) incubating the inoculated medium for at least 2 hours at 37° C.; d) determining whether each receptacle has gas produced by bacterial fermentation trapped within the inverted Durham vial; e) turning receptacles which have gas trapped within the inverted Durham vial upside-down for a suitable length of time so as to coliform bacteria present in the medium to form coliform-polystyrene complexes; f) turning the upside-down receptacles rightside-up; g) uncoupling the caps from the receptacles; h) treating the polystyrene inserts of the uncoupled caps with a substance suitable for blocking unbound sites; i) treating the polystyrene insert of the caps which had been treated with a substance suitable for blocking unbound sites with at least one anti-coliform bacteria antibody labeled with a detectable marker and capable of binding to coliform bacteria under conditions so as to allow the formation of antibody-coliform-polystyrene complexes; and j) detecting the presence of antibody-coliform-polystyrene complexes on the polystyrene insert, thereby detecting the presence of coliform bacteria in the sample.

●=Normal sera

■=Hemolyzed sera

◆=Lipemic sera

□=Icteric sera

Figure 4:
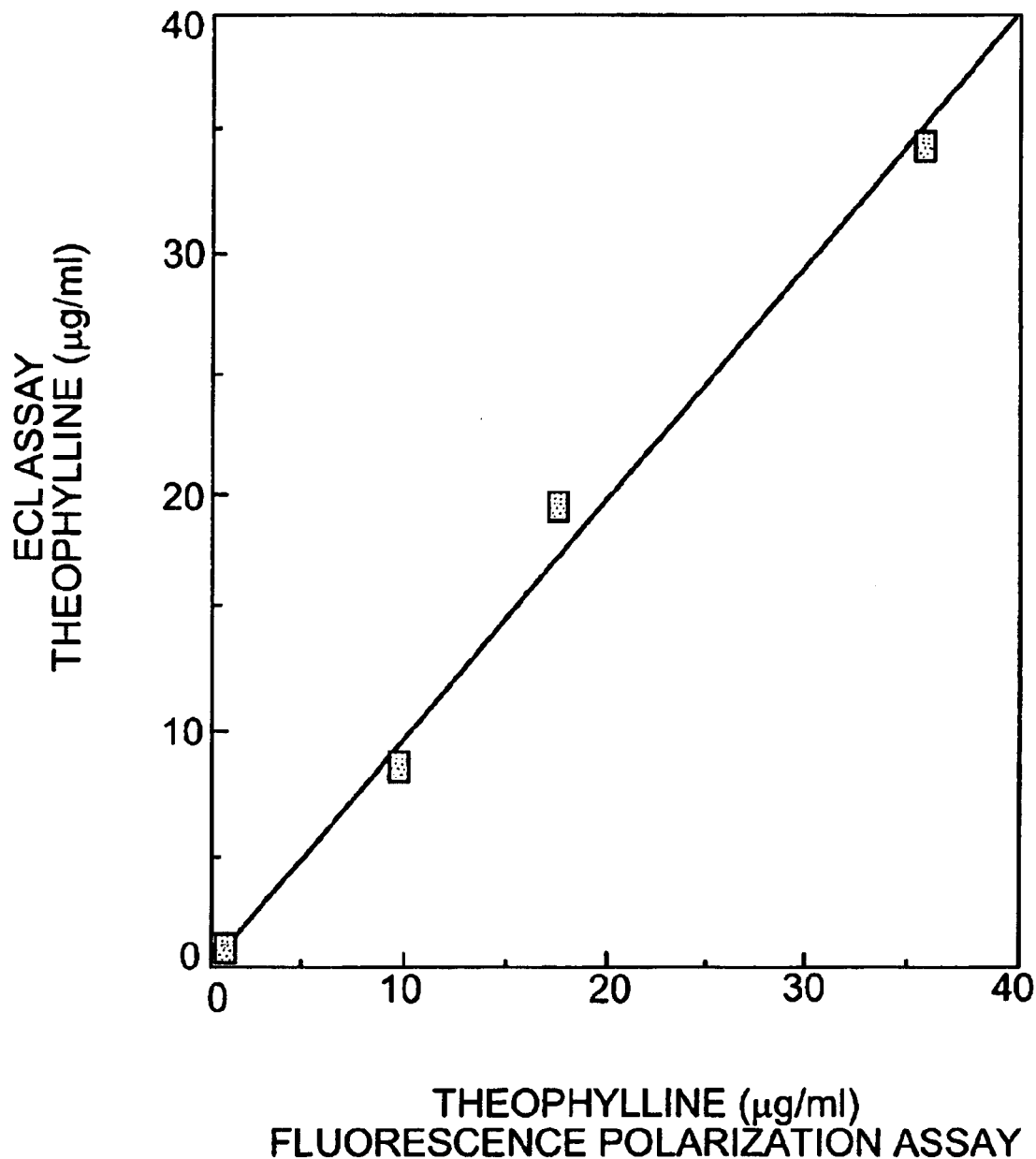
Figure 4B:
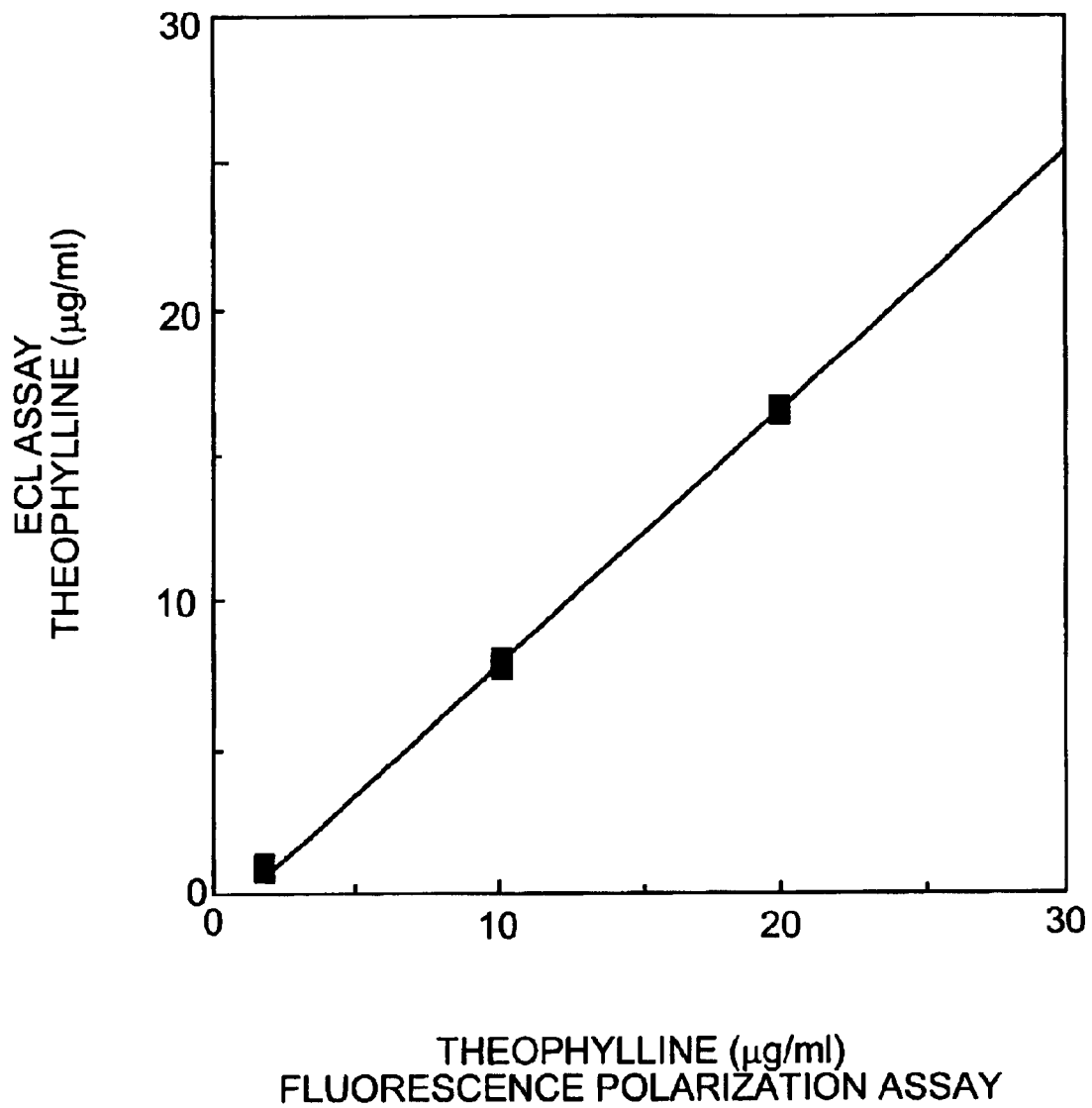
Figure 4C:
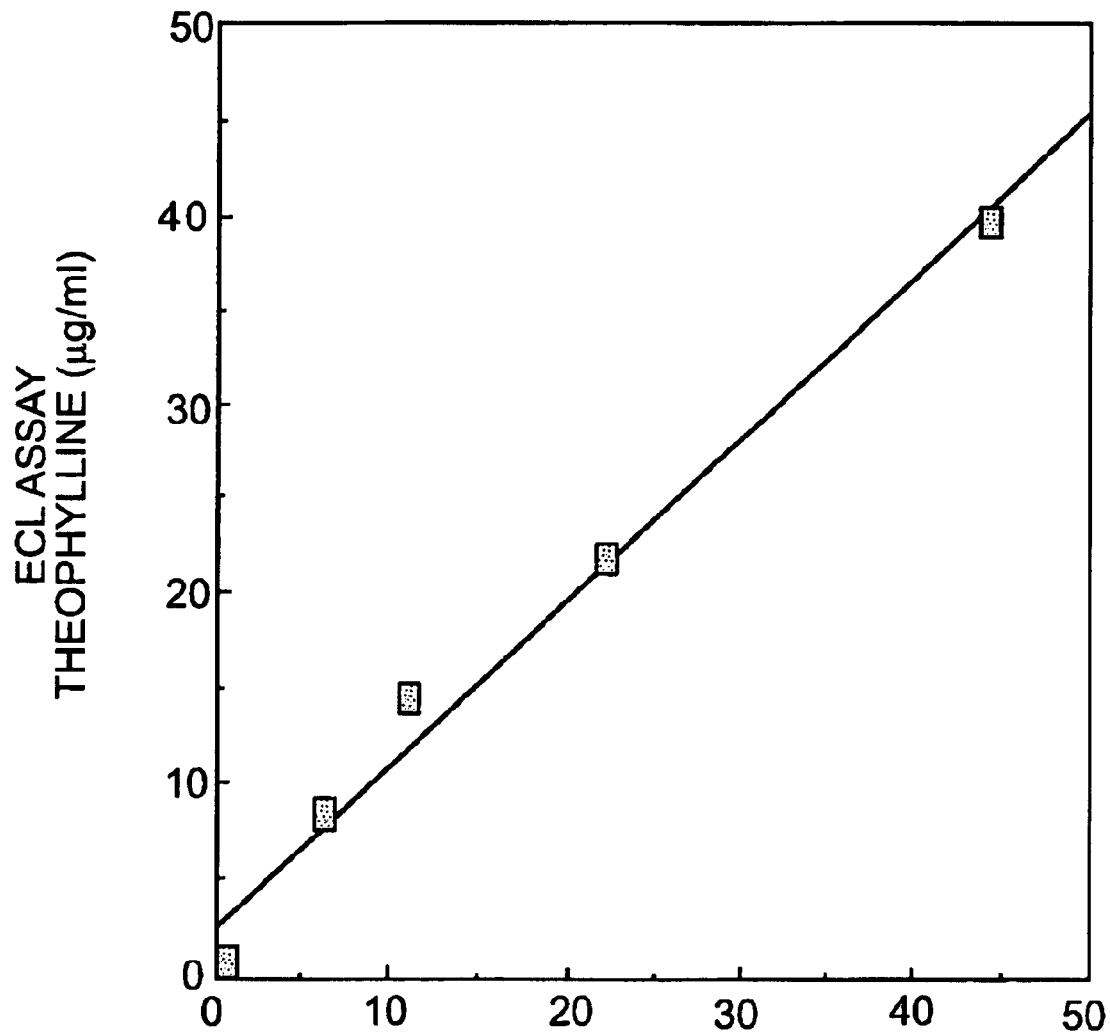
Figure 4D:
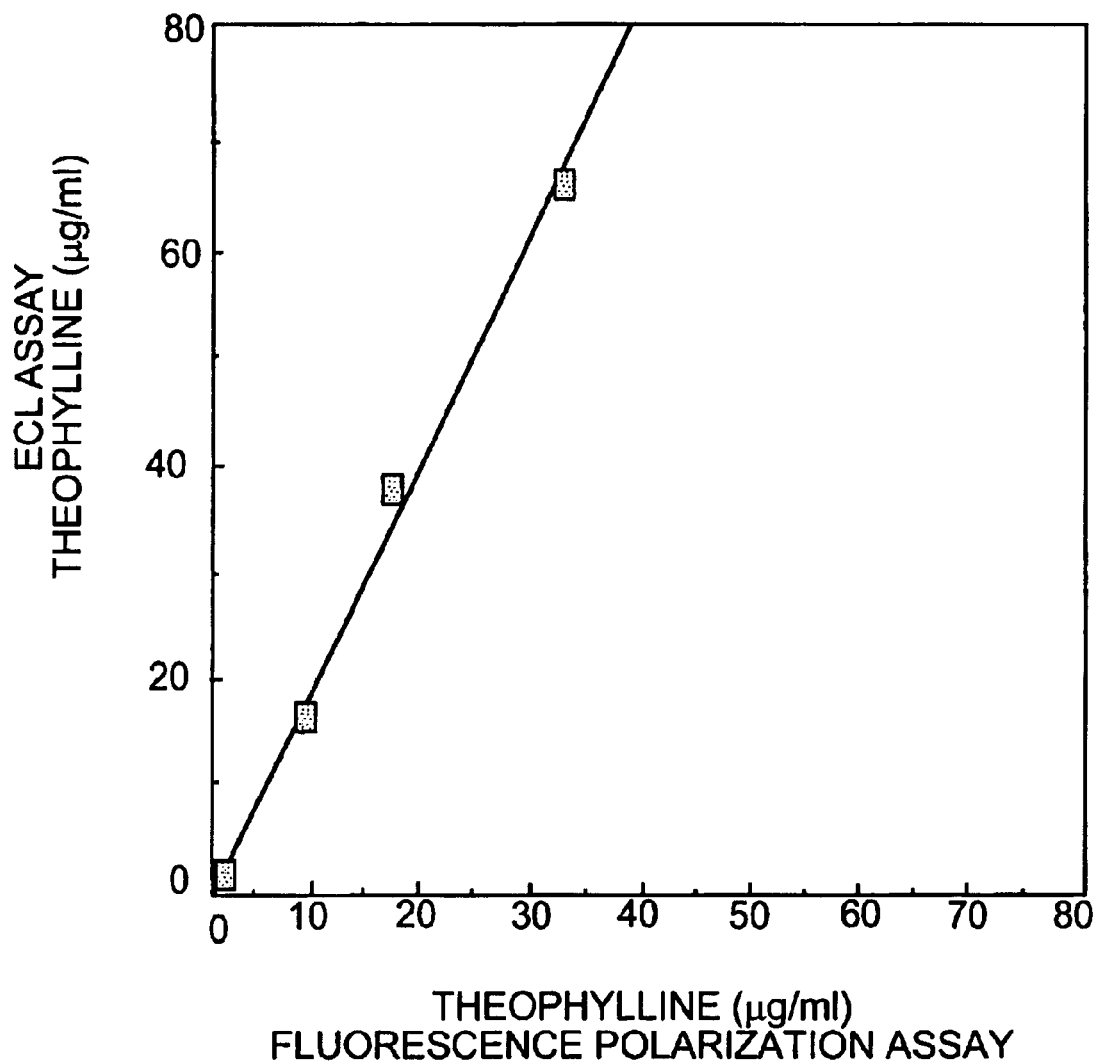

FIG. 4 graphically depicts the results of an ECL theophylline assay compared to the results of a fluorescence polarization theophylline assay.

A. Normal sera: n=4; slope=0.986; r=1.00.

B. Hemolyzed sera: n=3; slope=0.878; r=1.00

C. Lipemic sera: n=5; slope=0.872; r=0.99

D. Icteric sera: n=4; slope–2.14; r=1.00

Figure 5:
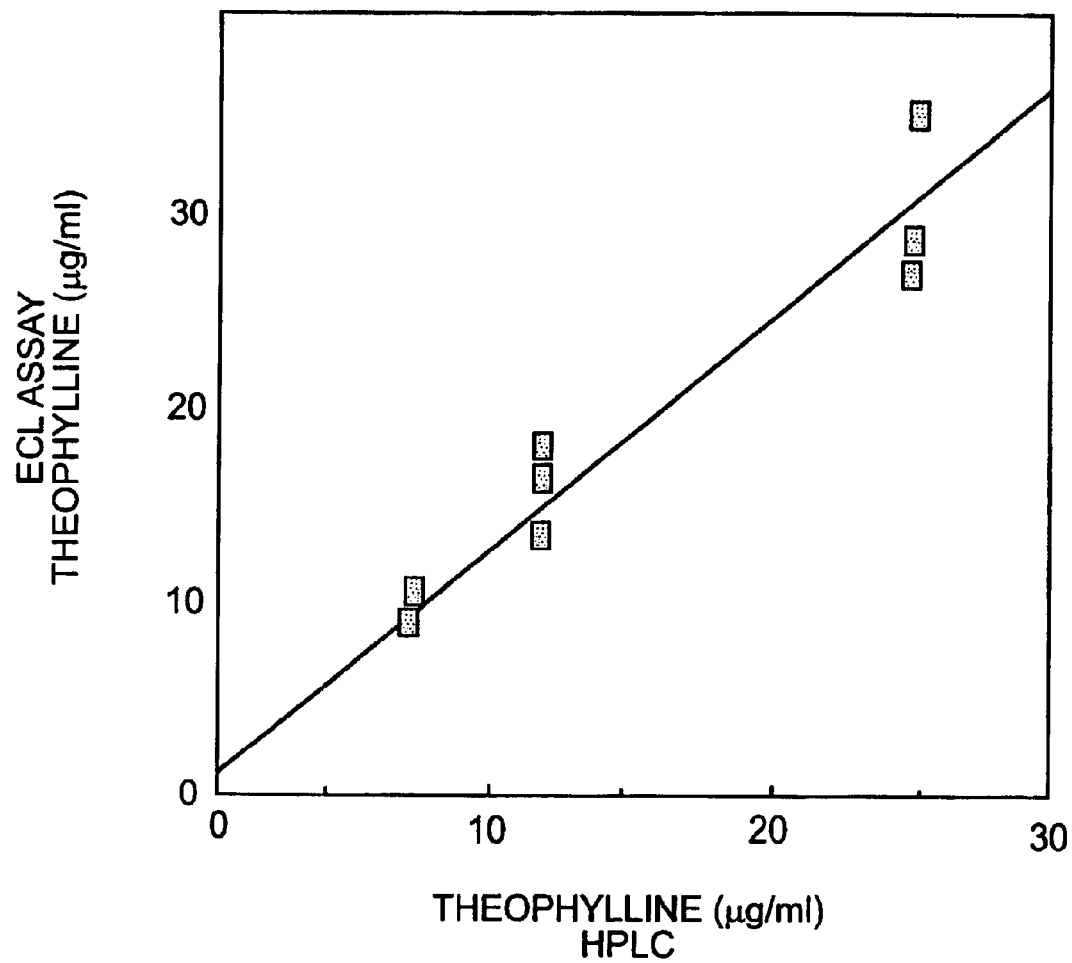

FIG. 5 graphically depicts the results of an ECL theophylline assay compared to the results from a high pressure liquid chromatography assay.

n=9; slope=0.197; r=0.98.

Figure 6:
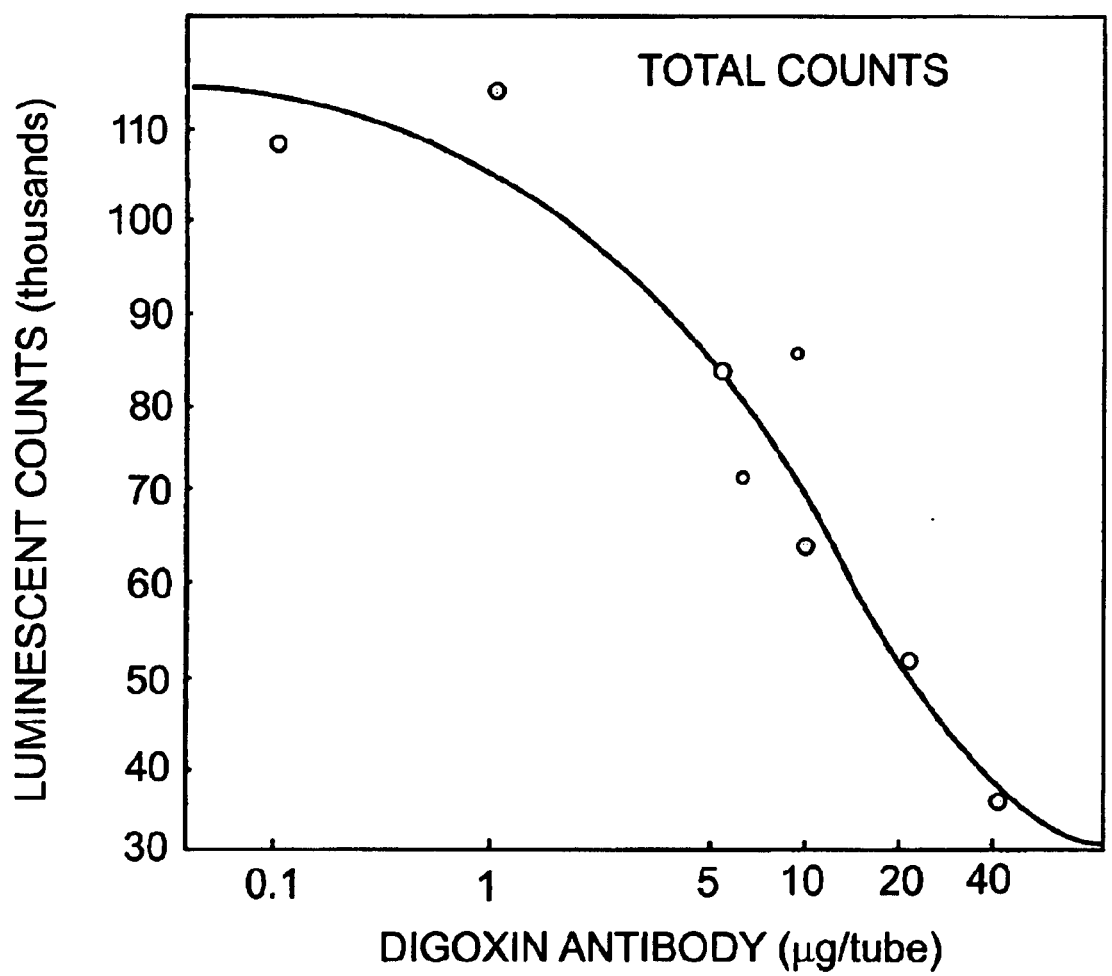

FIG. 6 graphically depicts the modulation of an ECL signal generated in an ECL digoxin immunoassay.

Figure 7:
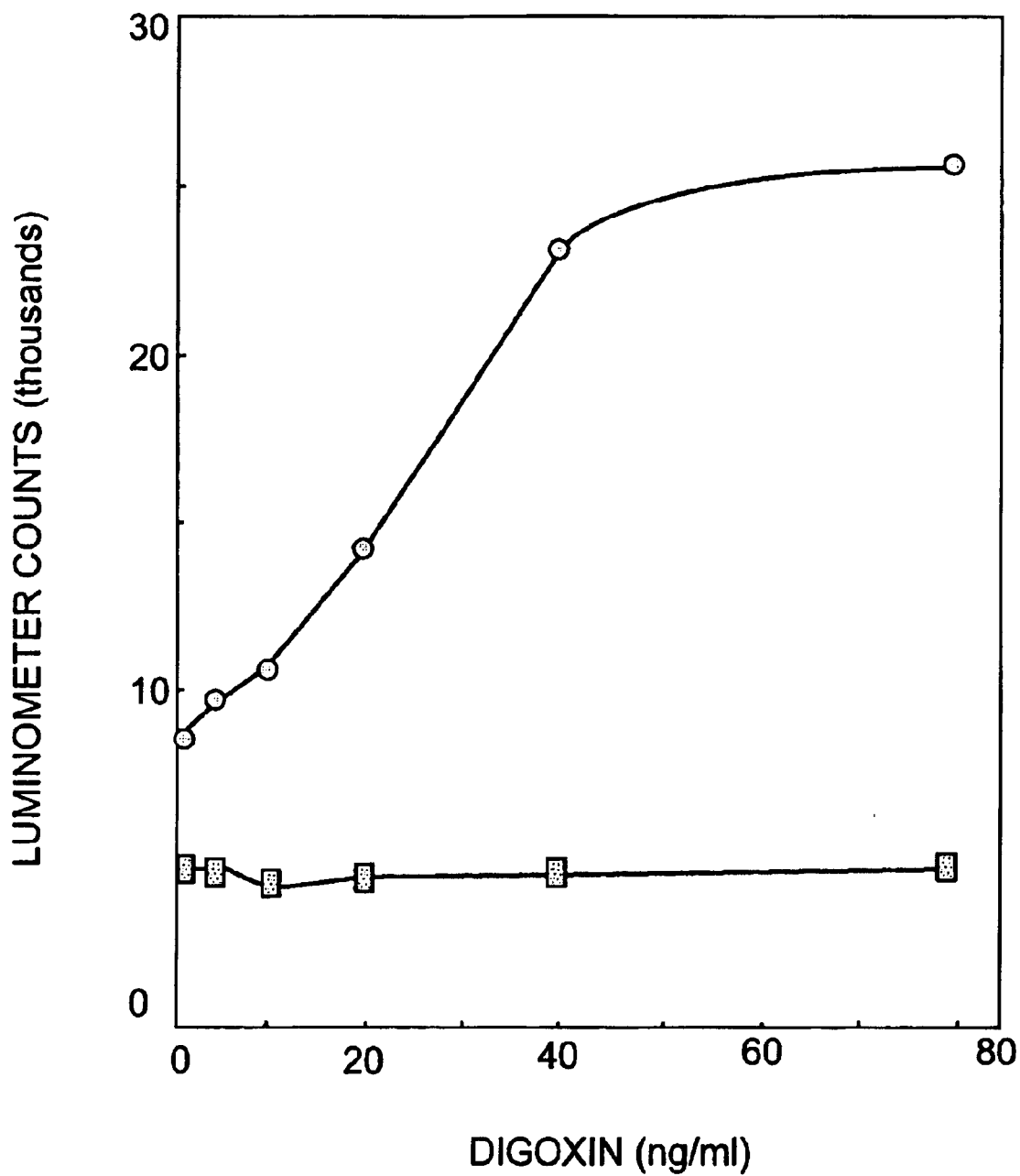

FIG. 7 graphically depicts the results of an ECL digoxin immunoassay.

■=Blank

●=Digoxin

Figure 8:
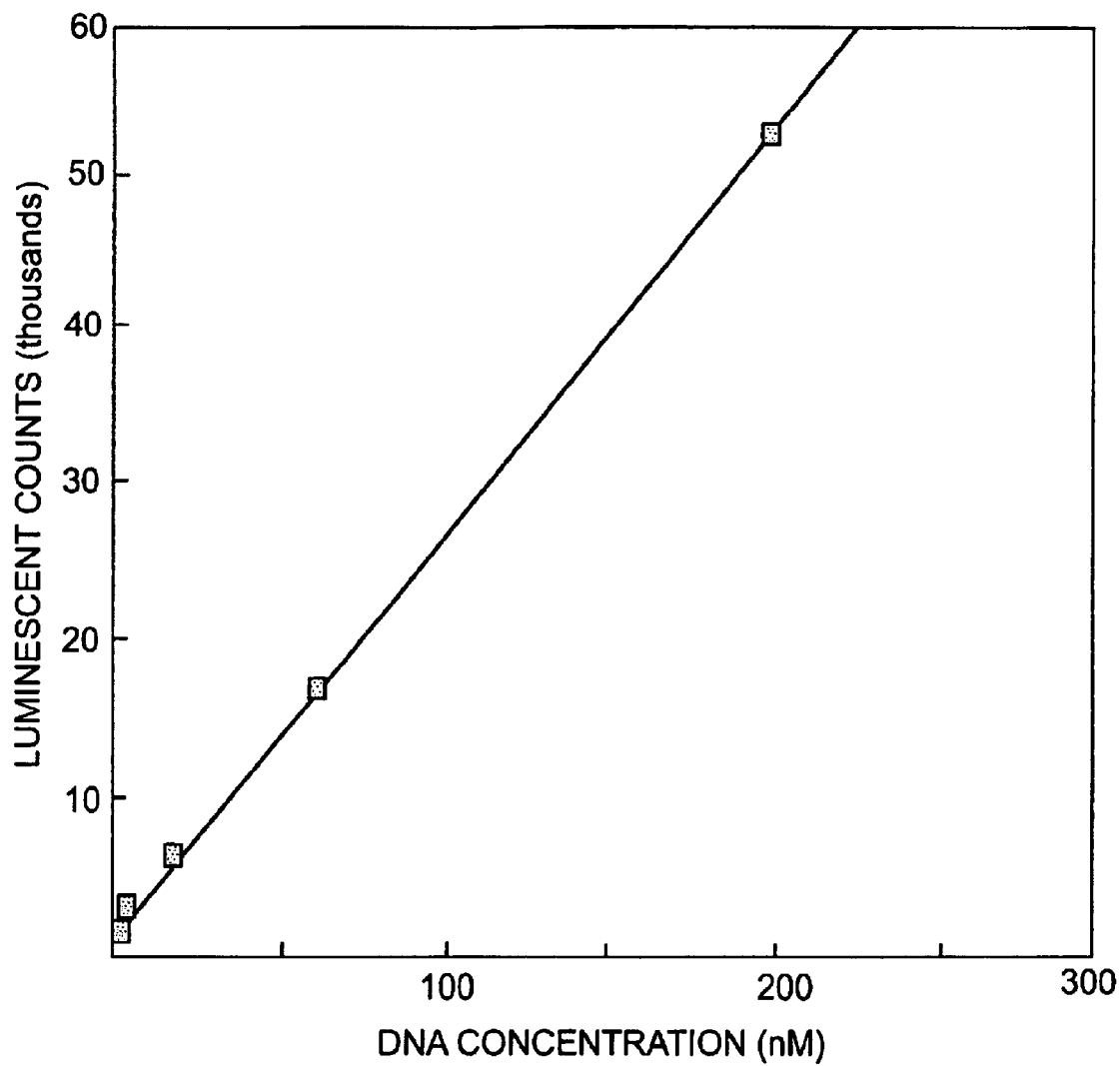

FIG. 8 graphically depicts the ECL signal generated by various concentrations of MBI 38-Compound I.

Figure 9:

FIG. 9 shows the results of a Hybridization/Sensitivity Study of MBI 38-Compound I.

TAG=Compound I

Figure 10:
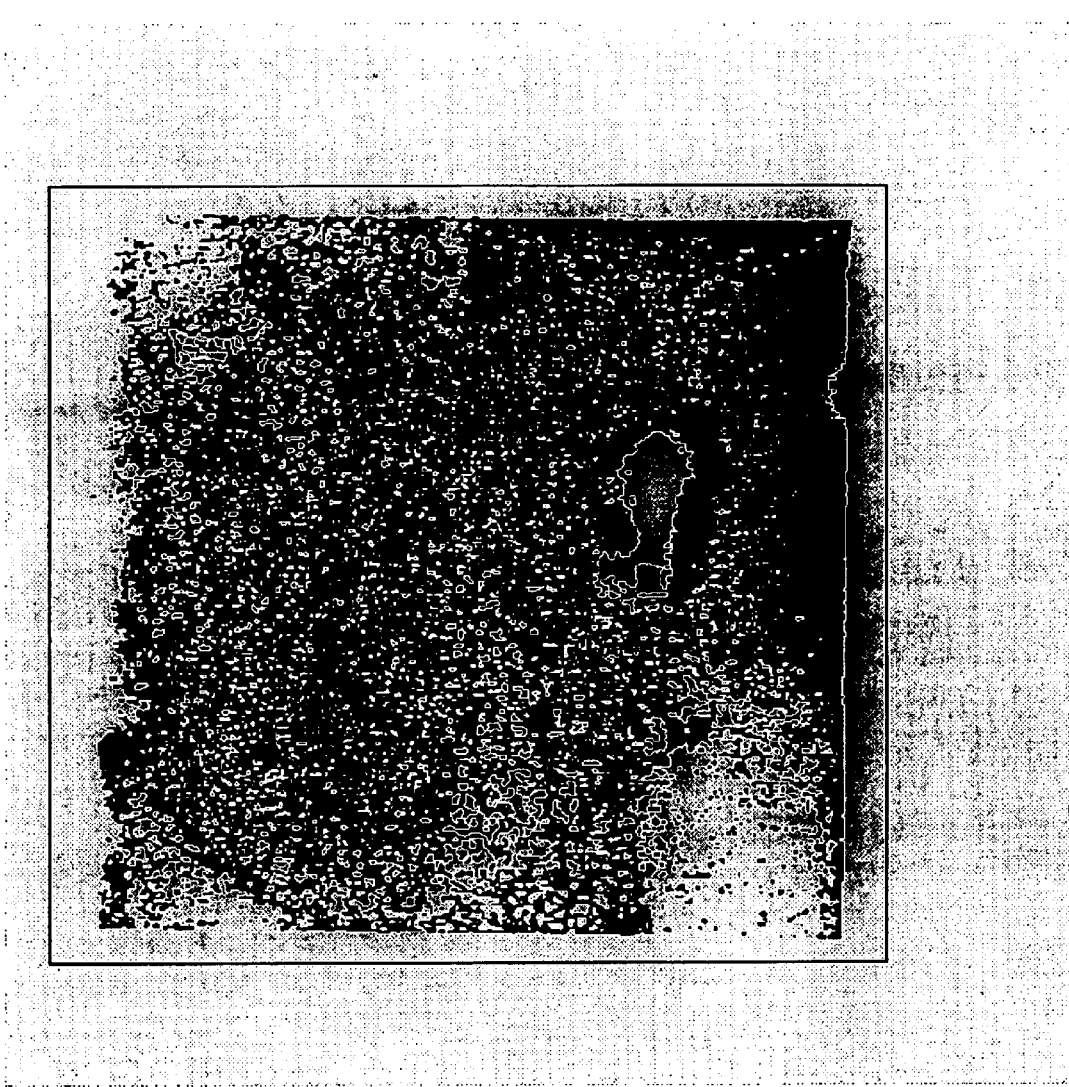

FIG. 10 shows the results of a Specificity Study of MBI 38-Compound I.

DETAILED DESCRIPTION OF THE INVENTION

The present invention provides a method of detecting in a predetermined volume of a multicomponent, liquid sample an analyte of interest present in the sample at a concentration below about $10^{-3}$ molar which comprises: a) contacting a sample with a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and the reagent combine; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and c) detecting electromagnetic radiation so emitted and thereby detecting the presence of the analyte of interest in the sample.

Within this application "molar" means the concentration of an analyte in solution in moles per liter or the amount of particulate matter present in a liquid sample in particles or units per liter. For example, $1 \times 10^{23}$ particles per liter may be expressed as 1 molar.

The methods provided by the present invention may be performed as heterogeneous assays, i.e. assays in which unbound labeled reagent is separated from bound labeled reagent prior to exposure of the bound labeled reagent to electrochemical energy, and homogeneous assays, i.e. assays in which unbound labeled reagent and bound labeled reagent are exposed to electrochemical energy together. In the homogeneous assays of the present invention the electromagnetic radiation emitted by the bound labeled reagent is distinguishable from the electromagnetic radiation emitted by the unbound labeled reagent, either as an increase or as a decrease in the amount of electromagnetic radiation emitted by the bound labeled reagent in comparison to the unbound labeled reagent, or as electromagnetic radiation of a different wavelength. Accordingly, in one embodiment of the invention any reagent which is not combined with the analyte of interest is separated from the sample, which had been contacted with the reagent, prior to exposure of the sample to electrochemical energy. In another embodiment of the invention, prior to contacting the sample with the reagent, the sample is treated so as to immobilize the analyte of interest. Means for immobilizing analytes of interest are well known within the art and include contacting the sample with a polystyrene, nitrocellulose or nylon surface, or a surface coated with whole cells, subcellular particles, viruses, prions, viroids, lipids, fatty acids, nucleic acids, polysaccharides, proteins, lipoproteins, lipopolysaccharides, glycoproteins, peptides, cellular metabolites, hormones, pharmacological agents, tranquilizers, barbiturates, alkaloids, steroids, vitamins, amino acids, sugars, nonbiological polymers, synthetic organic molecules, organometallic molecules or inorganic molecules. Additionally, the analyte of interest may be any of these substances. In one embodiment of the invention, the analyte of interest is theophylline. In another embodiment of the invention, the analyte of interest is digoxin. In still another embodiment of the invention, the analyte of interest is human chorionic gonadotropin (hCG). Furthermore, the analyte of interest may be a whole cell, subcellular particle, virus, prion, viroid, nucleic acid, protein, lipoprotein, lipopolysaccharide, glycoprotein, peptide, hormone, pharmacological agent, nonbiological polymer, synthetic organic molecule, organometallic molecule or an inorganic molecule present in the sample at a concentration below about $10^{-12}$ molar. Moreover the analyte of interest may be a whole cell, subcellular particle, virus, prion, viroid or nucleic acid present in the sample at a concentration below about $10^{-15}$ molar.

The reagent which is contacted with the sample may comprise an electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, nonbiological polymer, synthetic organic molecule, organometallic molecule, inorganic molecule, biotin, avidin or streptavidin. In one embodiment of the invention the agent is an electrochemiluminescent moiety conjugated to an antibody, antigen, nucleic acid, hapten, ligand or enzyme, or biotin avidin or streptavidin.

The electrochemiluminescent chemical moiety may comprise a metal-containing organic compound wherein the metal is selected from the group consisting of ruthenium, osmium, rhenium, iridium, rhodium, platinum, palladium, molybdenum and technetium. In one embodiment of the invention the metal is ruthenium or osmium. In another embodiment of the invention the electrochemiluminescent chemical moiety is rubrene or 9,10-diphenylanthracene. In still another embodiment of the invention, the electrochemiluminescent chemical moiety is bis[(4,4'-carbomethoxy)-2,2'-bipyridine]2-[3-(4-methyl-2,2'-bipyridine-4-yl)propyl]-1,3-dioxolane ruthenium (II). In yet another embodiment of the invention, the electrochemiluminescent chemical moiety is bis(2,2'bipyridine)[4-(butan-1-al)-4'-methyl-2,2'-bipyridine]ruthenium (II). In a further embodiment of the invention, the electrochemiluminescent chemical moiety is bis(2,2'-bipyridine)[4-(4'-methyl-2,2'-bipyridine-4'-yl)-butyric acid]ruthenium (II). In still another embodiment of the invention, the electrochemiluminescent chemical moiety is (2,2'-bipyridine)[cis-bis(1,2-diphenylphosphino)ethylene]{2-[3-(4-methyl-2,2'-bipyridine-4'-yl)propyl]-1,3-dioxolane}osmium (II). In yet a further embodiment of the invention, the electrochemiluminescent chemical moiety is bis(2,2'-bipyridine)[4-(4'-methyl-2,2'-bipyridine)-butylamine]ruthenium (II). In yet another embodiment of the invention the electrochemiluminescent chemical moiety is bis(2,2'-bipyridine)[1-bromo-4(4'-methyl-2,2'-bipyridine-4-yl)butane]ruthenium (II). In still a further embodiment of the invention, the electrochemiluminescent chemical moiety is bis(2,2'-bipyridine)maleimidohexanoic acid, 4-methyl-2,2'-bipyridine-4'-butylamide ruthenium (II).

The sample may be derived from a solid, emulsion, suspension, liquid or gas. Furthermore, the sample may be derived from water, food, blood, serum, urine, feces, tissue, saliva, oils, organic solvents or air. Moreover, the sample may comprise acetonitrile, dimethylsulfoxide, dimethylformamide, n-methyl-pyrrolidinone or tert-butyl alcohol. The sample may comprise a reducing agent or an oxidizing agent.

The present invention also provides a competitive method for detecting in a predetermined volume of a multicomponent, liquid sample an analyte of interest present in the sample at a concentration below about $10^{-3}$ molar which comprises: a) contacting the sample with a reagent (i) capable of being induced to repeatedly emit electromagnetic radiation upon exposure to an amount of electrochemical energy from a suitable source effective to induce the reagent to repeatedly emit radiation and (ii) capable of competing with the analyte of interest for binding sites on a complementary material not normally present in the sample, and with the complementary material, the contact being effected under appropriate conditions such that the analyte of interest and the reagent competitively bind to the complementary material; b) exposing the resulting sample to an amount of electrochemical energy from a suitable source effected to induce the reagent to repeatedly emit radiation, the exposure being effected under suitable conditions so as to induce the reagent to repeatedly emit electromagnetic radiation; and c) detecting electromagnetic radiation so emitted and thereby detecting the presence of the analyte of interest in the sample.

The reagent may be the analyte of interest conjugated to an electrochemiluminescent chemical moiety or an analogue of the analyte of interest conjugated to an electrochemiluminescent moiety. Additionally, the analyte of interest may be theophylline, digoxin or hCG. Moreover, the electrochemiluminescent chemical moiety may be bis[(4,4'-carbomethoxy)-2,2'-bipyridine]2-[3-(4-methyl-2,2'-bipyridine-4-yl)propyl]-1,3-dioxolane ruthenium (II). In yet another embodiment of the invention, the electrochemiluminescent chemical moiety is bis(2,2'-bipyridine)[4-(butan-1-al)-4'-methyl-2,2'-bipyridine]ruthenium (II). In a further embodiment of the invention, the electrochemiluminescent chemical moiety is bis(2,2'-bipyridine)[4-(4-methyl-2,2'-bipyridine-4'-yl)-butyric acid]ruthenium (II). In still another embodiment of the invention, the electrochemiluminescent chemical moiety is (2,2'-bipyridine)[cis-bis(1,2-diphenylphosphino)ethylene]{2-[3-(4-methyl-2,2'-bipyridine-4'-yl)propyl]-1,3-dioxo-lane}osmium (II). In yet a further embodiment of the invention, the electrochemiluminescent chemical moiety is bis(2,2'-bipyridine)[4-(4'-methyl-2,2'-bipyridine)-butylamine]ruthenium (II). In yet another embodiment of the invention the electrochemiluminescent chemical moiety is bis(2,2'-bipyridine)[1-bromo-4(4'-methyl-2,2'-bipyridine-4-yl)butane]ruthenium (II). In still a further embodiment of the invention, the electrochemiluminescent chemical moiety is bis(2,2'-bipyridine) maleimidohexanoic acid, 4-methyl-2,2'-bipyridine-4'-butylamide ruthenium (II).

The complementary material may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, steroid, vitamin, amino acid, sugar, non-biological polymer, synthetic organic molecule, organometallic molecule or inorganic molecule.

It is within the scope of this application that the methods provided herein may be performed so as to quantify an analyte of interest. Accordingly the present invention provides a method for quantitatively determining in a predetermined volume of a multicomponent, liquid sample, the amount of an analyte of interest present in the sample which comprises: a) contacting the sample with a known amount of a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and reagent combine; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and c) quantitatively determining the amount of radiation so emitted and thereby quantitatively determining the amount of the analyte of interest present in the sample.

This method may be performed as a heterogeneous assay or as a homogeneous assay. In one embodiment of the invention any reagent which is not combined with the analyte of interest is separated from the sample, which had been contacted with a known amount of the reagent, prior to the exposure of the sample to an amount of electrochemical energy from a suitable source effective to induce the reagent to repeatedly emit radiation. In yet another embodiment of the invention, prior to contacting the sample with the reagent, the sample is treated so as to immobilize the analyte of interest.

The analyte of interest may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, non-biological polymer, synthetic organic molecule, organometallic molecule or inorganic molecule. In one embodiment of the invention, the analyte of interest is theophylline. In another embodiment of the invention, the analyte of interest is digoxin. In yet another embodiment of the invention, the analyte of interest is hCG.

The reagent with which the sample is contacted may be an electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, non-biological polymer, synthetic organic molecule, organometallic molecule or inorganic molecule.

In one embodiment of the invention the reagent is a electrochemiluminescent chemical moiety conjugated to an antibody, antigen, nucleic acid, hapten, ligand or enzyme, or biotin, avidin or streptavidin.

The electrochemiluminescent moiety may be a metal-containing organic compound wherein the metal is selected from the group consisting of ruthenium, osmium, rhenium, iridium, rhodium, platinum, palladium, molybdenum and technetium. In one embodiment of the invention the metal is ruthenium or osmium. In another embodiment of the invention the electrochemiluminescent chemical moiety is rubrene or 9,10-diphenylanthracene. In still a further embodiment of the invention, the electrochemiluminescent chemical moiety is bis[(4,4'-carbomethoxy)-2,2'-bipyridine]2-[3-(4-methyl-2,2'-bipyridine-4-yl)propyl]-1,3-dioxolane ruthenium (II). In yet another embodiment of the invention, the electrochemiluminescent chemical moiety is bis(2,2'-bipyridine)[4-(butan-1-al)-4'-methyl-2,2'-bipyridine]ruthenium (II). In a further embodiment of the invention, the electrochemiluminescent chemical moiety is bis(2,2'-bipyridine)[4-(4-methyl-2,2'-bipyridine-4'-yl)-butyric acid] ruthenium (II). In still another embodiment of the invention, the electrochemiluminescent chemical moiety is (2,2'-bipyridine)[cis-bis(1,2-diphenylphosphino)ethylene]{2-[3-(4-methyl-2,2'-bipyridine-4'-yl)propyl]-1,3-dioxolane}osmium (II). In yet a further embodiment of the invention, the electrochemiluminescent chemical moiety is bis(2,2;-bipyridine)[4-(4'-methyl-2,2'-bipyridine)-butylamine]-ruthenium (II). In yet another embodiment of the invention the electrochemiluminescent chemical moiety is bis(2,2'-bipyridine)[1-bromo-4(4'-methyl-2,2'-bipyridine-4-yl)butane]ruthenium (II). In still a further embodiment of the invention, the electrochemiluminescent chemical moiety is bis(2,2'-bipyridine)maleimidohexanoic acid, 4-methyl-2,2'-bipyridine-4'-butylamide ruthenium (II).

The sample may be derived from a solid, emulsion, suspension, liquid or gas. Samples which comprise the analyte of interest may be derived from water, food, blood, serum, urine, feces, tissue, saliva, oils, organic solvents or air. Additionally, samples may comprise acetonitrile, dimethylsulfoxide, dimethylformamide, n-methylpyrrolidinone or tert-butyl alcohol. Furthermore, the sample may comprise a reducing agent or an oxidizing agent.

The invention also provides a competitive method for quantitatively determining in a predetermined volume of a multicomponent, liquid sample the amount of an analyte of interest present in the sample. This method comprises: a) contacting the sample with a known amount of a reagent (i) capable of being induced to repeatedly emit electromagnetic radiation upon exposure to an amount of electrochemical energy from a suitable source effective to induce the reagent to repeatedly emit radiation and (ii) capable of competing with the analyte of interest for binding sites on a complementary material not normally present in the sample, and with a known amount of the complementary material, the contact being effected under appropriate conditions such that the analyte of interest and the reagent competitively bind to the complementary material; b) exposing the resulting sample to an amount of electrochemical energy from a suitable source effective to induce the reagent to repeatedly emit radiation, the exposure being effected under suitable conditions so as to induce the reagent to repeatedly emit electromagnetic radiation; and c) quantitatively determining the amount of radiation so emitted and thereby quantitatively determining the amount of the analyte of interest present in the sample.

The analyte of interest may be theophylline, digoxin or hCG.

In one embodiment of the invention, the reagent is the analyte of interest conjugated to an electrochemiluminescent chemical moiety or an analogue of the analyte of interest conjugated to an electrochemiluminescent chemical moiety. The electrochemiluminescent chemical moiety may be bis[(4,4'-carbomethoxy)-2,2'-bipyridine]2-[3-(4-methyl-2,2'-bipyridine-4-yl)propyl]-1,3-dioxolane ruthenium (II). In another embodiment of the invention, the electrochemiluminescent chemical moiety is bis(2,2'-bipyridine)[4-(butan-1-al)-4'-methyl-2,2'-bipyridine]ruthenium (II). In a further embodiment of the invention, the electrochemiluminescent chemical moiety is bis(2,2'-bipyridine)[4-(4-methyl-2,2'-bipyridine-4'-yl)-butyric acid]ruthenium (II). In yet a further embodiment of the invention, the electrochemiluminescent chemical moiety is (2,2'-bipyridine)[cis-bis(1,2-diphenylphosphino)ethylene]{2-[3-(4-methyl-2,2'-bipyridine-4'-yl)propyl]-1,3-dioxolane}osmium (II). In yet a further embodiment of the invention, the electrochemiluminescent chemical moiety is bis(2,2'-bipyridine)[4-(4'-methyl-2,2'-bipyridine)butylamine]ruthenium II. In yet another embodiment of the invention the electrochemiluminescent chemical moiety is bis(2,2'-bipyridine)[1-bromo-4 (4'-methyl-2,2'-bipyridine-4-yl)butane]ruthenium (II). In still a further embodiment of the invention, the electrochemiluminescent chemical moiety is bis(2,2'-bipyridine) maleimidohexanoic acid, 4-methyl-2,2'-bipyridine-4'-butylamide ruthenium (II).

The complementary material may be a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, non-biological polymer, synthetic organic molecule, organometallic molecule or inorganic molecule.

The present invention further provides a method for detecting and identifying the presence of a multiplicity of analytes of interest in a liquid food or food homogenate. This method comprises: a) immersing into the liquid food or food homogenate a portion of a diagnostic reagent holder suitable for immersing into a liquid or solid suspension and having immobilized to it a multiplicity of reagents, each reagent being immobilized to the diagnostic reagent holder in distinct, identifiable regions and capable of forming a complex with a single analyte of interest so as to allow the formation of immobilized reagent-analyte of interest complexes; b) removing the diagnostic reagent holder from the liquid food or food homogenate; c) rinsing the diagnostic reagent holder with a suitable rinsing solution; d) immersing the portion of the diagnostic reagent holder which contains the immobilized reagent-analyte of interest complexes into a detection solution which contains at least one detection reagent capable of forming complexes with the immobilized reagent-analyte of interest complexes so as to allow the formation of immobilized reagent-analyte of interest-detection reagent complexes; and e) detecting the presence on the identifiable regions of the diagnostic reagent holder to which reagents are immobilized of immobilized reagent-analyte of interest-detection reagent complexes, thereby detecting and identifying the presence of a multiplicity of analytes of interest in the liquid food or food homogenate.

The analytes of interest may be microorganisms. The microorganisms may be viable or nonviable. Additionally, the microorganisms may be bacteria. Examples of bacteria which may be detected by this method include, but are not limited to, *Salmonella, Campylobacter, Escherichia, Yersinia, Bacillus, Vibrio, Legionella, Clostridium, Streptococcus* or *Staphylococcus*.

Additionally, the analytes of interest may be antigens. Such antigens include, but are not limited to, enterotoxins and aflatoxins.

The immobilized reagents and the detection reagents may be polyclonal antibodies, monoclonal antibodies, mixtures of monoclonal antibodies, or mixtures of polyclonal and monoclonal antibodies.

The detection reagents may be labeled with a detectable marker. In one embodiment of the invention the detection reagents are each labeled with the same detectable marker. Such markers are well known in the art and may comprise an enzyme, e.g. alkaline phosphatase, horseradish peroxidase, glucose oxidase, beta-galactosidase or urease, a fluorescent moiety, e.g. fluoresceinisothiocyanate, tetramethylrhodamine isothiocyanate, dichlorotriazinylamino fluorescein or Texas Red or a chemiluminescent moiety, e.g. luminol, isoluminol or an acridinium ester. Moreover, the detectable marker may be an electrochemiluminescent chemical moiety capable of being induced to repeatedly emit electromagnetic radiation upon exposure to an amount of electrochemical energy from a suitable source effective to induce the moiety to emit radiation. This electrochemiluminescent chemical moiety may comprise ruthenium or osmium.

The immobilized reagents may be immobilized to a nitrocellulose membrane which is attached to the diagnostic reagent holder.

The present invention also provides a kit useful for detecting and identifying the presence of a multiplicity of enterotoxins in a sample. This kit comprises: a) a diagnostic reagent holder provided with a handle connected to a surface area suitable for immersing into a liquid or solid suspension, said surface area having at least one nitrocellulose membrane attached to it, said nitrocellulose membrane having a multiplicity of monoclonal antibodies separately and distinctly immobilized to identifiable regions on it, each immobilized monoclonal antibody being specific for an antigenic determinant on one enterotoxin; b) a first rinsing solution which comprises a buffered-aqueous solution containing a surfactant; c) a detection which comprises at least one monoclonal antibody enzyme conjugate, the monoclonal antibody of which is specific for antigenic determinants different from but located on each enterotoxin for which the monoclonal antibodies immobilize to the nitrocellulose membrane attached to the diagnostic reagent holder are specific; d) a second rinsing solution which comprises a buffered-aqueous solution; e) an enzyme substrate capable of reacting with the enzyme conjugated to the detection solution monoclonal antibody; and f) a colorless dye.

In one embodiment of the invention the nitrocellulose membrane is provided with monoclonal antibodies which are separately and distinctly immobilized to it and which are specific for antigenic determinants on a multiplicity of *Staphylococcal* enterotoxins. In another embodiment of the invention the nitrocellulose membrane is provided with four monoclonal antibodies which are separately and distinctly immobilized to it and which are specific for *Staphylococcal* enterotoxins A, B, D and E. Furthermore, this nitrocellulose membrane may be additionally provided with a monoclonal antibody which is separately and distinctly immobilized to it and which is specific for an antigenic determinant on more than one *Staphylococcal* enterotoxin. This enterotoxin may be specific for antigenic determinants on *Staphylococcal* enterotoxins $C_1$, $C_2$ and $C_3$. The enzyme of this kit which is conjugated to the monoclonal antibody which is specific for antigenic determinant different from but located on each *Staphylococcal* enterotoxin for which the nitrocellulose immobilized monoclonal antibodies are specific may be alkaline phosphatase, the enzyme substrate which is capable of reacting with the enzyme is 5-bromo, 4-chloro indolyl phosphate and the colorless dye is nitroblue tetrazolium.

The invention further provides a method for detecting and identifying the presence of a multiplicity of *Staphylococcal* enterotoxins in a liquid or solid suspension. This method comprises: a) immersing a diagnostic reagent holder provided with a multiplicity of monoclonal antibodies specific for *Strephylococcal* enterotoxins and which are separately and distinctly immobilized to it into the liquid or solid suspension for a suitable length of time so as to allow the formation of immobilized monoclonal antibody-*Staphylococcal* enterotoxin complexes; b) removing the diagnostic reagent holder from the sample; c) immersing the diagnostic holder into a buffered-aqueous solution which comprises a surfactant; d) removing the diagnostic reagent holder from the buffered-aqueous solution which contains a surfactant; e) immersing the diagnostic reagent holder into a detection solution which comprises a monoclonal antibody-alkaline phosphatase conjugate for a suitable length of time so as to allow the formation of immobilized monoclonal antibody-*Staphylococcal* enterotoxin-monoclonal antibody-alkaline phosphatase complexes; f) removing the diagnostic reagent holder from the detection solution; g) immersing the diagnostic reagent holder into the a buffered-aqueous solution; h) removing the diagnostic reagent holder from the buffered-aqueous solution; i) immersing the diagnostic reagent holder into a solution which comprises 5-bromo, 4-chloro indolyl phosphate and nitroblue tetrazolium; j) visibly detecting the identifiable regions of the nitrocellulose membrane onto which a blue precipitate accumulates; k) correlating the identifiable regions of the nitrocellulose membrane onto which a blue precipitate accumulates with the *Staphylococcal* enterotoxin for which the monoclonal antibody immobilized to the region is specific, thereby indicating the presence and the identity of a multiplicity of *Staphylococcal* enterotoxins in the sample.

Also provided is a method for detecting the presence of at least one species of bacteria in a sample. This method comprises: a) inoculating the sample into at least one receptacle which is provided with an open end and which contains a suitable medium for supporting the growth of the species of bacteria; b) coupling a cap to the end of the receptacle, the face of the cap which when coupled to the receptacle, is exposed to the interior of the receptacle being provided with a surface suitable for immobilizing at least a component of the bacteria; c) incubating the inoculated media under conditions so as to allow bacteria inoculated into the media to reproduce; d) turning each receptacle upside-down for a suitable length of time so as to allow components of the bacterium present in the medium to become immobilized to the surface of the cap which is exposed to the interior of the receptacle; e) turning the upside-down receptacle rightside-up; f) uncoupling the cap from the receptacle, g) contacting the surface of the cap which has components of the bacteria immobilized to it with a reagent capable of forming a complex with the immobilized components of the bacteria under conditions so as to allow the formation of immobilized bacterial component-reagent complexes; and h) detecting immobilized bacterial component-reagent complexes, thereby detecting the presence of the species of bacteria within the sample.

Within this application "component of bacteria" includes, but is not limited to, a whole cell, cell wall component, cell membrane component and flagellar component.

The surface of the cap which is suitable for immobilizing at least a component of the bacteria may be a polystyrene insert, a nitrocellulose membrane or a nylon membrane. Furthermore, the surface may be coated with a polyclonal antibody, a monoclonal antibody, a mixture of monoclonal antibodies or a mixture of polyclonal and monoclonal antibodies.

The reagent capable of forming a complex with the immobilized bacterial components may be a polygonal antibody, a monoclonal antibody, a mixture of monoclonal antibodies or a mixture of polyclonal and monoclonal antibodies. Furthermore, the reagent may be labeled with a detectable marker, for example a detectable enzyme, a fluorescent moiety or a chemiluminescent moiety. Additionally, the detectable marker may be an electrochemiluminescent moiety. In one embodiment of the invention, the electrochemiluminescent moiety comprises ruthenium or osmium.

In yet another embodiment of the invention, the immobilized bacterial component-reagent complexes may be detected with a detectably marked second reagent capable of forming a complex with the immobilized bacterial component-reagent complexes. In still another embodiment of the invention the reagent may be a polyclonal antibody, a monoclonal antibody, a mixture of monoclonal antibodies or a mixture of polyclonal and monoclonal antibodies and the second reagent may be a detectably marked anti-antibody directed to the reagent.

Samples in which bacteria may be detected include water and food.

In one embodiment of the invention the medium suitable for supporting the growth of the species of bacteria is a non-selective lactose medium. In one embodiment of the invention the medium is a nonselective lactose medium and the species of bacteria which is detected is at least one coliform.

A method for detecting the presence of coliform bacteria in a sample is also provided by the invention. This method comprises: a) inoculating the sample into at least one receptacle which has an open end and contains a non-selective lactose medium and an inverted Durham; b) coupling a cap provided with a polystyrene insert to the open end of each receptacle, c) incubating the inoculated medium for at least 2 hours at 37° C.; d) determining whether each receptacle has gas produced by bacterial fermentation trapped within the inverted Durham vial; e) turning receptacles which have gas trapped within the inverted Durham vial upside-down for a suitable length of time so as to allow coliform bacteria present in the medium to form coliform-polystyrene complexes; f) turning the upside-down receptacles rightside-up; g) uncoupling the caps from the receptacles; h) treating the polystyrene inserts of the uncoupled caps with a substance suitable for blocking unbound sites; i) treating the polystyrene insert of the caps which had been treated with a substance suitable for blocking unbound sites with at least one anti-coliform bacteria antibody labeled with a detectable marker and capable of binding to coliform bacteria under conditions so as to allow the formation of antibody-coliform-polystyrene complexes; and j) detecting the presence of antibody-coliform-polystyrene complexes on the polystyrene insert, thereby detecting the presence of coliform bacteria in the sample.

In one embodiment of the invention the non-selective lactose medium is phenol red broth.

The substance suitable for blocking unbound sites on the polystyrene insert may be bovine serum albumin.

The anti-coliform bacteria antibody labeled with a detectable marker may be a monoclonal antibody labeled with a detectable marker. The detectable marker may be an enzyme conjugated to the monoclonal antibody. In one embodiment of the invention the enzyme is calf intestinal alkaline phosphatase. In another embodiment of the invention the detectable marker is a fluorescent moiety conjugated to the monoclonal antibody. In still another embodiment of the invention the detectable marker is an electrochemiluminescent moiety conjugated to the monoclonal antibody. The electrochemiluminescent moiety may comprise ruthenium or osmium.

In one embodiment of the invention the sample is water. In another embodiment of the invention the sample is food.

The receptacle which has an open end may be a vial.

Also provided is a kit for detecting in water samples the presence of coliform bacteria. This kit comprises: a) at least one vial containing a non-selective lactose medium; b) at least one Durham vial; c) at least one vial cap provided with a polystyrene insert; d) a solution of bovine serum albumin; e) an anti-coliform bacteria monoclonal antibody-enzyme conjugate; f) a buffered-aqueous wash solution; and g) a solution of enzyme substrate. In one embodiment of the invention the enzyme conjugated to the anti-coliform bacteria monoclonal antibody is calf intestinal alkaline phosphatase and the enzyme substrate is p-nitrophenyl phosphate disodium.

The invention also provides a compound having the structure

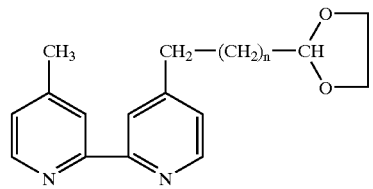

wherein n is an integer. In one embodiment of the invention, n is 2.

Further, the invention provides a compound having the structure

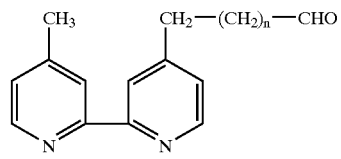

wherein n is an integer. In one embodiment of the invention, n is 2.

The invention also provides a compound having the structure

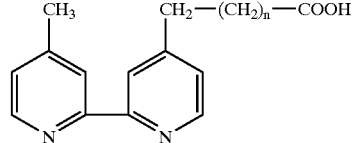

wherein n is an integer. In one embodiment of the invention, n is 2.

Also, the invention provides a compound having the structure

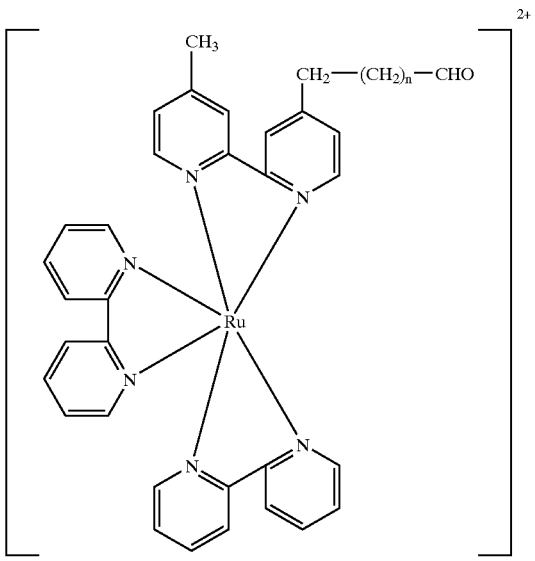

wherein R is an anion and n is an integer. In one embodiment of the invention, n is 2.

This compound may comprise a composition of matter having the structure

wherein X represents one or more nucleotides which may be the same or different, one or more amino acids which may be the same or different, an antibody, an analyte of interest or an analogue of an analyte of interest, n represents an integer, and Z represents the compound provided by this invention.

The invention further provides a compound having the structure

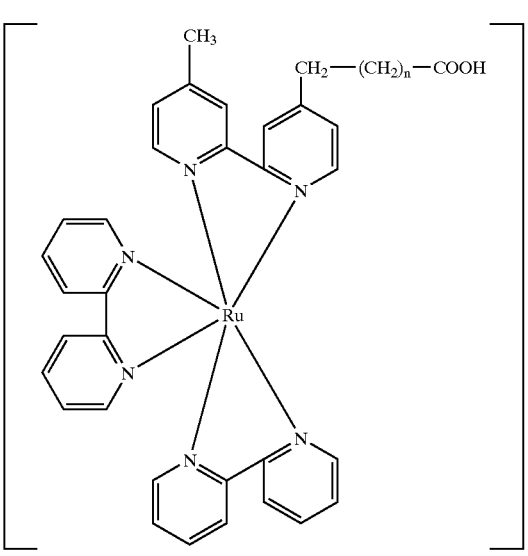

wherein R is an anion an n is an integer. In one embodiment of the invention, n is 2.

This compound may comprise a composition of matter having the structure

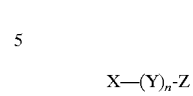

wherein X represents one or more nucleotides which may be the same or different, one or more amino acids which may be the same or different, an antibody, an analyte of interest or an analogue of an analyte of interest, n represents an integer, and Z represents the compound provided by this invention.

Also provided is a compound having the structure

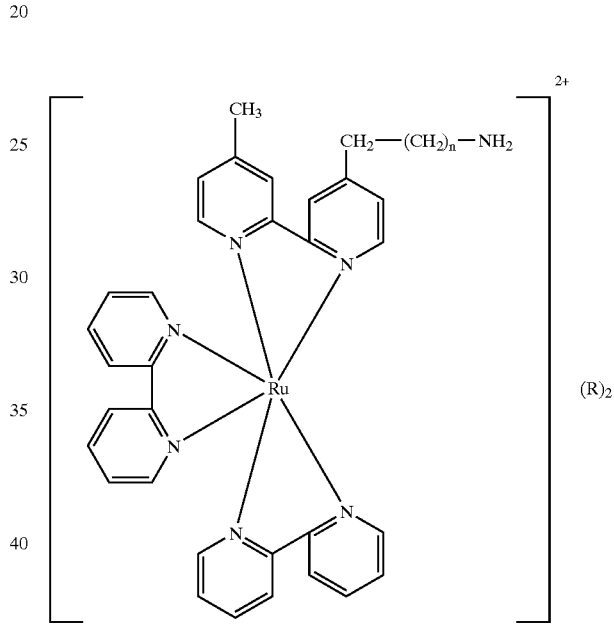

wherein R is an anion and n is an integer. In one embodiment of the invention, n is 3.

This compound may comprise a composition of matter having the structure

wherein X represents one or more nucleotides which may be the same or different, one or more amino acids which may be the same or different, an antibody, an analyte of interest or an analogue of an analyte of interest, n represents an integer, and Z represents the compound provided by this invention.

The invention further provides a compound having the structure

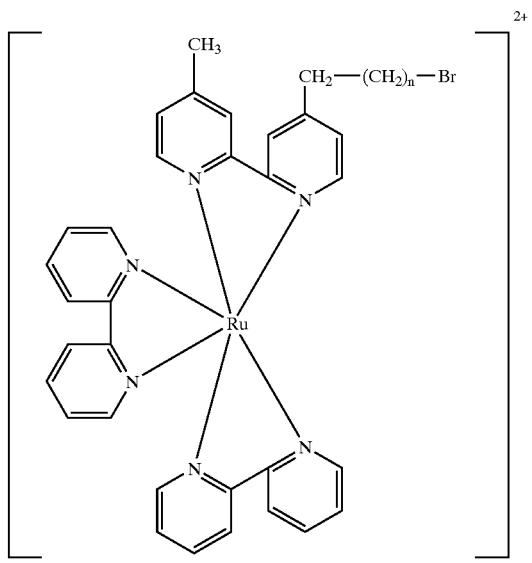

wherein R is an anion and n is an integer. In one embodiment of the invention, n is 3.

This compound may comprise a composition of matter having the structure $$X-(Y)_n-Z$$

wherein X represents one or more nucleotides which may be the same or different, one or more nucleotides which may be the same or different, an antibody, an analyte of interest or an analogue of an analyte of interest, n represents an integer, and Z represents the compound provided by this invention.

The invention also provides a compound having the structure

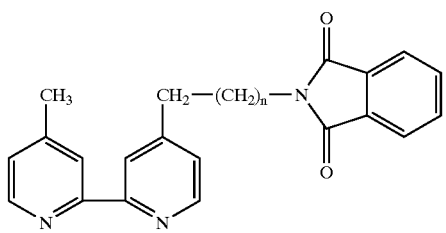

wherein n is an integer. In one embodiment of the invention, n is 3.

Also, the invention provides a compound having the structure

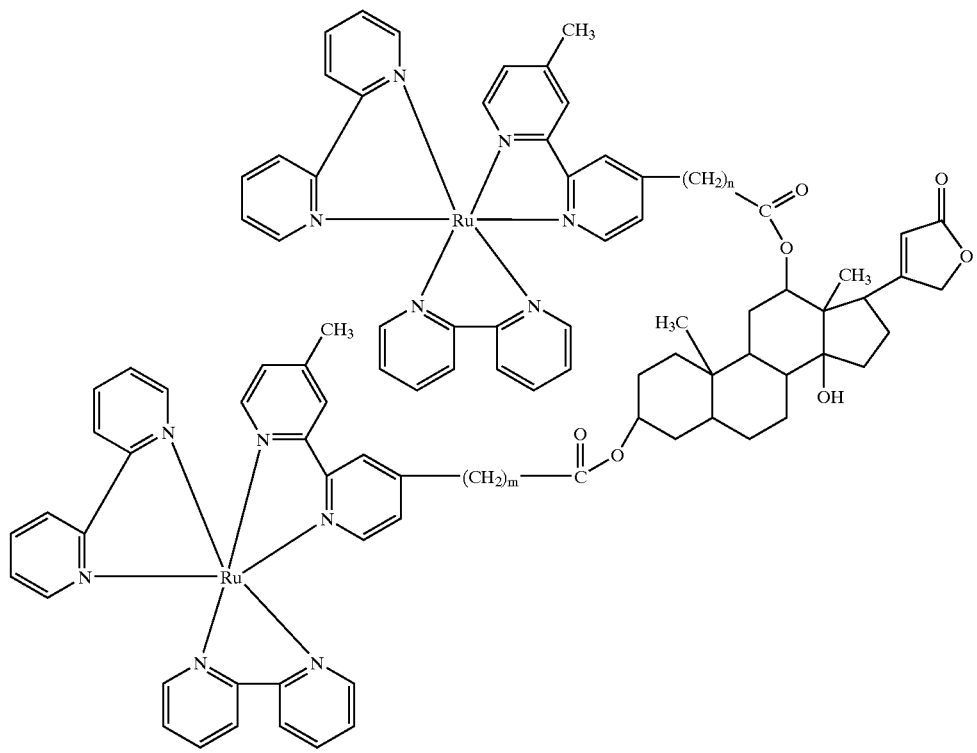

wherein m and n are each integers which may be the same or different. In one embodiment of the invention, m and n are both 3.

Further the invention provides a compound having the structure

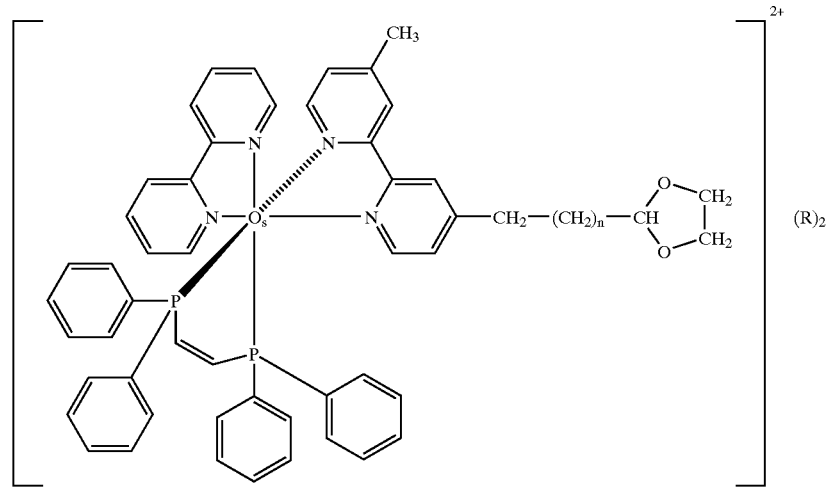

wherein R is an anion and n is an integer. In one embodiment of the invention, n is 2.

This compound may comprise a composition of matter having the structure

$$X-(Y)_n-Z$$

wherein X represents one or more nucleotides which may be the same or different, one or more amino acids which may be the same or different, an antibody, an analyte of interest or an analogue of an analyte of interest, n represents an integer, and Z represents the compound provided by this invention.

The invention further provides a compound having the structure

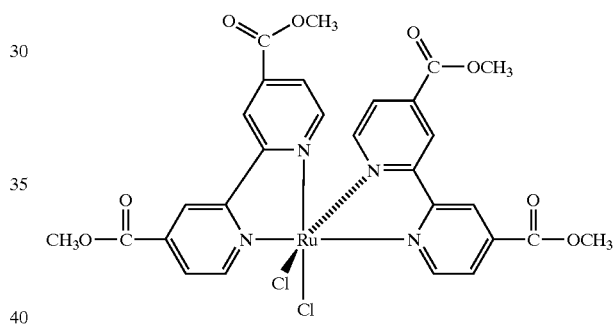

Also, the invention provides a compound having the structure

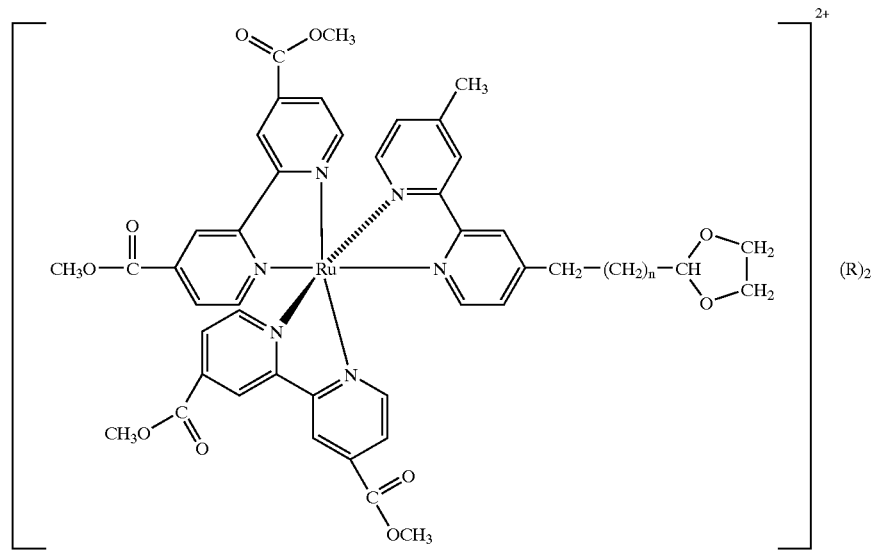

wherein R is an anion and n is an integer. In one embodiment of the invention, n is 2.

This compound may comprise a composition of matter having the structure

wherein X represents one or more nucleotides which may be the same or different, one or more amino acids which may be the same or different, an antibody, an analyte of interest or an analogue of an analyte of interest, n represents an integer, and Z represents the compound provided by this invention.

The invention further provides a compound having the structure

In another embodiment of the invention Z is bis(2,2'-bipyridine)[4-(butan-1-al)-4'methyl-2,2'-bipyridine]ruthenium (II).

In yet another embodiment of the invention, the thymidine nucleotide is a 3' terminal nucleotide attached to the nucleotide sequence

TCACCAATAAACCG CAAACACCATCCC7; TCCTG CCAG

Also provided is a composition of matter having the structure $[T-Y-Z]^{2+}(R)_2$ wherein T represents theophylline, Y represents a linker group attaching T to Z, Z represents bis-(2,2'-bipyridine)[4-methyl-2,2'-bipyridine-4'-yl]ruthenium (II) and R represents an anion.

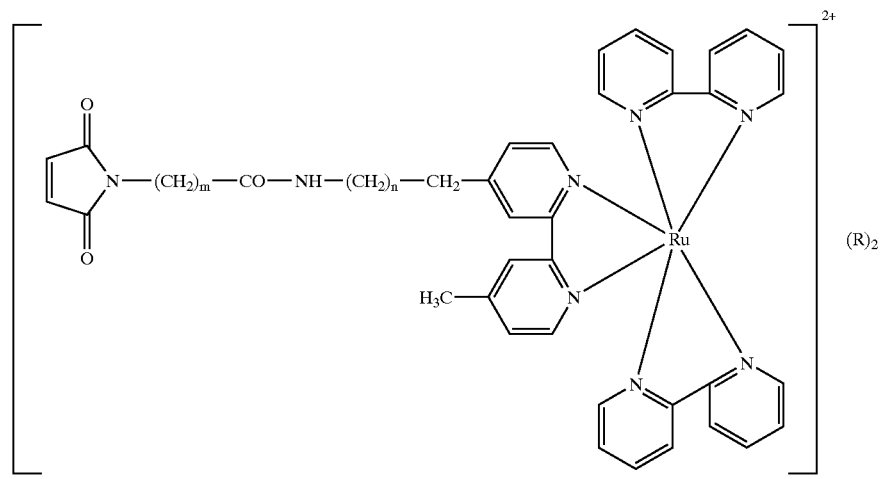

wherein R is an anion and m and n are integers. In one embodiment of the invention, m is 5 and n is 3.

This compound may comprise a composition of matter having the structure

wherein X represents one or more nucleotides which may be the same or different, one or more amino acids which may be the same or different, an antibody, an analyte of interest or an analogue of an analyte of interest, n represents an integer, and Z represents the compound provided by this invention. In one embodiment of the invention, X is theophylline. In another embodiment of the invention, X is digoxigenin. In a further embodiment of the invention, X is a peptide derived from hCG.

Also provided by the invention is a composition of matter having the structure

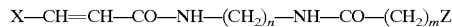

wherein:
  X represents one or more nucleotides which may be the same or different;
  Z represents an electrochemiluminescent chemical moiety;
  n represents an integer greater than or equal to 1; and
  m represents an integer greater than or equal to 1.

In one embodiment of the invention, X is thymidine attached to CH at carbon 5, n is 7 and m is 3.

In one embodiment of the invention, Y is attached to the carbon at position 8 of T. In another embodiment of the invention, Y has the structure

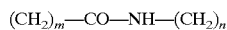

wherein m and n represent an integer, which may be the same or different, greater than or equal to 1. In another embodiment of the invention, m is 3 and n is 4. In another embodiment of the invention, m and n are both 3.

In yet another embodiment of the invention, Y has the structure

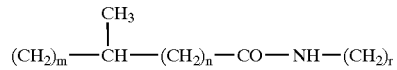

wherein m, n are r represent an integer, which may be the same or different, greater than or equal to 1. In one embodiment of the invention, m is 1, n is 1 and r is 4.

In still a further embodiment of the invention, Y has the structure

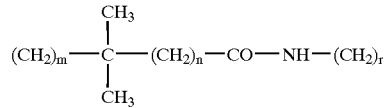

wherein m, n and r represent an integer, which may be the same or different, greater than or equal to 1. In one embodiment of the invention, m is 1, n is 1 and r is 4.

In yet another embodiment of the invention, Y is attached to the nitrogen at position 7 of T.

In one embodiment of the invention, Y has the structure

wherein n is an integer greater than or equal to 1. In still another embodiment of the invention, n is 4.

The invention further provides a compound having the structure

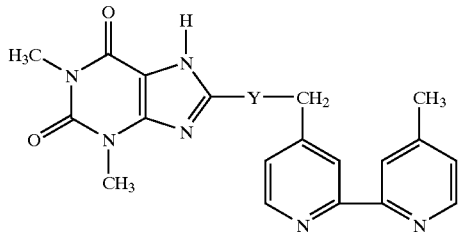

wherein Y is a linker arm. In one embodiment of the invention, Y has the structure

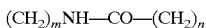

wherein m and n are integers, which may be the same or different, greater than or equal to 1.

In one embodiment of the invention, m is 3 and n is 2.

The invention also provides a compound having the structure

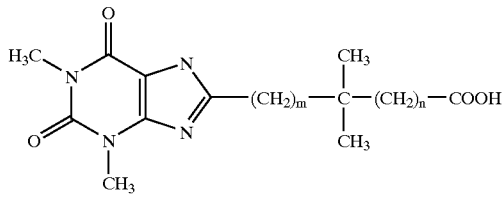

wherein m and n are integers which may be the same or different. In one embodiment of the invention, m and n are both 1.

Further provided is a composition of matter having the structure

wherein X represents one or more amino acids which may be the same or different, comprising at least one amino acid which is cysteine or methionine, and Z is bis (2,2'-bipyridine)maleimidohexanoic acid, 4-methyl-2,2'-bipyridine-4'-butylamide ruthenium (II) attached by the carbon at position 3 or 4 of the maleimide to a sulfur substituent of cysteine or methionine.

The following examples are provided to illustrate, but in no way limit, the present invention, which is defined by the claims which follow the specification.

EXAMPLE 1

Electrochemiluminescence in Various Organic Solvents

The electrochemiluminesence of tris(2,2'-bipyridyl) ruthenium (II) chloride hexahydrate was measured in a 15 ml three-neck, round bottom flask containing 10 ml of a solution prepared as described below; a 1.5 mm×10 mm magnetic stir bar; a 1.0 mm diameter silver wire quasi-reference electrode; a combination 28 gauge platinum wire counter electrode; and a working electrode consisting of a 22 gauge platinum wire welded to a 1 cm×1 cm square piece of 0.1 mm thick, highly polished platinum foil. (The working platinum foil electrode was shaped into a 3/16 of an inch diameter semi-circle surrounding the 28 gauge platinum wire counter electrode by 3/32 of an inch equidistantly.)

The silver wire was connected to the EG&G Model 178 electrometer probe of the EG&G Model 173 potentiostat/galvanostat. The platinum wire counter electrode and the platinum working electrode were connected to the anode and cathode respectively of the EG&G Model 173 potentiostat. The device was grounded.

Cyclic voltammetry was performed with the EG&G Model 173 potentiostat to which an EG&G Model 175 universal programmer was attached. The programmer was set for 100 mV/second sweeps between +1.75 volt anodic and −1.80 volt cathodic potentials. Electrochemiluminescence was detected using a Hamamatsu R928 photomultiplier tube, set inside a Products for Research Model PR1402RF photomultiplier tube housing which was fitted with a Kodak #23A gelatin (red) filter. The photomultiplier tube housing was connected to an Oriel Model 7070 photomultiplier detection system. The cyclic voltammogram was recorded on a Houston Instruments Model 200 X-Y recorder.

Cyclic voltammograms were generated for 1 mM tris(2, 2'-bipyridyl)ruthenium (II) chloride hexahydrate (Aldrich Chemical Company), 0.1M tetrabutylammonium tetrafluoroborate (TBABF$_4$) (Aldrich Chemical Company) solutions prepared with the following organic solvents: acetonitrile; n-dimethylformamide; dimethylsulfoxide 1-methyl, 2-pyrrolidinone (Aldrich Chemical Company). Tert-butyl alcohol and deionized, distilled water (1:1, v/v) also was used to make a solution containing 1 mM tris(2,2'-bipyridyl) ruthenium II chloride hexahydrate and 0.1 M TBABF$_4$. The resulting voltammograms did not indicate any change in the redox potential of the tris(2,2'-bipyridyl)ruthenium (II) chloride hexahydrate upon variation of the organic solvent.

For visual determination of electrochemiluminescence, solutions were prepared as follows: sufficient amounts of tris(2,2'-bipyridyl)ruthenium (II) chloride hexahydrate and TBABF$_4$ were dissolved in the spectroscopic grade organic solvents (Aldrich Chemical Company) described above to provide final concentrations of 1 mM and 0.1M, respectively. 10 ml of the resulting solution was then added to the 15 ml three-neck round bottom flask. The electrodes were immersed in the solution and the working electrode pulsed between a +1.75 and −1.45 volt potential to generate electrochemiluminescence. Electrochemiluminesence was visually observed in each of the solutions described above.

For quantitative measurements of the effect of solvent variation on electrochemiluminescence, solutions were prepared as follows: sufficient amounts of tris(2,2'-bipyridyl) ruthenium (II) chloride hexahydrate and TBABF$_4$ were added to the organic solvents described above to provide final concentrations of 2 mM and 0.2 M respectively. To an aliquot of this solution was added an equal volume of deionized, distilled water containing a strong oxidizing ammonium persulfate, at a concentration of 36 mM. Control solutions that did not contain the tris(2,2'-bipyridyl) ruthenium (II) chloride hexahyrate were prepared. 10 ml of the resulting solution was then added to the 15 ml three-neck round bottom flask. Electrochemiluminescence was accomplished by pulsing for one second intervals, between zero and −2.0 volts cathodic potential.

Electrochemiluminescent measurements were performed by integrating the resulting electrochemiluminescent photomultiplier tube signal using an integrator connected to a Micronta Model 22191 digital multimeter. The electrochemiluminescent signal was integrated for 10 seconds during the pulsing and recorded in millivolts. The results are shown in Table I and indicate that variation of solvents effects quantum efficiency of the ruthenium (II) chloride.

TABLE I

| Organic Solvent | Tris RuBiPy $10^{-6}$ M | Control | Δ |
|---|---|---|---|
| Acetonitrile | 2,540* | 104 | 2,436 |
| tert-butyl alcohol | 1,280 | 0 | 1,280 |
| N,N dimethyl-formamide | 2,390 | 143 | 2,247 |
| Dimethylsulfoxide | 2,760 | 29 | 2,731 |
| 1-methyl-2-pyrrolidinone | 1,630 | 0 | 1,630 |

*all measurements in millivolts.

EXAMPLE 2

Sensitivity of Detection of Electrochemiluminescence of Ruthenium-Labeled Rabbit Anti-Mouse Immunoglobulin G (IgG) Antibody The electrochemiluminescence of rabbit anti-mouse IgG antibody labeled with 4,4'-(dichloromethyl)-2,2'-bipyridyl, bis(2,2'-bipyridyl)ruthenium (II) (ruthenium-labeled rabbit anti-mouse IgG antibody) was measured in a 15 ml three-neck, round bottom flask containing 10 ml of a solution prepared as described below; a 1.5 mm×10 mm magnetic stir bar; a 1.0 mm diameter silver wire quasi-reference electrode; a combination 28 gauge platinum wire counter electrode, and a working electrode consisting of a 22 gauge platinum wire welded to a 1 cm×1 cm square piece of 0.1 mm thick, highly polished platinum foil. (The working platinum foil electrode was shaped into a 3/16 of an inch diameter semicircle surrounding the 28 gauge platinum wire counter electrode by 3/32 of an inch equidistantly.)

The silver wire was connected to the EG&G Model 178 electrometer probe of the EG&G Model 173 potentiostat/galvanostat. The platinum wire counter electrode and the platinum working electrode were connected to the anode and cathode respectively of the EG&G Model 173 potentiostat. The device was grounded.

The electrochemiluminescence emitted from the ruthenium-labeled rabbit anti-mouse IgG antibody solution was detected using an Hamamatsu R928 photomultiplier tube, set inside a Products for Research Model PR1402RF photomultiplier tube housing which was fitted with a Kodak #23A gelatin (red) filter. The photomultiplier tube housing was connected to an Oriel Model 7070 photomultiplier detection system.

Electrochemiluminescence was induced by pulsing for one second intervals, between zero and −2.0 volts cathodic potential. Electrochemiluminescent measurements were performed by integrating the resulting electrochemiluminescent photomultiplier tube signal using an integrator connected to a Micronta Model 22191 digital multimeter. The electrochemiluminescent signal was integrated for 10 seconds during the pulsing and recorded in millivolts.

A stock solution of $1.25\times10^{-7}$M ruthenium-labeled rabbit anti-mouse IgG antibody was prepared from a concentrated solution (2 mg/ml, 7.5 Ru/antibody) of the labeled antibody by dilution in phosphate-buffered saline (PBS). An aliquot of this solution (80 microliters) was added to 10 ml of dimethylsulfoxide (DMSO)/deionized, distilled water (1:1) containing 0.1 M tetrabutylammonium tetrafluoroborate (TBABF$_4$) and 18 mM ammonium persulfate in the reaction vessel. The final ruthenium-labeled antibody concentration was $1\times10^{-9}$M. Electrochemiluminescence was measured as described above.

Additional solutions representing various dilutions of the ruthenium-labeled rabbit anti-mouse IgG antibody stock solution were made and aliquots (80 microliters) of these solutions were added to the same solution of ruthenium-labeled antibody in the reaction vessel in increments which resulted in the following concentrations of labeled antibody: $5\times10^{-9}$M, $1\times10^{-8}$M, and $5\times10^{-8}$M. Electrochemiluminescence measurements were made for each solution as described. These measurements are listed in Table II below. These results indicate the sensitivity of electrochemiluminescent detection of labeled antibody ($1\times10^{-9}$M), and the dependence of the intensity of electrochemiluminescence on the concentration of the ruthenim-labled anti-mouse IgG antibody.

TABLE II

ELECTROCHEMILUMINESCENCE (ECL) OF RUTHENIUM-LABELED RABBIT ANTI-MOUSE IMMUNOGLOBULIN G (IgG) ANTIBODY

| Concentration of Ruthenium-Labeled Anti-Mouse IgG Antibody | ECL (mV) |
|---|---|
| $5\times10^{-8}$ M | 1610 |
| $1\times10^{-8}$ M | 892 |
| $5\times10^{-9}$ M | 418 |
| $1\times10^{-9}$ M | 72 |
| 0 | 0 |

EXAMPLE 3

Immunological Reactivity of Ruthenium-Labeled Bovine Serum Albumin (BSA) in a Solid Phase Enzyme Linked-Immunosorbent Assay (ELISA)

The wells of a polystyrene microtiter plate were coated with a saturating concentration of either bovine serum albumin labeled with 4,4'-(dichloromethyl)-2,2'-bipyridyl, bis(2,2'-bipyridyl)ruthenium (II), i.e. ruthenium-labeled bovine serum albumin, (6 Ru/BSA, micrograms/ml in PBS buffer, 50 microliters/well) or unlabeled BSA (20 micrograms/ml in PBS buffer, 50 microliters/well) and incubated for one hour at room temperature. After this incubation period the plate was washed three times with PBS, 5 minutes per wash. A solution containing 6 mg/ml rabbit anti-BSA antibody was diluted 1:20,000, 1:30,000, 1:40,000, 1:50,000, and 1:60,000 in PBS, and the dilutions were added in duplicate to the wells coated with ruthenium-labeled BSA or unlabeled BSA, and the plate was incubated for one hour at room temperature. After three washes with PBS as before, the presence of bound rabbit anti-BSA antibody was determined by adding goat anti-rabbit IgG-peroxidase conjugate (1:1000 dilution in PBS of a 0.5 mg/ml solution, 50 microliters/well) to each well and incubating the plate for one hour at room temperature. After washing the plate twice with PBS, 0.5% Tween-20, and twice with PBS as before, hydrogen peroxide (30%) and 2,2'-azino-di-[3-ethyl-benzthiazoline sulfonate] (KPL, Gaithersburg, Md.) were mixed in equal volumes and 200 microliters were added to each well of the plate. After a 30 minute incubation at room temperature, the plate was read spectrophotometrically at 414 nm. The mean background absorbence in the control wells was subtracted from the mean value of duplicate readings for each dilution of the rabbit anti-BSA antibody that was added to the wells coated with ruthenium-labeled BSA or unlabeled BSA. These corrected absorbence values are shown in Table V.

The curves obtained for the unlabeled BSA and ruthenium-labeled BSA were parallel, with corrected absorbance values at each point on the two curves at a constant ratio, approximately 0.6. Identical results were obtained for two other lots of ruthenium-labeled BSA which were made using the same activated ruthenium complex as described previously, and which had similar Ru/BSA labeling ratios. These results indicate that the ruthenium-labeled BSA is immunologically reactive and that it retains approximately 60% of its immunoreactivity when labeled with ruthenium in comparison to unlabeled BSA.

TABLE III

ABSORBANCE AT 414 nm

| Rabbit Anti-BSA Antibody Dilution | Unlabeled BSA | Ruthenium-labeled BSA | Relative Immunoreactivity |
|---|---|---|---|
| 20,000 | 1.06 | 0.66 | 62% |
| 30,000 | 0.83 | 0.50 | 60% |
| 40,000 | 0.67 | 0.40 | 60% |
| 50,000 | 0.56 | 0.33 | 59% |
| 60,000 | 0.47 | 0.28 | 60% |

EXAMPLE 4

Immunological Reactivity of Ruthenium-Labeled Rabbit Anti-Mouse Immunoglobulin (IgG) Antibody by a Competitive Solid Phase Enzyme Linked-Immunosorbent Assay (ELISA)

Rabbit anti-mouse IgG antibody labeled with 4,4'-(dichloromethyl)-2,2'-bipyridyl, bis(2,2'-bipyridyl) ruthenium (II) (ruthenium-labeled rabbit anti-mouse IgG antibody) was compared with unlabeled rabbit anti-mouse IgG antibody with respect to its ability to compete with enzyme-labeled, anti-mouse IgG antibody for binding to mouse IgG. The wells of a 96-well polystyrene microtiter plate were coated with a solution of mouse IgG (5 micrograms/ml in PBS buffer), incubated for 60 minutes at room temperature and washed three times, 5 minutes per wash, with PBS. Two solutions were prepared, one containing a mixture of rabbit anti-mouse IgG-alkaline phosphatase conjugate and rabbit anti-mouse IgG (1 mg/ml), and the other a mixture of rabbit anti-mouse IgC-alkaline phosphatase conjugate and ruthenium-labeled rabbit anti-mouse IgG (1 mg/ml, 7.5 Ru/antibody). These two solutions, and a third containing rabbit anti-mouse IgG-alkaline phosphatase conjugate, were diluted 1:6000, 1:7000, 1:8000, 1:9000, 1:10,000, 1:12,000, 1:14,000 and 1:16,000 in PBS containing 0.5% Tween-20, and added (50 microliters/well) to separate rows of the plate containing bound mouse IgG. The plate was incubated for 60 minutes at room temperature and washed twice with PBS-Tween-20 and twice with PBS, 5 minutes per wash. The enzyme substrate p-nitrophenyl phosphate (1.5 mg/ml in 10% diethanolamine buffer, pH 9.6) was added to each well (200 microliters/well); the plate was incubated for 30 minute's at room temperature and read spectrophotometrically at 405 nm. The mean background absorbance in the control wells was subtracted from the mean value of duplicate readings for each of the three solutions at each dilution. These absorbance values are shown in Table IV.

Three obtained, the top curve representing the uninhibited binding of the enzyme conjugate, and the two lower curves representing inhibition by ruthenium-labeled anti-mouse IgG and unlabeled anti-mouse IgG. The ruthenium-labeled, antimouse IgG curve, on a point-by-point comparison, is approximately 81% as low as the unlabeled anti-mouse IgG curve in comparison to the enzyme conjugate curve. These results indicate that the ruthenium-labeled, anti-mouse IgG antibody is immunologically reactive for its antigen (mouse IgG), and is approximately 81% as effective as unlabeled anti-mouse IgG antibody in competing with enzyme-labeled, anti-mouse IgG antibody for binding to mouse IgG.

TABLE IV

ABSORBANCE AT 405 nm

| Dilution | A<br>Anti-Mouse IgG Alkaline Phosphatase (Enzyme Conjugate) | B<br>Enzyme Conjugate + Ruthenium Labeled Anti-Mouse IgG | C<br>Enzyme Conjugate + Unlabeled Anti-Mouse IgG | Comparative* Degree of Inhibition |
|---|---|---|---|---|
| 6,000 | 1.48 | 0.94 | 0.79 | 77% |
| 7,000 | 1.33 | 0.82 | 0.69 | 79% |
| 8,000 | 1.21 | 0.72 | 0.62 | 82% |
| 9,000 | 1.10 | 0.65 | 0.56 | 84% |
| 10,000 | 1.01 | 0.60 | 0.51 | 82% |
| 12,000 | 0.87 | 0.51 | 0.43 | 80% |
| 14,000 | 0.77 | 0.45 | 0.37 | 81% |
| 16,000 | 0.68 | 0.40 | 0.33 | 80% |

*(A − B/A − C) × 100%

EXAMPLE 5

Electrochemiluminescence of Ruthenium-Labeled Bovine Serum Albumin (BSA)

A solution containing $7.8 \times 10^{-6}$ M bovine serum albumin (BSA) labeled with 4,4'-(dichloromethyl)-2,2'-bipyridyl, bis (2,2'bipyridyl)ruthenium (II) (ruthenium-labeled bovine serum albumin) was prepared from a stock solution of ruthenium-labeled BSA (2.6 mg/ml, 6 Ru/BSA) by dilution in phosphate-buffered saline. 26 microliters of this solution were added to 10 ml of DMSO/deionized, distilled water (1:1) containing 0.1 M $TBABF_4$ and 18 mM ammonium persulfate in the reaction vessel. The final ruthenium-labeled BSA concentration was $2 \times 10^{-8}$M. Electrochemiluminescence was measured as described in Example V.

In an analogous manner, a solution containing $7.8 \times 10^{-6}$M unlabeled BSA was prepared and added to the reaction vessel to give a final unlabeled BSA concentration of $2 \times 10^{-8}$M. The electrochemiluminescence of this solution and of a similar solution without BSA was measured. Electrochemiluminescence measurements are shown in Table V for covalently coupled, ruthenium-labeled BSA and unlabeled BSA.

TABLE V

ELECTROCHEMILUMINESCENCE (ECL) OF RUTHENIUM-LABELED BSA

| Solution | ECL (mV) |
|---|---|
| $2 \times 10^{-8}$ M Ruthenium-Labeled BSA | 730 |
| $2 \times 10^{-8}$ M BSA | 100 |
| DMSO:$H_2O$ (1:1) | 0 |

EXAMPLE 6

Electrochemiluminescence of Ruthenium-Labeled Rabbit Anti-Mouse Immunoglobulin G (IgG) Antibody A solution containing $1.25 \times 10^{-6}$ M rabbit anti-mouse IgG antibody labeled with 4,4'-(dichloromethyl)-2,2'-bipyridyl, bis(2,2'-bipyridyl)ruthenium (II) (ruthenium-labeled, rabbit anti-mouse IgG antibody) was prepared from a stock solution of ruthenium-labeled, rabbit anti-mouse IgG antibody (2 mg/ml, 7.5 Ru/antibody) by dilution in phosphate-buffered saline. 80 microliters of this solution were added to 10 ml of DMSO/deionized, distilled water (1:1) containing 0.1M $TBABF_4$ and 18 mM ammonium persulfate in the reaction vessel. The final ruthenium-labeled antibody concentration was $1 \times 10^{-8}$M. Electrochemiluminescence was measured as described in Example 2.

In an analogous manner, a solution containing $1.25 \times 10^{-6}$M unlabeled, rabbit anti-mouse IgG antibody was prepared and added to the reaction vessel to give a final unlabeled antibody concentration of $1 \times 10^{-8}$M. The electrochemiluminescence of this solution and of the solution without added antibody was also measured as described. Electrochemiluminescent measurements are shown in Table VIII for covalently-coupled, ruthenium-labeled rabbit anti-mouse IgG antibody and unlabeled rabbit anti-mouse IgG antibody.

TABLE VI

ELECTROCHEMILUMINESCENCE (ECL) OF RUTHENIUM-LABELED RABBIT ANTI-MOUSE IMMUNOGLOBULIN G (IgG) ANTIBODY

| Solution | ECL (mV) |
|---|---|
| $1 \times 10^{-8}$ M Ruthenium-Labeled Rabbit Anti-Mouse IgG Antibody | 892 |
| $1 \times 10^{-8}$ M Rabbit Anti-Mouse IgG Antibody | 0 |
| DMSO:$H_2O$ (1:1) | 0 |

EXAMPLE 7

Homogeneous Electrochemiluminescent Immunoassay for Antibody to Bovine Serum Albumin A solution containing $7.8 \times 10^{-6}$M bovine serum albumin (BSA) labeled with 4,4'-dichloromethyl-)-2,2'bipyridyl, bis(2,2'-bipyridyl)ruthenium (II) (ruthenium-labeled bovine serum albumin) was prepared from a stock solution of ruthenium-labeled BSA (2.5 mg/ml, 6 Ru/BSA) by dilution in phosphate-buffered saline (PBS). 26 microliters of this solution were added to 10 ml of DMSO/deionized, distilled water (1:1) containing 0.1M $TBABF_4$ and 18 mM ammonium persulfate in the reaction vessel. The final ruthenium-labeled BSA concentration was $2 \times 10^{-8}$M. Electrochemiluminescence was measured as described in Example 2.

In an analogous manner, a solution containing $7.8 \times 10^{-6}$M unlabeled BSA was prepared and added to the reaction vessel to give a final unlabeled BSA concentration of $5 \times 10^{-8}$M. The electrochemiluminescence of this solution and of a similar solution without BSA were measured.

A solution containing $3.75 \times 10^{-5}$M rabbit anti-BSA antibody was prepared from a stock solution of rabbit anti-BSA antibody (6.0 mg/ml) by dilution in PBS, and an aliquot (26 microliters) was added to the solution of ruthenium-labeled BSA in the reaction vessel to give a final rabbit anti-BSA antibody concentration of $1 \times 10^{-7}$M.

The electrochemiluminescence of the resulting mixture of ruthenium-labeled BSA antigen and antibody (rabbit anti-BSA) was measured. The results shown in Table VII indicate a reduction in the electrochemiluminescence of the ruthenium-labeled BSA upon addition of rabbit anti-BSA antibody and demonstrate that a homogeneous electrochemiluminescent detection of antibody to BSA may be achieved. Based upon these results one skilled in the art would know that a homogeneous electrochemiluminescent immunoassay for detecting other analytes of interest may be developed.

TABLE VII

REDUCTION OF ELECTROCHEMILUMINESCENCE (ECL) OF RUTHENIUM-LABELED BOVINE SERUM ALBUMIN UPON BINDING OF ANTIBODY

| UNLABELED BSA (CONTROL) | RUTHENIUM-LABELED BSA (ANTIGEN) | RABBIT ANTI-BSA (ANTIBODY) | ECL (mV) |
|---|---|---|---|
| 0 | $2 \times 10^{-8}$ M | 0 | 727 |
| 0 | $2 \times 10^{-8}$ M | $1 \times 10^{-7}$ M | 92 |
| $2 \times 10^{-8}$ M | 0 | 0 | 94 |

EXAMPLE 8

Homogeneous Electrochemiluminescent Immunoassay for Mouse Immunoglobulin G (IgG)

A solution containing $6.25 \times 10^{-6}$M rabbit anti-mouse IgG antibody labeled with 4,4'-(dichloromethyl)-2,2'-bipyridyl, bis(2,2'-bipyridyl)ruthenium (II) (ruthenium-labeled rabbit anti-mouse IgG antibody) was prepared from a stock solution of ruthenium-labeled rabbit anti-mouse IgG antibody (2 mg/ml, 7.5 Ru/antibody) by dilution in phosphate-buffered saline (PBS). 80 microliters of this solution were added to 10 ml of DMSO/deionized, distilled water (1:1) containing 0.1M $TBABF_4$ and 18 mM ammonium persulfate in the reaction vessel. The final ruthenium-labeled antibody concentration was $5 \times 5 \: 10^{-8}$M. Electrochemiluminescence was measured as described in Example 2.

In an analogous manner, a solution containing $6.25 \times 10^{-6}$M unlabeled rabbit, anti-mouse IgG antibody was prepared and added to the reaction vessel to give a final unlabeled antibody concentration of $5 \times 10^{-8}$M. The electrochemiluminescence of this solution and of a similar solution without antibody were measured.

A solution containing $2.5 \times 10^{-5}$M mouse IgG was prepared from a stock solution of mouse IgG (4.0 mg/ml) by dilution in PBS, and different aliquots (20 microliters and 40 microliters) of this solution were added to the solution of ruthenium-labeled, anti-mouse IgG antibody in the reaction vessel to give final mouse IgG concentrations of $5\times10^{-8}$M and $1\times10^{-7}$M, respectively.

Figure 1:
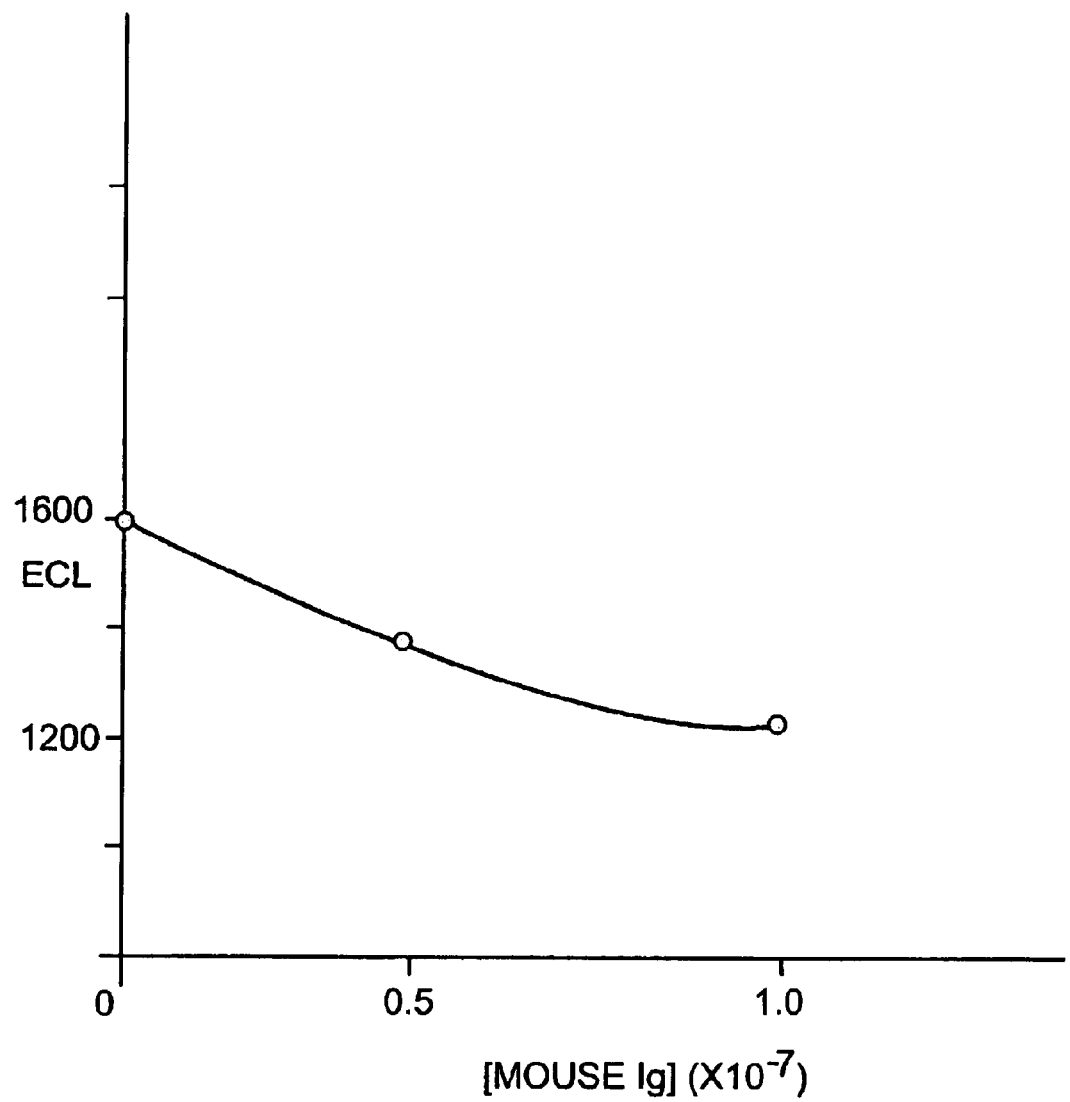
FIG. 1 depicts electrochemiluminescent measurements made for a homogeneous immunoassay for the determination of the concentration of an antigen in solution.

The electrochemiluminescence of the resulting mixture of ruthenium-labeled, anti-mouse IgG antibody and the antigen (mouse IgG) was measured. The results are shown in Table VIII. The dependence of the electrochemiluminescence measurements upon the concentration of the mouse IgG antigen is shown in FIG. 1. These results demonstrate a reduction in the electrochemiluminescence of the ruthenium-labeled antibody upon addition of antigen. Based upon these results one skilled in the art would know that a homogeneous electrochemiluminescent immunoassay for determining the concentration of other analytes of interest may be developed.

TABLE VIII

REDUCTION OF ELECTROCHEMILUMINESCENCE (ECL) OF RUTHENIUM-LABELED ANTIBODY UPON BINDING OF ANTIGEN

| UNLABELED ANTI-MOUSE IgG (CONTROL) | RUTHENIUM-LABELED ANTI-MOUSE IgG (ANTIBODY) | MOUSE IgG (ANTIGEN) | ECL (MV) |
|---|---|---|---|
| 0 | $5 \times 10^{-8}$ M | 0 | 1610 |
| 0 | $5 \times 10^{-8}$ M | $5 \times 10^{-8}$ M | 1360 |
| 0 | $5 \times 10^{-8}$ M | $5 \times 10^{-7}$ M | 1240 |
| $5 \times 10^{-8}$ M | 0 | 0 | 0 |

EXAMPLE 9

Heterogeneous Electrochemiluminescent Immunoassay for Legionella Using a Mouse Anti-Legionella Immunoglobulin G (IgG) Antibody and Ruthenium-Labeled Rabbit Anti-Mouse Immunoglobulin G (IgG Antibody)

A formalinized suspension of the bacterium Legionella micdadei was adjusted to an optical density (at 425 nm) of 1.00 by dilution with PBS buffer. Approximately $3\times10^9$ cells were added to a conical microcentrifuge tube. The cells were centrifuged (10 minutes, 10,000 RPM), the supernatant decanted, and the cells resuspended in a 1:50 dilution of a mouse monoclonal IgG antibody, (1.45 mg/ml) specific for Legionella micdadei, in PBS (1 ml). After incubation at room temperature for 1 hour, the cells were centrifuged, the supernatant decanted, the cells resuspended in PBS buffer and centrifuged again. Following decantation of the supernatant, the cells were resuspended in a 1:50 dilution (in PBS) of rabbit anti-mouse IgG antibody labeled with 4,4'-(dichloromethyl)-2,2'-bipyridyl, bis(2,2'-bipyridyl)ruthenium (II) i.e. ruthenium-labeled rabbit anti-mouse IgG antibody, (2 mg/ml, 7.5 Ru/antibody). After incubation at room temperature for 1 hour, the cells were centrifuged, the supernatant decanted, and the cells resuspended in PBS and washed twice, with centrifugation, as before. Following the last wash the cells were resuspended in 200 microliters of PBS. 100 microliters of the cell suspension was added to the reaction vessel containing 10 ml of DMSO/deionized, distilled water (1:1) containing 0.1 M TBABF$_4$ and 18 mM ammonium persulfate and transferred to the reaction vessel. The electrochemiluminescence was measured for the cell suspension. Another 100 microliters of the cell suspension was added to the reaction vessel and electrochemiluminescence measured. Electrochemiluminescence was measured for the solution without cells as a control according to the method described in Example 2. The results shown in Table IX indicate a heterogeneous electrochemiluminescent immunoassay for Legionella using ruthenium-labeled rabbit anti-mouse IgG antibody has been successfully carried out.

TABLE IX

HETEROGENEOUS ELECTROCHEMILUMINESCENT (ECL) IMMUNOASSAY FOR LEGIONELLA MICDADEI

| Sample | ECL (mV) |
|---|---|
| Legionella micdadei cell suspension, $1.9 \times 10^9$ cells in DMSO/H$_2$O (1:1) | 160 |
| Legionella micdadei cell suspension, $9.3 \times 10^8$ cells in DMSO/H$_2$O (1:1) | 90 |
| DMSO:H$_2$O (1:1) | 0 |

EXAMPLE 10

Homogeneous Electrochemiluminescent Immunoassay for Legionella Using a Mouse Anti-Legionella Immunoglobulin G (IgG) Antibody and Ruthenium-Labeled Rabbit Anti-Mouse Immunoglobulin G (IgG) Antibody A suspension of the bacterium Legionella micdadei was prepared and incubated with a mouse monoclonal IgG antibody specific for Legionella as described in Example 9. The cells were centrifuged, washed, and resuspended in 0.2 ml of PBS. An aliquot (80 microliters) of rabbit, anti-mouse IgG antibody labeled with 4,4'-(dichloromethyl)-2,2'-bipyridyl, bis(2,2'-bipyridyl)ruthenium (II), i.e. ruthenium-labeled rabbit anti-mouse IgG antibody ($1.25\times10^{-6}$M) was added to the cell suspension, and the mixture was incubated for 2 hours at room temperature. As a control, an identical dilution of ruthenium-labeled, rabbit anti-mouse IgG antibody was incubated in the same way in the absence of the cell suspension. After the incubation period, the solution of labeled antibody was added to 10 ml of DMSO/deionized, distilled water (1:1) containing 0.1 m TBABF$_4$ and 18 mM ammonium persulfate in the reaction vessel to give a final ruthenium-labeled, rabbit anti-mouse IgG antibody concentration of $1\times10^{-8}$M. The electrochemiluminescence was measured as described in Example 2. The same procedure was followed for the cell suspension with added ruthenium-labeled rabbit anti-mouse IgG antibody. The results, shown in Table X, indicate a reduction of the electrochemiluminescent emission upon the interaction of ruthenium-labeled, anti-mouse IgG antibody with mouse monoclonal antibody bound to Legionella and that a homogeneous electrochemiluminescent immunoassay for Legionella micdadei has been successfully carried out.

TABLE X

HOMOGENEOUS ELECTROCHEMILUMINESCENT (ECL) IMMUNOASSAY FOR LEGIONELLA MICDADEI

| SAMPLE | ECL (mV) |
|---|---|
| $1 \times 10^{-8}$ M Ruthenium-Labeled Anti-mouse IgG Antibody | 976 |
| $1 \times 10^{-8}$ M Ruthenium-Labeled Anti-Mouse IgG Antibody + Monoclonal Antibody Bound To Legionella micdadei | 803 |
| DMSO:H$_2$O (1:1) | 0 |

EXAMPLE 11

Increase in Electrochemiluminescence Upon a Release of a Ruthenium-Labeled Antibody Bound to Bacteria A formalinized suspension of the bacterium *Legionella micdadei* was adjusted to an optical density (at 425 nm) of 1.00 by dilution with PBS buffer and 2 ml of this suspension were added to a conical microcentrifuge tube. The cells were centrifuged (10 minutes, 10,000 RPM), the supernatant decanted, and the cells were resuspended in a 1:10 dilution in PBS (0.5 ml) of a mouse monoclonal IgG antibody, (1.45 mg/ml) specific for *Legionella micdadei*. After incubation at room temperature for 1 hour, the cells were centrifuged as before, the supernatant was decanted, the cells were resuspended in PBS buffer and centrifuged again. Following decantation of the supernatant, the cells were resuspended in a 1:50 dilution (in PBS) of ruthenium-labeled, rabbit anti-mouse IgG antibody (1 ml, 7.5 Ru/antibody). After incubation at room temperature for 1 hour, the cells were centrifuged as before, the supernatant was decanted, and the cells resuspended in PBS and washed twice, with centrifugation as before. Following the last wash the cells were resuspended in 100 microliters of either PBS or 1.0M acetic acid—0.9% NaCl (normal saline) solution and incubated at room temperature for 40 minutes. After centrifugation, 100 microliters of the cell supernatant fluid was transferred into the reaction vessel along with 10 ml of DMSO-deionized, distilled water (1:1) containing 0.1 M TBABF$_4$ and 18 mM ammonium persulfate. The electrochemiluminescence of the acetic acid/normal saline cell supernatant fluid and for the supernatant fluid from the PBS washed cells was measured according to the method described in Example 2. The electrochemiluminescence measurements are shown in Table XI, and demonstrate that the elution of the ruthenium-labeled, rabbit anti-mouse IgG from the monoclonal antibody coated *Legionella* bacteria by treating the cells with 1.0 m acetic acid-normal saline (Ref 0.23) results in an increase in the electrochemiluminescence generated by the unbound ruthenium-labeled antibody. These results also show that the ruthenium labeled antibody is bound to the monoclonal antibody-coated *Legionella*, and that the PBS wash did not result in an increase in ECL in comparison to the background signal.

TABLE XI

ELECTROCHEMILUMINESCENCE (ECL) OF SUPERNATANT FLUIDS OF CELLS COATED WITH RUTHENIUM-LABELED ANTI-MOUSE IMMUNOGLOBULIN (IgG)

| Solution | ECL (mV) |
| --- | --- |
| Background control: 100 microliters 1.0 M acetric acid-normal saline | 134 |
| 100 microliters of PBS cell wash supernatant fluid | 121 |
| 100 microliters of 1.0 M acetic acid-normal saline solution cell wash supernatant fluid | 214 |

EXAMPLE 12

Homogeneous Competitive Immunoassay for Pregnane-diol-3 Glucuronide (PD3G) in Urine Pregnane-diol-3-glucuronide (PD3G) may be detected and quantified in urine by contacting a sample of urine with a known amount of PD3G labeled with an electrochemiluminescent moiety and a known amount of an anti-PD3G antibody under conditions such that the PD3G present in the sample and the PD3G-electrochemiluminescent moiety compete for binding sites on the antibody. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of PD3G present in the sample determined therefrom.

EXAMPLE 13

Labeling Nucleic Acids with a tris-Ruthenium bipyridyl-n-hydroxysuccinimide ester Nucleic acid samples (5 to 25 micrograms) in 10 mM tris hydrochloride (pH 8.0)-1 mM EDTA may be heat denatured, cooled and modified by bisulphite catalysed transamination of cytosine residues with ethylenediamine for three hours at 42° C. After overnight dialysis against three changes of 5 mM sodium phosphate buffer, pH 8.5, the samples may be concentrated to 100 microliters by ultrafiltration. These modified nucleic acids (1 to 10 micrograms) may be diluted in 100 microliters with 0.1 M sodium phosphate buffer, pH 8.5.

A tris-ruthenium bipyridyl-N-hydroxysuccinimide ester derivative may be prepared as a 0.2M stock solution in N,N'dimethylformamide (DMF) by methods known in the art. 5 microliters of this ester solution may be added to the modified nucleic acid solution in 0.1 M sodium phosphate buffer, pH 8.5 and incubated at room temperature for 1 hour. Labeled nucleic acid probes may be purified by dialysis against at least three changes of 150 mM sodium chloride—10 mm sodium phosphate buffer (pH 7.0) stored at 4° C. until used.

EXAMPLE 14

Nucleic Acid Hybridization Assay for Human T-Cell Leukemia III Virus (HTV-III) in Blood HTLV-III virus may be detected in whole blood by treating the blood to release the RNA from virus particles. A sample containing the HTLV-III RNA is contacted with a single-stranded oligonucleotide probe complementary to the HTLV-III RNA and labeled with an electrochemiluminescent moiety. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of HTLV-III RNA present in the sample determined therefrom.

EXAMPLE 15

Homogeneous Nucleic Acid Hybridization Assay for *Legionella* Bacteria in a Clinical Sample

*Legionella* bacteria may be detected in a clinical sample such as sputum by treating the sputum to release the ribosomal RNA from the bacteria. The resulting sample is contacted with a single-stranded oligonucleotide probe that is complementary to sequences in the ribosomal RNA, specific for *Legionella*, and labeled with an electrochemiluminescent moiety. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of *Legionella* Bacteria present in the sample determined therefrom.

EXAMPLE 16

Hybridization Assay for the Detection of Cytomegalovirus DNA Integrated into Genomic DNA by Strand Displacements Method Cytomegolavirus (CMV) DNA may be detected in human genomic DNA by treating a tissue sample, for example lymphocytes, to release the DNA and cleaving the DNA with restriction enzymes. The resulting sample containing double-stranded fragments of CMV is contacted with a single-stranded oligonucleotide probe that is complementary to the CMV DNA, labeled with a electrochemiluminescent moiety and capable of displacing one of the strands of the DNA duplex. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of Cytomegalovirus RNA present in the sample determined therefrom.

EXAMPLE 17

Hydrization Assay for the Detection of the Ras-Oncogene in Human Bladder Carcinoma Cells Using a Heterogeneous Method The ras-oncogene may be detected in human bladder carcinoma cells by treating a tissue sample to release the DNA, cleaving the DNA with restriction enzymes, melting the DNA to single strands and binding to nitrocellulose paper as previously described in Maniatis, T. et al. (24). The filter paper with bound single-stranded DNA is contacted with an oligonucleotide probe specific for the ras-oncogene, and labeled with a electrochemiluminescent moiety. After a suitable reaction time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be detected and the presence of ras-oncogene RNA in the sample determined.

EXAMPLE 18

An Electrochemiluminescent Polymer-Based Enzyme Assay

A macromolecular enzyme substrate, for example starch, dextran or a synthetically prepared macromolecular polymer, may be labeled with an electrochemiluminescent moiety. The labeled substrate may be used to determine and quantify the presence of an enzyme present in a multicomponent system. The labeled substrate may also be used to quantify an amount of enzyme linked to an antibody, DNA probe, RNA probe, streptavidin, avidin, or bioti. The labeled substrate may be cleaved into smaller fragments selectively by an appropriate enzyme. Any enzyme-substrate combination may be used. Examples of enzymes include glycosidases, glucosidases, amylases, proteases, endonucleases, lyases and dextranases. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of enzyme present in the sample determined therefrom. The advantage is that an amplification of the electrochemiluminescent signal will result from the cleaved fragments each labeled with electrochemiluminescent moiety.

EXAMPLE 19

Detection of *Streptococci* by an Electrochemiluminescent Enzyme Assay

A sample containing *streptococci* may be contacted with a reagent mixture containing a synthetic peptide labeled with an electrochemiluminescent moiety. The synthetic peptide being a substrate specific for a peptidase produce by the bacteria. Action of the peptidase on the synthetic peptide results in the production of fragments labeled with the electrochemiluminescent moiety. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of *streptococci* present in the sample determined therefrom.

EXAMPLE 20

Enzyme Immunoassay for Hepatitis B Surface Antigen Based on Electrochemiluminescence A blood sample containing Hepatitis B surface antigen (HBsag) is contacted for a suitable time with an antibody specific for the HBsag and labeled with dextranase. The antibody not bound to HBsag is removed and the antigen-antibody complex is contacted with a dextran polymer labeled with an electrochemiluminescent moiety. Action of the dextranase on the labeled polymers will result in the production of fragments each labeled with the electrochemiluminescent moiety. After a suitable time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of Hepatitis B surface antigen present in the sample determined therefrom.

EXAMPLE 21

Homogeneous Assay for Bradykinin Receptors Using an Electrochemiluminescent-labeled Bradykinin A tissue sample containing bradykinin receptors is suitably prepared and contacted with bradykinin labeled with an electrochemiluminescent moiety. After a suitable amount of time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of bradykinin receptor present in the sample determined therefrom. This assay could also be used for measuring other ligand-receptor interactions such as estrogen-estrogen receptor. In addition this assay may be used to determine and quantify the amount of unlabeled ligands using a competitive binding assay format.

EXAMPLE 22

Use of an Electrochemiluminescent Moiety for Detecting Nucleic Acid Hybrids

A sample containing nucleic acid hybrids, such as double-stranded DNA, DNA-RNA duplexes, or double-stranded RNA is contacted with an electrochemiluminescent moiety that specifically intercalates into nucleic acid hybrids. After a suitable amount of time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of nucleic acid hybrids present in the sample determined therefrom.

EXAMPLE 23

Detection of Human T-Cell Leukemia Virus III (HTLV-III) Antigen Complexed to Antibody in Saliva by a Homogeneous Immunoassay Using Electrochemiluminescence A saliva sample containing HTLV-III complexed to antibody is contacted with a solution containing a chaotopic agent to disrupt the antigen-antibody complexes. This solution is then contacted with an antibody specific for HTLV-III and labeled with an electrochemiluminescent moiety. The chaotopic agent is removed allowing the labeled and unlabeled antibodies to recombine with antigen. After a suitable amount of time the resulting sample may be induced to repeatedly emit electromagnetic radiation upon direct exposure to an electrochemical energy source effective for inducing the electrochemiluminescent moiety to repeatedly emit electromagnetic radiation. Emitted radiation may be quantified, and the amount of human T-cell leukemia virus III (HTLV-III) antigen present in the sample determined therefrom. These methods are applicable to samples containing other types of antigen-antibody complexes such as hepatitis antigen-antibody complexes, cytomegalovirus-antibody complexes, and non-A, non-B hepatitis-antibody complexes in serum.

EXAMPLE 24

Immunoassay for the Detection and Identification of a Multiplicity of *Staphylococcal* Enterotoxins Monoclonal antibodies specific for each of the *Staphylococcal* enterotoxins A, B, C, D, and E and monoclonal antibodies which are cross-reactive for these enterotoxins were purified. Each antibody was purified from ascitic fluid by passage of the ascites through a column of *Staphylococcal* protein A coupled to an agarose gel support matrix which is provided with binding, elution, and regeneration buffers as part of the Monoclonal Antibody Purification System (Bio-Rad Laboratories, Inc.). In the purification procedure, 2 ml of ascitic fluid typically containing 5–15 mg of monoclonal antibody per milliliter, were prefiltered by placing a Metricell membrane filter (Gelman Sciences, Inc.) between two F-13 analytical papers (Schleicher and Schuell, Inc.) in the bottom of a 10 ml syringe (Becton Dickenson, Inc.), introducing the ascitic fluid into the syringe, inserting the plunger, end filtering the ascitic fluid into a collection vessel. The filtrate was mixed with an equal volume of the binding buffer and applied to a 5 ml protein A-agarose column. The column reagent reservoir was then filled with the binding buffer to begin the elution process. The effluent was monitored for absorbance at 280 nm ($A_{280}$), and 1 ml fractions were collected. When the $A_{280}$ had returned to a stable baseline value, the column was washed with 5 bed volumes of binding buffer, and the elution buffer was then used to elute the purified immunoglobulin from the column. To neutralize the immunoglobulin, the eluate was collected in 0.3 ml of 1 M Tris-HCl, pH 9.0, when the $A_{280}$ had again returned to a stable baseline value, the column was washed with 5 bed volumes of elution buffer, followed by 10 bed volumes of regeneration buffer and 5 bed volumes of binding buffer so that the column was ready for the next purification cycle. The fractions containing the purified immunoglobulin were pooled, and concentrated using a stirred ultrafiltration cell (Amicon Corp.). The final concentration of purified immunoglobulin was greater than 5 mg/ml as determined by the Lowry assay for total protein. The purified antibody was dialyzed against two changes of phosphate-buffered saline (PBS) containing 0.1% sodium azide for 48 hours at 4° C.

The purified monoclonal antibodies were titrated in a 96-well microtiter plate ELISA system to provide a measure of their immunological reactivity for specific enterotoxin. The end point titers for the antibodies which were obtained were compared to reference titer values for previously acceptable lots of each antibody. Antibodies of sufficient titer were accepted as immunologically functional coating antibodies for immobilization to a diagnostic reagent holder, e.g. dipstick or for conjugation to an enzyme for use as probes in the immunoassay.

Diagnostic reagent holders (dipsticks) with nitrocellulose membranes attached were prepared for immobilization of antibodies to the membrane surface by first immersing the membranes in phosphate-buffered saline for one hour at room temperature to improve the wetability of the membrane. The sticks were removed from the solution and the membranes were allowed to air dry. Solutions of the purified monoclonal antibodies, each of which is specific for one of the *Staphylococcal* enterotoxins A, B, C, D or E, and a non-specific control mouse immunoglobulin (Jackson Immuno Research Laboratories, Inc.) were applied to different regions of the membrane by spotting 2 microliters of antibody solution directly onto the membrane surface. The concentration of each antibody used was one which was known to saturate the binding sites of the nitrocellulose: 250 micrograms/ml of 3A antibody (specific for A toxin), 50 micrograms/ml of 2B antibody (specific for B toxin), 300 micrograms/ml of IC3 antibody (specific for C1, C2, and C3 toxins) 200 micrograms/ml of 3D antibody (specific for D toxin) 250 micrograms/ml of 4E antibody (specific for E toxin), and 200 mircrograms/ml of non-specific control mouse immunoglobulin. The dipsticks were allowed to air dry at room temperature, and the remaining protein binding sites on the membrane were blocked by immersing the dipsticks in a solution of phosphate-buffered saline containing 0.5% Tween-20 and 3% bovine serum albumin. Following an overnight incubation at room temperature in this blocking solution, the sticks were allowed to air dry.

Purified monoclonal antibodies 2A (specific for A and E toxins), 6B (specific for B, C1, C2, and C3 toxins), and 1D (specific for D toxin) were covalently linked to the enzyme alkaline phosphatase for use as conjugated probes to determine the presence of A, B, C1, C2, C3, D, and E toxins bound to antibodies immobilized to the membrane surface of the diagnostic reagent holder dipstick. Each conjugate was prepared by a stoichiometrically controlled two step procedure which utilizes glutaraldehyde as the bifunctional cross-linking agent. In this procedure 0.47 ml of EIA grade alkaline phosphatase (2500 U/mg, Boehringer Mannheim Corp.) was added to 1.2 ml of 50 mM potassium phosphate buffer pH 7.2, containing 13.4 microliters of aqueous glutaraldehyde solution (25%, Sigma Chemical Co.). The mixture was stirred at room temperature for 90 minutes to allow attachment of glutaraldehyde to free amino groups of the enzyme molecule. After this incubation period, a 2 ml aliquot of purified monoclonal antibody at a concentration of 1 mg/ml was added, the mixture stirred for an additional 90 minutes, and placed on ice to stop the conjugation reaction. The conjugate was dialyzed against two changes of phosphate-buffered saline containing 0.1% sodium azide for 48 hours at 4° C. Bovine serum albumin was added to the dialysate to a final concentration of 3% for stabilization during prolonged storage at 4° C. The antibody-enzyme conjugates were titrated in a 96-well microliter plate ELISA system to provide a measure of their immunological reactivity for specific enterotoxin. The end point titers for the conjugates which were obtained were compared to reference titer values for previously acceptable lots of each conjugate. Conjugates of sufficient titer were accepted for use as probes in the dipstick assay for *Staphylococcal* enterotoxins.

Solid foods such as ham, sausage, noodles and cheese, which represent the types of foods most commonly associated with outbreaks of *Staphylococcal* food poisoning, were converted to a homogeneous liquid suspension in order to perform the assay for *Staphylococcal* enterotoxins. In a typical extraction, 20 milliliters of water were added to 20 grams of food, and the mixture was homogenized for 30 seconds using a stomacher lab-blender (Tekmar Co.). For more viscous foods, twice the volume of water was used. *Staphylococcal* enterotoxin was added to the food either before or after homogenization. The food homogenate was tested directly using the diagnostic reagent holder dipstick described above. Positive results were obtained with food samples to which low levels of enterotoxin were added. Additional extraction steps were carried out on the food homogenates to improve the sensitivity of *Staphylococcal* enterotoxin detection. The homogenate was typically adjusted to pH 4.5 with 6 N HCl and centrifuged for 20 minutes at 20,000×g, and the supernatant was adjusted to pH 7.5 with 5 N NaOH, centrifuged again 20 minutes at 20,000×g, and the supernatant was used directly in the dipstick assay. For food extracts prepared in this way the sensitivity of enterotoxin detection was 1 nanogram per milliliter of extract for each toxin in each food tested.

Liquid foods such as milk were tested directly by immersing the diagnostic reagent holder dipstick in the liquid food and running the test in an identical manner as for the solid food homogenates. In testing these foods, it was also determined that sensitivity may be improved to 1 nanogram per milliliter by carrying out the additional extraction steps described above.

Diagnostic reagent holders (dipsticks) provided with a nitrocellulose membrane having immobilized to it monoclonal antibodies specific for the individual *Staphylococcal* enterotoxins were immersed in a tube containing 1 ml of a liquid food, food homogenate, or food extract prepared as described above, or 1 ml of PBS. Each of these solutions contained 1 ng/ml of an added *Staphylococcal* enterotoxin or a mixture of enterotoxins, each at 1 ng/ml concentration. The dipstick remained immersed in these sample solutions for a 1 hour incubation period at room temperature with shaking on a rotary shaker. The dipsticks were then removed from the samples and washed with shaking for 5 minutes in PBS with 0.5% Tween-20, then twice more with shaking in PBS alone, 5 minutes per wash. A mixture of monoclonal antibody-alkaline phosphatase conjugates prepared as described was made as follows: 1:1000 dilutions of 2A conjugate (specific for A and E toxins), 6B conjugate (specific for B, C1, C2 and C3 toxins), and 1D conjugate (specific for D toxin) were made in the same solution (30 microliters of each conjugate in 30 ml of PBS containing 0.5% Tween-20 and 3% BSA). The dipsticks were immersed in this conjugate mixture, 2 ml per stick, and incubated for 30 minutes at room temperature with shaking. The dipsticks were washed twice in PBS-Tween, then three times with shaking in PBS, 5 minutes per wash, to remove unbound monoclonal antibody-alkaline phosphatase conjugate from the membrane surface.

Following the removal of unbound monoclonal antibody-enzyme conjugate from the diagnostic reagent holder dipstick, the presence of bound conjugate was indicated by immersing the dipstick in a solution of 5-bromo 4-chloro indolyl phosphate (BCIP, Sigma Chemical Co.) and nitroblue tetrazolium (NBT, Sigma Chemical Co.). The BCIP and NBT solutions were prepared individually as follows: 3.2 mg of BCIP was dissolved in 10 ml of 0.1M Tris-HCl, 0.1M NaCl, 5 mM $MgCl_2$, and 8.8 mg of NBT was dissolved in 10 ml of the same solution. These solutions were mixed together immediately prior to use. The dipsticks were immersed in the substrate mixture for 30 minutes at room temperature with shaking, then rinsed with water and air dried, providing a permanent record of the assay result. The entire assay procedure requires few to none pipetting steps, minimal hands-on time, and can be performed in approximately two hours. The substrate of the enzyme conjugate, BCIP, was hydrolyzed by the conjugate bound to the toxin on the membrane to yield a reaction product which reduces the NBT to an insoluble blue product that binds to the membrane on the dipstick. The presence of *Staphylococcal* enterotoxin in the sample which was bound by the immobilized first monoclonal antibody on the membrane and detected by the binding of the second monoclonal antibody-enzyme conjugate, was indicated by the presence of a blue spot on the nitrocellulose membrane. When no *Staphylococcal* enterotoxin was present in the sample the nitrocellulose membrane remained white. The area of the membrane to which the control mouse immunoglobulin was immobilized remained white in each case. The identification of the particular *Staphylococcal* enterotoxin that was present, that is, A, B, C, D or E, was indicated by the presence of a blue spot on the distinct and identifiable area of the membrane to which monoclonal antibody specific for that toxin was immobilized. This method, which employs a diagnostic reagent holder dipstick, is capable of detecting one nanogram per milliliter of one or a multiplicity of *Staphylococcal* enterotoxins in a liquid food, food homogenate or food extract.

EXAMPLE 25

Enzyme Immunoassay (EIA) for Coliform Bacteria

Experiments were performed to compare the detection efficiency for fecal coliforms between the method of the present invention (CAP-EIA MPN) and the EPA approved MPN confirmatory procedure using the *EC* broth at 44.5° C.

The experiments were performed as a standard 5-vial MPN assay with the following modifications. Instead of the lauryl sulfate tryptose (LST; Difco Labs, Detroit, Mich.) broth, or lactose broth (Difco Labs, Detroit, Mich.) phenol red lactose broth (PRLB; Ditco Labs, Detroit, Mich.) containing 80 micrograms/ml of 4-methylumbelliferone glucuronide (MUG; Sigma Chemical Co., St. Louis, Mo.) was used as the presumptive medium. PRLB was chosen because the phenol red dye allowed the detection of acid production from the fermentation of lactose. Gas which evolved from lactose fermentation was trapped by the inverted Durham vials which were inserted inside each of the vials. MUG was included as an option to provide a preliminary confirmation for the presence of E. coli. E. coli, the principal fecal coliform, is the only organism prevalent in water which can cleave MUG to release a fluorogenic radical visible under UV light (4, 10).

The CAP-EIA MPN assay format provides 3 types of data: 1) acid and gas production from the fermentation of lactose (presumptive coliform analysis); 2) fluorescence from the cleavage of MUG (presumptive confirmation for E. coli or fecal coliforms); and 3) CAP-enzyme immunoassay confirmation (confirmatory test based on monoclonal antibodies). The results of the MUG and CAP-EIA reactions were then compared to the results obtained by Standard Methods (1) based on lactose fermentation at the elevated temperature of 44.5° C. in EC broth (Difco Labs, Detroit, Mich.).

The experiment was performed as follows: to obtain the three 10-fold dilution series as required for an MPN assay, the following volumes of water sample collected from a nearby creek were used to inoculate the vials containing 10 ml of PRLB-MUG and equipped with a polystyrene well inside the vial cap.

Series A—5 vials, 1.00 ml inoculum
Series B—5 vials, 0.10 ml inoculum
Series C—5 vials, 0.01 ml inoculum All vials were then incubated overnight for approximately 18–20 hours at 35° C.

The following day, all the vials were examined for acid and gas production as well as fluorescence under UV light. All vials which showed turbidity (growth), regardless of the acid or gas reactions, were inverted to allow the cell-medium suspension to fill the polystyrene well inside the cap. The inverted vials were held at 35° C. for 1 hour to allow bacteria (antigen) to attach to the polystyrene cap-wells. The antigen bound cap-wells were then removed from the vials to continue with the antibody based confirmatory tests.

To perform the EIA (enzyme immunoassay) portion of the assay, the wells were treated for 30 minutes at 35° C. with a solution of 3% bovine serum albumin (BSA; Sigma Chemical Co., St. Louis, Mo.) in phosphate-buffered saline (PBS; NaCl, 8.5 g: $Na_2HPO_4$, 1.02 g: $NaH_2PO_4.H_2O$, 0.386 g: distilled water, 1000 ml; pH 7.2) to block out any unbound sites on the polystyrene. Once the BSA solution was decanted, the wells were washed twice with PBS, then 50 microliters of a hybridoma cell supernatant which contained monoclonal antibodies directed to E. coli cells were added to each well and incubated for 1 hour at 35° C. to allow the antibody to interact with the specific antigens (E. coli cells) bound to the polystyrene. After decanting the antibody supernatant, traces of any unbound antibody were removed by washing the wells 3 times using a PBS-Tween 20 solution (PBS+0.05% Tween 20, J.T. Baker Chemical Co., Phillipsburg, N.J.). An affinity-purified alkaline phosphatase-labeled goat antibody to mouse IgG (conjugate; KPL, Gaithersburg, Md.) was diluted 1:1000 in PBS, and 50 microliter aliquots were added to each well. Following a 1 hour incubation at 35° C., any unbound conjugate in the wells was removed by 4 washings with PBS-Tween 20 solution. The alkaline phosphatase substrate used for detection was sodium para-nitrophenyl phosphate or Sigma-104 substrate (Sigma Chemical Co., St. Louis, Mo.), prepared at a final concentration of 1 mg/ml in 10% diethanol-amine buffer (diethanolamine, 97 ml; $NaN_3$, 0.2 g; $MgCl_2 6H_2O$, 100 mg; and distilled water, 800 ml, pH 9.8). The substrate was added in 100 microliter aliquots per well, and following 30 minutes incubation at 35° C., the reaction in the wells was observed visually. For the purpose of quantitation in this example, the reacted substrate solution was transferred into a microtiter plate and determined instrumentally with Titertek Multiscan (Flow Laboratories, Mcleans, Va.) equipped with a 405 nm filter.

To perform the conventional confirmatory test for fecal coliforms using EC broth (Difco Labs, Detroit, Mich.), a loopful of growth from each of the overnight PRLB was aseptically transferred into a tube containing 10 ml of EC broth and equipped with an inverted Durham vial. The tubes were then incubated for 24–48 hours at 44.5° C. as specified by Standard Methods (1) then examined for evidence of lactose fermentation (trapped gas inside the Durham vials). Any trace of gas bubbles within the vials was considered a positive reaction.

The summarized data for each experiment are shown on Table XII and XIII.

The results of experiment 1 indicate that, based on gas production from lactose, a positive combination of 551 is obtained, which according to the statistical MPN table is 35 coliforms/ml (presumptive test). Of the gas positive (+) vials, only 4 (A2–A5) were positive by the MUG assay, and therefore most likely contained E. coli (presumptive confirmation for E. coli or fecal coliforms). Among the confirmatory data, the Conventional EC test showed 5 tubes (A1–A5) to be positive for fecal coliforms, whereas by the CAP-EIA method, only 4 vials, (A2–A5) showed positive reactivity. The positive EIA readings ranged from 0.55 up to 1.06, with the negative reaction reading around 0.20. The positive EIA data are strongly supported by the positive MUG data in that both of these tests indicated the presence of fecal coliforms in the same vials, A2–A5. The fact that vial A1 was negative on MUG and EIA but positive by EC was not surprising because of the incidence of false (+) and false (−) reactions commonly associated with the Conventional MPN Methods (15, 16, 20). The selectivity of the EC medium along with the elevated temperature of incubation has been known to affect the recovery of fecal coliforms. Also, about 7% of the fecal coliforms (E. coli) will not produce gas on EC (false negatives), and 8% of the nonfecal coliforms have been found to be able to grow and produce gas in EC broth (false positives). The EC reaction observed in tube A1 therefore may be a false positive reaction, which would account for its discrepancy with the MUG and EIA results for tube A1. With regard to the other vials (B1–B5, C1–C5) in the same experiment, excellent correlation was observed between all the tests. In other words, vials which were MUG (−) were also EC (−) and EIA (−), thus confirming the absence of fecal coliforms in these vials.

In experiment 2, the water sample used to inoculate the vials was more heavily contaminated, because all presumptive tubes were positive for gas production. Based on the statistical MPN table, a positive combination of 5 5 5 would indicate the presence of greater than 240 coliforms/ml. In comparing the confirmatory test, excellent correlation was obtained between MUG, EC and the antibody based EIA. Every vial that showed fluorescence (MUG+) was also positive by EC as well as EIA. The EIA reactions ranged from slightly weak positive readings of 0.46 (B2) up to very strong reactions of 2.15 observed for C4.

The results of these two experiments indicate that the antibody based CAP-EIA test of the present invention is as efficient as the EPA approved *EC* test in confirming the presence of fecal coliforms. Additionally, as shown in the case of vial A1 in experiment 1, the CAP-EIA test is less susceptible to false positive or negative reactions due to the specific nature of the antibody-antigen reactions. Furthermore, the CAP-EIA test offers several distinct advantages over the conventional MPN test, namely: 1) simplicity—both the presumptive and the confirmatory test can be done using the same vial without the need for additional transfers or medium; 2) speed—the CAP-EIA test can be completed in ⅓ to ½ the time required for a conventional test; and 3) specificity—antibodies are highly specific for their antigenic targets.

These advantages plus the unique cap-well design of the CAP-EIA, which can provide 4 separate pieces of data (acid, gas, fluorescence, and EIA) from the same vial, makes it a far superior alternative to the conventional MPN test for analyzing coliforms and fecal coliforms in water and/or food samples.

The concept of doing EIA in a vial or tube cap containing a polystyrene insert is not limited to coliform or fecal coliform assay, and should be equally applicable to the detection of other bacteria.

EXAMPLE 26

Preparation of 2-[3-(4-methyl-2,2'-bipyridine-4'-yl)-propyl]-1,3-dioxolane

Under an inert atmosphere of argon, 30 ml of dry tetrahydrofuran (THF) and 7.65 ml of dry diisopropylamine (54.6 mmol) were added to a 3-neck, 600 ml flask via syringe with stirring. The solution was cooled to −78° C. by immersing the flask in a mixture of dry ice-isopropanol in a low form beaker. 21.6 ml of 2.5M n-butyl lithium (54 mmol) were slowly added to the flask. The resulting solution was stirred for 15 min and a solution of 9.58 g of 4,4'-dimethyl-2,2'-bipyridine (52 mmol) dissolved in 300 ml of dry THF was added dropwise by cannula with stirring over 1 hr.

The resulting brown mixture was further stirred at −78° C. for 2 hrs, 10 g of 2-(2-bromoethyl)-1,3-dioxolane (55 mmol) were added by syringe and the resulting mixture stirred at −78° C. for 5 min. The reaction vessel was then placed in an ice bath (10° C.) and after 30 min began to change color (after 1 hr the color was dark violet; after 2 hrs the color was blue; after 2.5 hrs the color was green; and after 3.25 hrs the color was lemon yellow.

The reaction mixture was quenched with 30 ml of saturated NaCl followed by 10 ml of water and 50 ml of ether. The aqueous phase was extracted twice with 300 ml of ether and the combined ether phases were back-extracted with 100 ml of water and dried over anhydrous sodium sulphate.

To purify the reaction product, the sample was separated on alumina (Merck) 90, activity III, neutral. The eluants used were petroleum ether/diethyl ether (2:1) followed by petroleum ether/diethyl ether (1:1) (the starting material elutes completely with petroleum ether/diethyl ether (2:1), followed by the product).

Proton NMR analysis confirmed that the structure of the isolated reaction product is

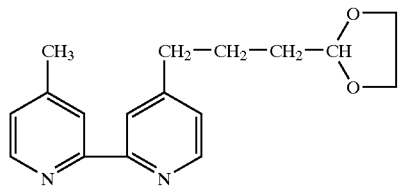

EXAMPLE 27

Preparation and Purification of 4-(butan-1-al)-4'-1-methyl-2,2'bipyridine 2 g of 2-[3-(4-methyl-2,2-bipyridine-4'-yl)-propyl]-1,3 dioxolane were dissolved in 50 ml 1N HCl and heated for 2 hrs at 50° C. The solution was cooled, adjusted to between pH 7 and 8 with sodium bicarbonate and extracted twice with 100 ml of chloroform.

The combined chloroform phases were washed with a small amount of water, dried over sodium sulfate, filtered and rotoevaporated to yield a yellow oil.

The yellow oil was purified on a silica gel column using ethyl acetate/toluene (1:1) as the eluant, the impurity being eluted with methanol.

Proton NMR analysis [δ 1*96–2*11 (m, 2H); 2*43 (s, 3H); 2*46–2*50) (t, 2H); 2*53–2*80 (m, 2H); 7*12–7*14 (m, 2H); 8*17–8*21 (br. s, 2H); 8*52–8*58 (m, 2H); 9*89 (s, 1H)] confirmed that the structure of the reaction product is

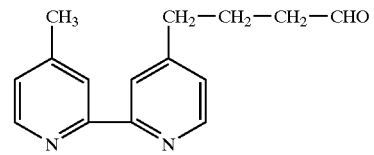

EXAMPLE 28

Preparation of 4-(4-methyl-2,2'-bipyridine-4'-yl) butyric acid 0.5 g of 4-(butan-1-al)-4'-methyl-2,2'-bipyridine (2.0 mmol) were dissolved in 10 ml absolute acetone. 225 mg of finely powdered potassium permanganate ($KMnO_4$; 1.42 mmol) were added in portions to the solution with stirring. The reaction was followed by thin layer chromatography, (silica; ethyl acetate/toluene 50:50), which indicated that while the aldehyde gradually disappeared a bipyridine of low $R_f$ was formed.

After the reaction reached completion, water was added and the $MnO_2$ was filtered and washed with small portions of $Na_2CO_3$(aq.). The acetone was rotoevaporated and the residue extracted with $CH_2Cl_2$ to remove non-acidic bipyridines. The aqueous solution was made acidic by careful addition of 1.0N HCl to pH 4.8. The solution became partially cloudy upon reaching this pH, the suspension redissolving at lower pH. The mixture was extracted five times with equal volumes of $CH_2Cl_2$, dried over $Na_2SO_4$ and rotoevaporated to an oil which promptly solidified in vacuo. The crude solid was recrystallized from chloroform: petroleum ether to obtain white crystals.

Melting point: 103.5° C.–105.5° C.; IR; 1704 $cm^{-1}$. Proton NMR analysis was consistent with the following structure

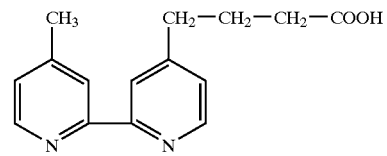

EXAMPLE 29

Preparation of bis(2,2'bipyridine)[4-(butan-1-al)-4'-methyl-2,2'-bipyridine]ruthenium (II) diperchlorate: Compound I 250 mg of ruthenium bipyridyl dichloride dihydrate (0.48 mmol) (Strem) in 50 ml of ethylene glycol were quickly heated to boiling and then immersed in a silicone oil bath (130° C.). To the resulting purple-orange solution were added 150 mg of 2-[3-(4-methyl-2,2'-bypyridine-4'-yl) propyl]-1,3-dioxolane (0.53 mmol) in 10 ml of ethylene glycol. The resulting orange solution was stirred at 130° C. for 30 min, cooled to room temperature and diluted 1:1 with distilled water.

A concentrated solution of sodium perchlorate in water was added to the solution, causing the appearance of a very fine orange precipitate. The mixture was refrigerated overnight, filtered and the precipitate washed with water.

The precipitate was dissolved in hot water and recrystallyzed by adding perchloric acid to the solution to produce bright orange crystals which were then filtered, washed with cold water and dried. This recrystallization procedure was repeated, yielding a total of 150 mg of bright orange crystals.

NMR analysis indicated the following structure

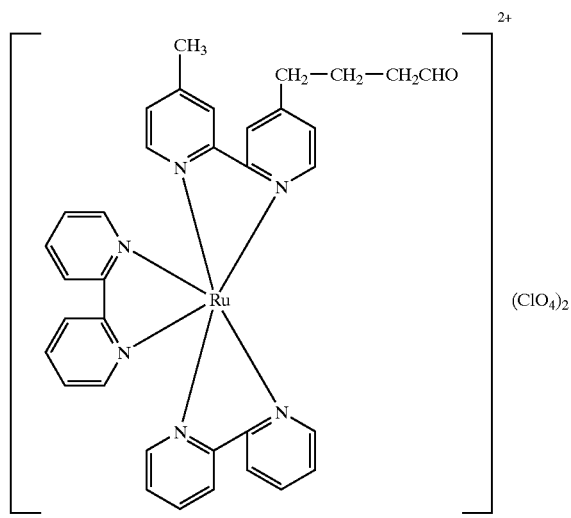

Within the present application, the above-identified compound is referred to as Compound I.

EXAMPLE 30

Preparation of bis(2,2'-bipyridine)[4-(4-methyl-2,2'-bipyridine-4'-yl)-butyric acid) ruthenium (II) dihexafluorophosphate: Compound II 134 mg of 4-(4-methyl-2,2'-bipyridine-4'-yl)-butyric acid (0.52 mmol) were dissolved in 50 ml of water. The solution was degassed with argon and 250 mg of ruthenium bipyridyl dichloride dihydrate (Strem) (0.48 mmol) were added. The mixture was refluxed under argon for 4 hrs. The water was rotevaporated and the residue redissolved in the minimum amount of water and loaded onto a SP-25-Sephadexion-exchange column. After eluting impurities with water, the compound was eluted as a red band with 0.2 M NaCl solution and isolated as a hexafluorophosphate by addition of a saturated aqueous solution of $NH_4PF_6$. The crude product was reprecipitated twice from hot acetone with diethyl ether. Anal: Calculated; C, 43.80%; H, 3.36%; N, 8.76%. Found; C, 43.82%; H, 3.54%; N, 8.55%.

Proton NMR analysis was consistent with the following structure

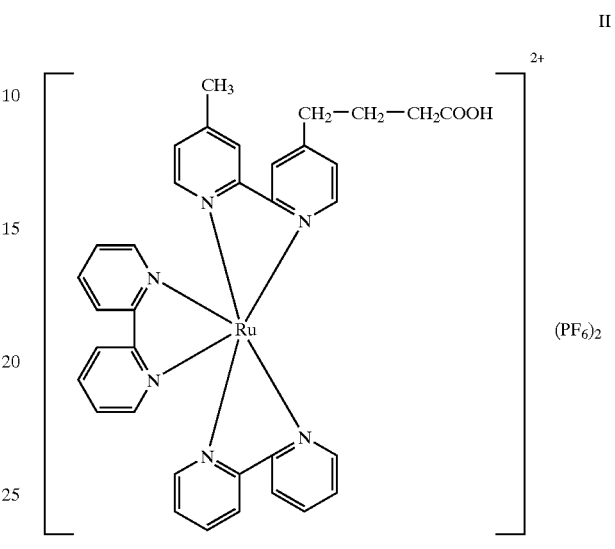

EXAMPLE 31

Preparation of N-(4-[4-methyl-2,2'-bipyridine-4'-yl)-butyl)-phthalimide

Under an inert atmosphere of argon, 30 ml of dry tetrahydrofuran (THF) and 7.65 ml of dry diisopropylamine (54.6 mmol) were added to a 3-neck, 600 ml flask via syringe with stirring. The solution was cooled to −78° C. by immersing the flask in a mixture of dry ice-isopropanol in a tow form beaker. 21.6 ml of 2.5 n-butyl lithium (54 mmol) were slowly added to the flask. The resulting solution was stirred for 15 min and a solution of 9.58 g of 4,4'-dimethyl-2,2'-bipyridine (52 mmol) dissolved in 300 ml of dry THF was added dropwise by cannula with stirring over 1 hr.

The resulting brown mixture was further stirred at −78° C. for 2 hrs, 100 g of 1,3-dibromopropane (0.495 mol) were rapidly added and the resulting mixture stirred at −78° C. for 1 hr. The mixture was then stirred at room temperature for 2 more hrs. The color of the mixture changed from brown to blue to yellow. Most of the solvent was rotoevaporated and 200 ml of water were added causing the formation of two phases. Concentrated HCl was added to lower the ph to 0. The organic layer was discarded. The aqueous layer was washed twice with 100 ml of ether. The pH was raised to between 1 and 2. A red oil separated and was extracted into $CH_2Cl_2$. After drying the solution with anhydrous $Na_2CO_3$, most of the $CH_2Cl_2$ was rotoevaporated and the sample was loaded onto a silica gel column. The sample was eluted with chloroform yielding a light yellow oil which crystallized after cooling overnight (12.37 g).

4 g of the crude 4-(4-bromobutyl)-4'-methyl-2, 2'bipyridine (13.3 mmol) thus prepared were then added to a suspension of 2.46 g potassium phthalimide (13.3 mmol) in 60 ml of dimethylformamide (DMF). The mixture was then stirred at approximately 50° C. for 2 hrs. 90 ml of $CHCl_3$ were added to the mixture, followed by 125 ml of water. The CHCl3 layer was separated and the aqueous layer was extracted twice with 50 ml of chloroform. The combined CHCl₃ layers were washed with 50 ml of H₂O, dried over anhydrous Na₂SO₄, and rotoevaporated, leaving a pale orange oil which solidified overnight. The crude product was recrystallized from acetone/ethanol, yielding 2.21 g (44.5%) of white crystals (melting point, 114.5–117.8° C.). Anal: Calculated; C, 74.38%; H, 5.70%; N, 11.31%. Found: C, 73.98%; H, 6.14%; N, 11.28%. IR: Phthalimide carbonyl stretch 1771 and 1704 cm$^{-1}$. Proton NMR analysis showed aromatic resonances (δ 7*75–7*85, m, 4H) in addition to the usual bipyridyl derivative signals. These data are consistent with the following structure

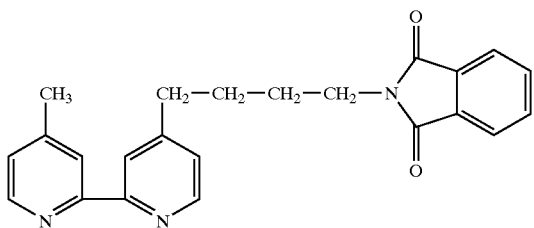

EXAMPLE 32

Preparation of theophylline-8-butyric-[4(4-methyl-2, 2'-bipyridine-4'-yl)-butyl]amide: Compound III 370 mg (1 mmol) of N-[4-(4-methyl-2,2'-bipyridine-4'-yl)-butyl]-phthalimide were slurried in 10 ml ethanol, treated with hydrazine hydrate (720 mg, 1.4 mmols), stirred and refluxed for 4 hrs, during which time all the solid went into solution. Towards the end of the reaction a white precipitate began to form.

After cooling, the reaction mixture was made basic with 50% NaOH and then poured into 100 ml of water. A solution resulted and Na₂CO₃ was added to salt out the product as an oil. The amine was extracted using three 40 ml portions of CHCl₂. The extracts were dried with CaSO₄, filtered and evaporated to give the amino-bipyridine derivative as a colorless oil (yield=0.135 gm; 56%).

1.34 g (5.6 mmol) of 4-[4-(1-aminobutyl)]4'-methyl-2,2'-bipyridine and theophylline-8-butyric acid (1.18 g; 4.4 mmol) were dissolved at room temperature in 10 ml of dry pyridine. To the solution were added 1.16 g (5.6 mmol) of dicyclohexylcarbodiimide. Stirring at room temperature was continued overnight. Thin layer chromatography on alumina (mobile phase=15% methanol/chloroform) revealed one product spot with an $R_f$ of 0.68. Precipitated dicyclohexylurea was removed by filtration and the pyridine was stripped to give a solid, which was triturated in ether and filtered (yield=2.13 g; 99%).

EXAMPLE 33

Preparation of bis-(2,2'-bipyridine)[theophylline-8-butyric-4-(4-methyl-2,2'-bipyridine-4'-yl)-butyl amide)ruthenium (II) dichloride: Ru (II)-Compound III Conjugate To a mixture of 154 mg (0.296 mmoles) of bis-(2,2'-bipyridine)ruthenium (II) dichloride dihydrate and 175 mg (0.357 mmoles) of Compound III described above were added 40 ml of ethanol/H₂O (1:1, v/v). This mixture was argon degassed in the dark for 15 min and refluxed in the dark under argon for 3 hrs to produce a clear, cherry red solution. The resulting clear, cherry red solution was allowed to cool to room temperature and the solvent was stripped off using a rotary evaporator while maintaining the solution in the dark under a temperature less than or equal to 37° C.

The resulting residue was dissolved in approximately 1–3 ml of methanol, loaded onto a Sephadex LH-20 chromatography column (75 cm×3 cm) and eluted at a flow rate of about 0.4–0.7 ml/min. A bright red band (product) was closely followed by a brown, nonluminescent band (impurity) and two luminescent bands. The red product band was found to be contaminated with a small amount of the material from the brown, nonluminescent band. This contaminating material was separated from the product by running the sample on a second Sephadex LH-20 column under similar conditions.

The red product was obtained by stripping the solvent off by rotoevaporation. The resulting solid material was dissolved in approximately 1 ml of methanol and reprecipitated in approximately 75 ml of diethyl ether to yield an orange powder which was collected by filtration.

Anal: Calculated; C, 54.51%; H, 5.72%; N, 13.99%; O, 10.47%; Cl, 6.44. Found; C, 55.04%; H, 6.35%; H, 13.18; O, 10.62%; Cl, 6.68.

EXAMPLE 34

Modulation of Electrochemiluminescent Signal Generated by Ru(II)-Compound III Conjugate Using Antibodies Specific for Theophylline The Ru(II)-Compound III Conjugate described in Example 33 was diluted to a final concentration of 150 nM using 0.1M phosphate buffer, pH 6.0, containing 0.35 M sodium fluoride (PBF Buffer). Monoclonal antibody (clone number 9-49, ascites lot number W0399, cat number 046) specific for theophylline was obtained from Kallestad Laboratories, Inc. (Chaska, Minn.). The monoclonal antibody was diluted to different concentrations using PBF Buffer (between 21.9 micrograms of protein/ml to 700 micrograms/ml).

Another monoclonal antibody (control MAB) that was not reactive with theophylline was obtained from Sigma (St. Louis, Mo.) and was diluted to different concentrations between 21.9 micrograms of protein/ml to 700 micrograms/ml using PBF Buffer. A standard solution of theophylline was prepared using theophylline obtained from Aldrich Chemical Co., (Milwaukee, Wis., cat number 26-140-8, M.W. 180.17). Theophylline was dissolved in PBF Buffer to give a final concentration of 75 micromolar and was diluted with PBF Buffer to 6 micromolar for use in assays. Prior to making electrochemiluminescence measurements a solution containing 250 mM oxalic acid and 5% (v/v) Triton-X 100 (ECl solution) was added to the reaction mixture. Measurements were made using a Berthold luminometer that was modified to allow the placement of two platinum gauze electrodes into the test tube containing the reaction solution. The electrodes were connected to a potentiostat and the electrochemiluminescence measurement was made by sweeping an applied potential across the electrodes from 1.5 to 2.5 volts at a scan rate of 50 mV/sec. The Berthold luminometer used for the measurement had a high gain, red sensitive photomultiplier tube. The luminometer output to the recorder was adjusted to $10^5$ counts/volt. The measurements were recorded on an X-Y-Y' recorder and the peak height was used as the measurement of electrochemiluminescence. The electrodes were cleaned between measurements by rinsing with a buffer at pH 4.2 containing 0.1 M phosphate, 0.1 M citrate, 0.025 M oxalic acid, and 1% Triton X100; pulsing the electrodes in this solution between +2.2 to −2.2 volts for 60 sec; and followed by +2.2 volts for 10 seconds. Next the electrodes were removed from this solution, rinsed in distilled water and wiped dry. The experiment was carried out as outlined in Table XIV.

A solution of control monoclonal antibodies, antibodies to theophylline or PBF Buffer was added to a set of test tubes (Step 1). To the tubes, a solution of theophylline or PBF Buffer was added (Step 2). The solutions were mixed by briefly shaking the test tubes and allowed to react for 25 min at room temperature. Then a solution of Ru(II)-Compound III Conjugate was added to the tubes (Step 3). The test tubes were shaken and kept at room temperature for 15 min. Finally, 100 microliters of the ECL solution was added to each tube and electrochemiluminescence was measured as described above. The results are listed in Table XV.

TABLE XIV

Experimental Design for Studying the Effect of Antibody-Ru(II)-Compound III Conjugate Interactions on Electrochemiluminescence

| Step 1<br>100 microliters of: | Step 2<br>200 microliters of: | Step 3<br>100 microliters of: |
|---|---|---|
| A. Control monoclonal antibody (2.19 micrograms to 70 micrograms) or | Buffer | Ru(II)-Compound III Conjugate |
| B. Anti-theophylline antibody (2.19 micrograms to 70 micrograms) or | Buffer or Theophylline | Ru(II)-Compound III Conjugate |
| C. PBF Buffer | Buffer | Ru(II)-Compound III Conjugate or Buffer |

TABLE XV

Effect of Antibody and Theophylline on Electrochemiluminescence of Ru(II)-Compound III Conjugate

| Antibody Protein Concentration (micrograms/tube) | Control MAB + Ru(II)-Compound III | Anti-Theophylline MAB + RU(II)-Compound III | Anti-Theophylline MAB + Theophylline Ru(II)-Compound III |
|---|---|---|---|
| | Luminescence Measurement | | |
| 2.19 | 55,000 | 40,000 | 43,000 |
|  | 55,000 | 41,000 | 57,000 |
| 4.38 | 57,000 | 22,500 | 37,000 |
|  | 57,000 | 25,000 | 36,000 |
| 8.75 | 53,000 | 20,000 | 33,500 |
|  | 50,000 | 22,000 | 30,500 |
| 35.0 | 43,000 | 13,500 | 17,500 |
|  | 41,000 | 14,000 | 16,000 |
| 70.0 | 42,000 | 11,000 | 11,000 |
|  | 37,500 | 12,000 | 12,500 |

The electrochemiluminescence of duplicate samples were measured as described above. The electrochemiluminescence of Ru(II)-Compound III Conjugate used in the above study was 57,200 when measured in buffer without the addition of antibody. The background for the buffer mixture was 5750.

The data show that a monoclonal antibody which specifically recognizes theophylline, when contacted with an analog of theophylline to which a ruthenium compound is attached e.g., Ru(II)-Compound III, will decrease the electrochemiluminescence. The decrease in electrochemiluminescence is proportional to the antibody concentration when the Ru(II)-Compound III Conjugate concentration is held constant. When an antibody is used which does not react with theophylline, only a slight decrease in the electrochemiluminescence is seen at the highest concentration of antibody.

The data also show that when theophylline is contacted with the anti-theophylline antibody and then the Ru(II)-Compound III. Conjugate is added to the mixture, the amount of electrochemiluminescence is greater. This demonstrates that theophylline competes for the binding of antibody to Ru(II)-Compound III Conjugate resulting in a greater amount of Ru(II)-Compound III Conjugate which can generate electrochemiluminescence.

EXAMPLE 35

Assay for Theophylline in Serum Based on a Homogeneous Electrochemiluminescent Immunoassay Based on the results described Example 34, a homogeneous immunoassay for theophylline was developed using antibody to theophylline and the Ru(II)-Compound III Conjugate described in Example 33 in a competitive binding format. The materials used were described in Example 34 except the PBF buffer was 0.1M phosphate buffer, pH 6.0, containing 0.1M sodium fluoride. For this assay, a specific concentration of monoclonal antibody to theophylline was chosen. The antibody concentration was 55 micrograms/ml. The Ru(II)-Compound III Conjugate concentration was adjusted to 175 nM. Theophylline was added to human serum to give final concentrations of 2.5, 5, 10, 20 and 40 micrograms of theophylline/ml of serum.

Figure 2:
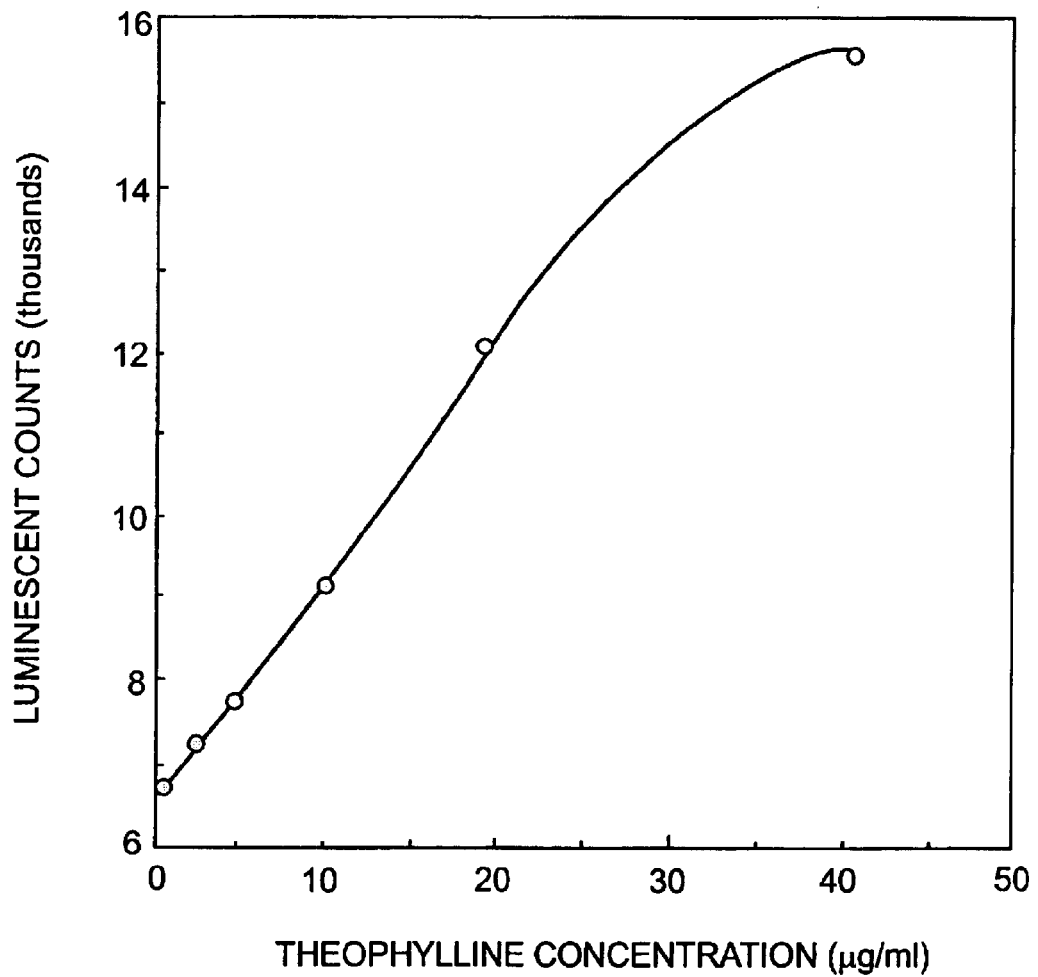
FIG. 2 graphically depicts the results of a homogeneous ECL theophylline assay.

The assay was performed by adding 10 microliters of serum to 290 microliters of anti-theophylline monoclonal antibody and holding the solution at room temperature for 25 min. Then 100 microliters Ru(II)-Compound III Conjugate were added to each tube to give a final concentration of 35 nM and holding this solution at room temperature for 15 min. 100 microliters of the ECL solution described in Example 34 were then added to each tube and electrochemiluminescent properties of the solutions were measured as previously described using a sweep mode for 1.5 volts to 2.5 volts at 50 mV/sec. The data are shown in FIG. 2 and demonstrate that there is a correlation between the concentration of theophylline in a serum sample and the amount of electrochemiluminescence that is emitted by the reaction mixture. This observation demonstrates that it is possible to develop an assay for theophylline.

Based on these results, one skilled in the art would be able to develop a homogeneous electrochemiluminescence immunoassay for detecting and quantifying an analyte of interest in a biological matrix.

EXAMPLE 36

Assay for Theophylline in Hemolyzed, Lipemic, Icteric and Normal Serum Samples Based on a Homogeneous Electrochemiluminescent Immunoassay and Comparison to a Fluorescence Polarization Assay The concentration of theophylline in different types of serum samples was determined using a homogeneous electrochemiluminescent immunoassay. The format for the assay was a competitive binding assay using a monoclonal antibody specific for theophylline and the Ru(II)-Compound III Conjugate described in Example 33. The reagents and methods for electrochemiluminescence are described in the previous example.

The fluorescence polarization assay used to measure the concentration of theophylline in the different serum samples was carried out using an automated TDX instrument from Abbott Laboratories (North Chicago, Ill.). Hemolyzed, lipemic, icteric and normal sera were used in the assays and data for the abnormal sera are listed in Table XVI below.

TABLE XVI

Homogeneous Theophylline Assay
Characteristics of Potentially Problematic Sera

| Serum | Factor Concentration | Normal Range |
|---|---|---|
| Hemolyzed | 12.4 mg/dl hemoglobin | 0–3.2 mg/dl |
| Lipemic | 405 mg/dl triglycerides | 10–190 mg/dl |
|  | 196 mg/dl cholesterol | 120–200 mg/dl |
| Icteric | 10 mg/dl bilirubin | 0–1.5 mg/dl |

Figure 3:
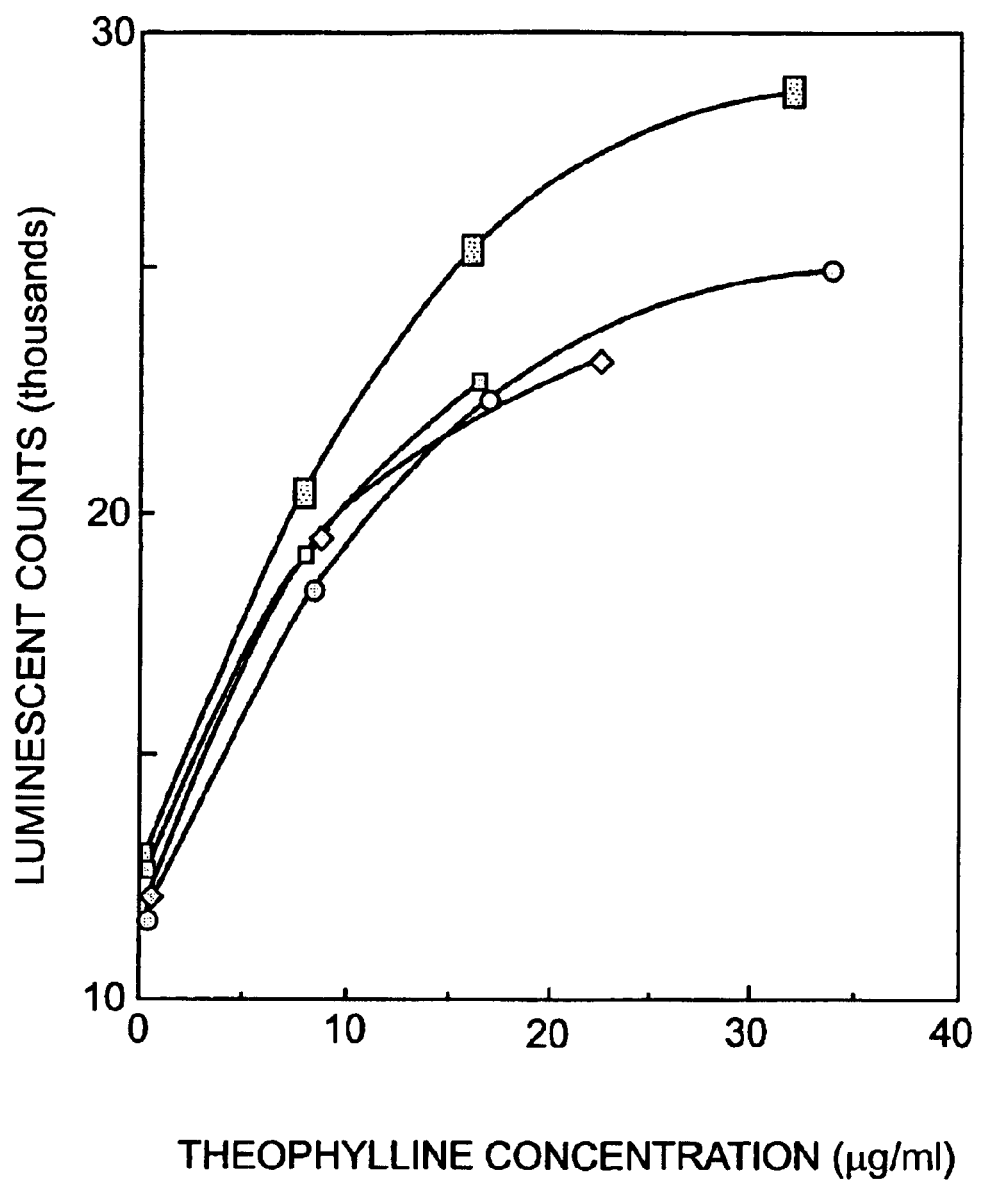
FIG. 3 graphically depicts the results of a homogeneous theophylline assay in various sera.

Different amounts of theophylline were added to the serum samples to give final concentrations between 2.5 micrograms theophylline/ml and 40 micrograms theophylline/ml. The results for the homogeneous electrochemiluminescent immunoassay are displayed in FIG. 3.

Each serum sample was also analyzed for the concentration of theophylline by a fluorescence polarization assay. The concentration of theophylline measured by the homogeneous electrochemiluminescence immunoassay and the fluorescence polarization assay were compared. The data were plotted as a scattergram and are shown in FIGS. 4A–D. The data points were analyzed by linear regression and the correlation coefficients were calculated. The analysis demonstrates an excellent correlation between the two assays. The correlation coefficients (r) were between 0.98 and 1.00. The slopes of the curves for normal, hemolyzed, and lipemic serum samples were between 0.8 and 1.2, demonstrating excellent recovery of theophylline from these serum samples.

Although the electrochemiluminescence emitted by the icteric serum samples containing theophylline was higher than for the other serum samples, it was proportionally higher at each theophylline concentration. This can be seen in FIG. 4D. The correlation coefficient is 1.00 for the data points comparing electrochemiluminescence and fluorescence polarization, however, the slope is 2.14, demonstrating higher recovery for the theophylline in the icteric serum sample.

Based on these results, the concentration of theophylline in an icteric sample may be determined by establishing a standard curve for the sample by adding known amounts of the Ru(II)-Compound Conjugate to aliquots of the icteric serum. These data demonstrate that a homogeneous electrochemiluminescent immunoassay may be used to measure the concentration of theophylline present in serum samples containing abnormal levels of hemoglobin, lipid and bilirubin.

A homogeneous electrochemiluminescent immunoassay offers advantages over a fluorescence polarization method because of the versatility of ECL detection, e.g., more sensitive detection at higher concentrations of biological molecules.

A homogenous electrochemiluminescent immunoassay offers further advantages over a fluorescence polarization method because no incident light source is required; electrical excitation being the only requirement for efficient light-generation. Consequently, no sophisticated optics are necessary. Since the measurement principle is purely specific photon emission induced by electrochemical stimulation, the sensitivity of the system is potentially much greater than fluorescence polarization and a wider dynamic range will be achievable. Also, measurement of a much greater variety of analytes is possible with a homogeneous electrochemiluminescent immunoassay than is provided by the fluorescence polarization technique, due to the selective modulation of electrically-stimulated chemiluminesence by biomolecular recognition events, e.g., antibody-antigen interactions.

Based on these results, one skilled in the art would know that homogeneous electrochemiluminescent immunoassays for detecting other analytes of interest in abnormal serum samples may be developed.

EXAMPLE 37

Assay for Theophylline in Serum Based on a Homogeneous Electrochemiluminescence Immunoassay and Comparison to a High Pressure Liquid Chromatographic (HPLC) Method Different amounts of theophylline were added to human serum samples to give final concentrations between 2.5 micrograms theophylline/ml and 40 micrograms theophylline/ml. Each sample was then divided into two aliquots and the concentration of theophylline in the sample was determined by a homogeneous electrochemiluminescence immunoassay and compared to the results obtained for the same serum samples using an HPLC method. The format for the homogeneous electrochemiluminescence immunoassay was a competitive binding assay using a monoclonal antibody specific for theophylline and the Ru(II)-Compound III Conjugate. The reagents and methods for this assay are described in a previous example. The HPLC method used to measure the concentration of theophylline in different serum samples is described as follows.

Theophylline (1,3-dimethylxanthine) was separated from serum proteins by precipitation of the latter with acetonitrile. The supernatant fluid containing theophylline was run on an HPLC system equipped with a Waters Associates Micro Bondapak C18 column, (3.9 mm×30 cm). The chromatogram was completely resolved in less than 10 min.

The following reagents were used: sodium acetate (reagent grade), deionized water (purified by the Millipore Milli Q* system), acetonitrile (HPLC grade) and theophylline standard, (Sigma). The solvent used for precipitating the serum proteins was a 20 mM sodium acetate buffer, pH 4.0, containing 14% (v/v) acetonitrile. The HPLC mobile phase buffer was 10 mM sodium acetate buffer, pH 4.0, containing 7% (v/v) acetonitrile. The flow rate was 1.5 ml/min, and the eluant was monitored by a UV spectrophotometer set at 270 nm. The sensitivity of the UV absorbance detector was set at 0.02 Absorbance Units Full Scale (AUFS). The ambient temperature ranged typically between 22° C. and 24° C.

The results for the homogeneous electrochemiluminescent immunoassay and the HPLC assay for determining the concentration of theophylline in serum are shown in FIG. 5. The data were plotted as a scattergram and the data points were analyzed by linear regression. The correlation coefficient was calculated. The correlation coefficient (r) was 0.98, which demonstrates excellent correlation between the two assays.

The slope of the curve was 1.197, demonstrating excellent recovery of the theophylline from the serum sample for the homogeneous electrochemiluminescent immunoassay compared to a standard method based on HPLC. The homogeneous electrochemiluminescence assay offers advantages over the HPLC method because of the speed, sensitivity and ability to easily handle multiple samples. Based on these results, one skilled in the art would know that homogeneous eleetrochemiluminescent immunoassays for detecting analytes of interest, which may be detected by HPLC and similar methods, may be developed.

EXAMPLE 38

Preparation of Theophylline-Bovine Serum Albumin Conjugates

Theophylline-bovine serum albumin (BSA) conjugates were prepared from theophylline-3-methyl-butyric acid, theophylline-8-butyric acid and theophylline-7-acetic acid by the following procedure. 50 mg of BSA were dissolved in 1.5 ml of 0.15M $NaHCO_3$, pH 9.0. Separately, 16 mg of ethyl 3'3-dimethyl amino propyl carbodiimide hydrochloride (EDCI), 11 mg N-hydroxy succinimide (NHS) and either 17.8 mg of theophylline-7-acetic acid, 20 mg of theophyllic-8-butyric acid or 20.9 mg of theophylline-3-methyl-butyric acid dissolved in dimethylsulfoxide were added and the solution heated at 45° C. for 1–2 hrs. The solution was added to the BSA solution dropwise and allowed to react for 1 hr. Theophylline conjugates of BSA were purified by gel filtration chromatography on a Sephadex G-25 column (1.6 cm×38 cm) using 0.15 M PBS/0.1% azide, pH 7.4, as the mobile phase and a flow rate of 30 ml/hr.

EXAMPLE 39

Preparation of Theophylline-BSA Biomag* Particles

A 4 ml volume of Biomag*-amine particles (Advanced Magnetic, Inc., Cambridge, Mass.) was washed 2–3 times in separate T-flasks with 20 ml of phosphate buffered saline (Sigma) (PBS), pH 7.4, containing 0.008% Nonidet P-40 (NP-40). To the Biomag* wet cake, 10 ml of 5% glutaraldehyde (Sigma) in PBS was added and activation was allowed to proceed for 3 hrs using a rotary mixer. The activated Biomag* particles were washed as described above for a total of 4 washes and transferred to a T-flask.

6.8 mg of theophylline-BSA prepared as described in Example 38 in 10 ml of PBS/NP-40 were added to the activated Biomag* wet cake. The reaction was allowed to proceed overnight at 4° C. with mixing.

The activated Biomag* wet cake was washed 3 times with 20 ml of 1% BSA/0.15M PBS/0.1% azide (pH 7.4), the first wash lasting for approximately 30 min using a rotary mixer.

EXAMPLE 40

Preparation of Compound I-Anti-Theophylline Conjugate 1.1 ml of a mouse anti-theophylline monoclonal antibody (Kallestad, lot no. WO399; 4.6 mg/ml) were centrifuged at 10,000 g for 8 min. The buffer was exchanged with 0.2M $NaHCO_3$, 0.15 M NaCl, with azide, pH 9.0, using an Amicon Centricon* 30 concentrator (centrifuged at 3000× g). The antibody solution was diluted to 2 ml and 3.2 mg of Compound I were added. The reaction was allowed to proceed for 2 hrs at room temperature with stirring and 79 microliters of aqueous $NaBH_4$ at 1 mg/ml was added and the solution stirred for 30 min.

The resulting solution was loaded onto a Sephadex G-25 (1.0 cm×18.0 cm) previously equilibrated with tris buffer and eluted at a flow rate of 15 ml/hr. The fractions containing the Compound I-anti-theophylline conjugate were pooled, transferred to dialysis tubing, and dialyzed against 0.15M phosphate/0.15 M NaF (PBS), pH 6.9 (4 1).

EXAMPLE 41

Assay for Theophylline in Serum Based on a Heterogeneous Electrochemiluminescent Assay Using an immunometric assay format, a heterogeneous assay for theophylline was developed using a Compound I labeled anti-theophylline antibody and theophylline BSA immobilized on Biomag* magnetic particles. The antibody concentration was 20 micrograms/ml. The magnetic particle concentration was 1% solids (wt/vol). Theophylline was added to a final concentration of 10 and 40 micrograms/ml of serum. The theophylline serum standards were diluted 1000 fold in PBF Buffer (sodium phosphate buffer, pH 7.0, 0.1 M sodium fluoride) containing 0.1% BSA.

The assay was performed by the addition of 75 microliters of the diluted serum standards to 75 microliters of antibody conjugated to Compound I and incubating the solution at room temperature for 20 min. Then 50 microliters of the theophylline-BSA-Biomag* particles were added and the suspension was allowed to stand for 5 min. The particles were separated magnetically and 100 microliters of the supernatant was measured for electrochemiluminescence as described in Examine 48.

| Theophylline Concentration micrograms/ml[++] | ECL* | SD | % CV |
|---|---|---|---|
| 0 | 8,758 | 81 | 0.9% |
| 10 | 11,078 | 368 | 3.0% |
| 40 | 14,106 | 674 | 4.8% |

*ECL counts per 10 seconds
[++]corrected for dilution

Based on these results, one skilled in the art would be able to develope a heterogeneous electro-chemiluminescence immunoassay for other analytes of interest in a biological matrix.

EXAMPLE 42

Preparation of a Compound II-Digoxigenin Conjugate 100.2 mg (0.104 mmol) of Compound II, 41 mg (0.105 mmol) of digoxigenin (Sigma) and 28 mg (0.136 mmol) of 1,3-dicyclohexylcarbodiimide (DCC) were added to a 50 ml round bottom flask equipped with a stirbar. To the resulting mixture were added 8–10 ml of anhydrous pyridine (Aldrich Sure-Seal) using a syringe with an 18 gauge needle. The flask was stoppered, sealed with Teflon tape and the contents gently stirred to yield a red solution. The flask was allowed to stand in the dark with stirring in the hood for 24 hrs, at which time 6 mg (0.015 mmol) of digoxigenin and 20 mg (0.097 mmol) of DCC were added. The solution was capped and allowed to stir at room temperature in the dark. The next day no evidence of dicyclohexyl urea precipitation was observed. An additional 18 mg (0.05 mmol) digoxigenin and 103 mg (0.50 mmol) DCC were added. The flask was resealed and stirring continued in the dark. After 72 hrs an additional 103 mg of DCC were added and the solution stirred in the dark for 3 hrs.

5–10 drops of $H_2O$ were added to the solution, which was then stripped to dryness on a rotary evaporator in the dark to produce a red solid.

The resulting red solid was covered with aluminum foil and dried overnight under vacuum over $CaSO_4$ in a dessicator. The dried solid was then dissolved in 3–5 ml of methanol and approximately 0.25 g of anhydrous solid $LiClO_4$ were added to the mixture. Once the $LiClO_4$ was dissolved, the solution was loaded onto a Sephadex LH-20 column (75 cm×19 mm) and eluted with methanol at a flow rate between 7–10 sec/drop.

Three bands were noted as the chromatography proceeded; a pale orange (red luminescent) first band (Fraction 1); a dark red second band that represented the major portion of the reaction (Fraction 2); and a third band which trailed the first two bands (probably unreacted starting material) which was discarded.

Because bands 1 and 2 just barely separated on the column, any orange product in band 2 was isolated by dripping a methanol solution of Fraction 2 (15 ml) into approximately 300 ml of dry diethyl ether (stirred). The resulting precipitate was collected by suction filtration on a 15 ml medium frit and washed five times with 15 ml of diethyl ether. Residual ether was removed by drying the complex overnight over $CaSO_4$ in a vacuum desiccator. This solid material was determined to be various concentrations of digoxin antibody and 100 microliters of Compound II-Digoxigenin conjugate (150 nM). Tubes were mixed on a vortex and incubated at room temperature for 15 min. Following incubation, 100 microliters of ECL solution (previously described) were added and electrochemilumescence was measured.

Results:

| Specific Antibody Concentration microgram/tube | x ECL Signal |
|---|---|
| 0.1 | 108000 |
| 1 | 114000 |
| 5 | 82500 |
| 10 | 64000 |
| 20 | 52000 |
| 40 | 36000 |

Total ECL Counts for 30 nM Compound II-Digoxigenin Conjugate 113666 (peak height)

At a concentration of 40 micrograms/tube, non-specific antibody modulation of signal was 67,000 counts compared to 36,000 counts in the presence of a specific antibody to digoxin.

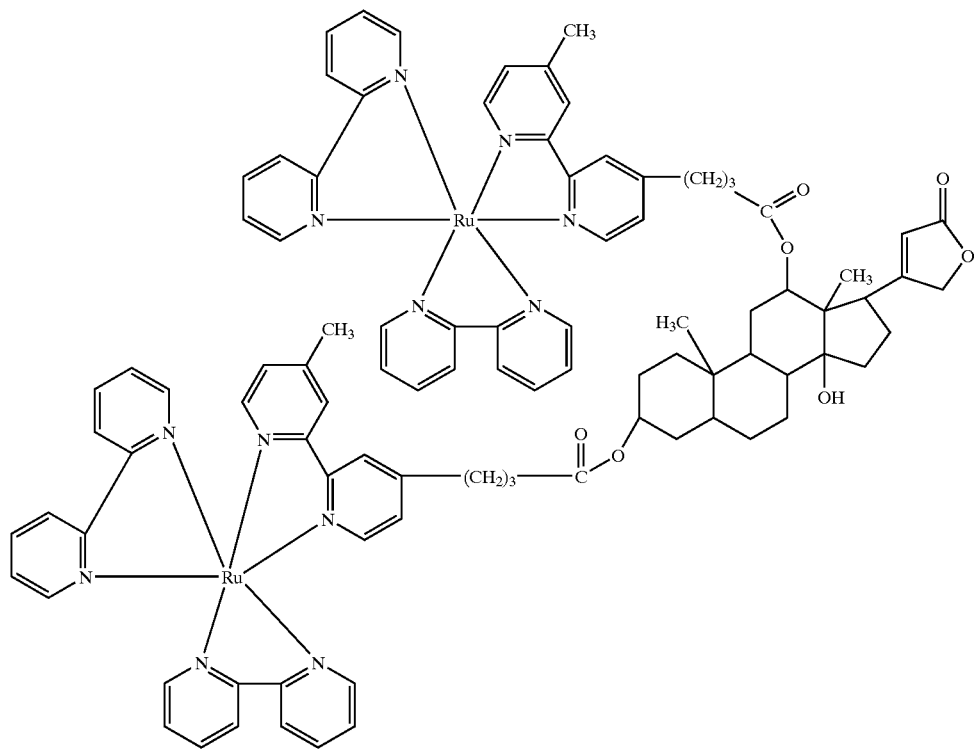

EXAMPLE 43

Electrochemiluminescence (ECL) of Compound II-Digoxigenin Conjugate: Modulation of ECL Signal by Anti-digoxin Antibody Monoclonal antibody to digoxin was diluted to the following concentrations in immunoassay buffer:
1, 10, 50, 200, 400 micrograms/ml
Compound II-Digoxigenin Conjugate (50 micromolar) was diluted to 150 nM in immunoassay buffer (0.1M phosphate buffer, pH 6.0, containing 0.1M sodium fluoride).
To 200 microliters of immunoassay buffer in polypropylene tubes (12 mm×75 mm) were added 100 microliters of As can be seen from FIG. 6, an increasing concentration of anti-digoxin antibody when reacted with a fixed concentration of Compound II-Digoxigenin Conjugate showed increasing modulation of the electrochemiluminescent signal. This characteristic may be used advantageously to develop a homogeneous electrochemiluminescence based assay for the measurement of digoxin in serum or plasma.

EXAMPLE 44

Homogeneous Digoxin Assay

Based on the results described in Example 43, a homogenous electrochemiluminescent immunoassay for digoxin may be developed using antibody to digoxin and the Compound II-Digoxigenin conjugate using a competitive binding assay format. The reagents which may be used have been described in Example 43. For this assay, a specific concentration of monoclonal antibody to digoxin would be chosen. The antibody concentration may be between 75 to 100 micrograms per ml. The Compound II-Digoxigenin Conjugate concentrations may be between 5–15 nM (Final Concentration).

Digoxin Standard would be added to human serum to give a final concentration of 0.1, 0.5, 1, 2, 4, 8 and 16 nanograms of digoxin per ml of serum.

The assay may be performed by adding 10–30 microliters of serum to 300 microliters of anti-digoxin monoclonal antibody and holding the solution at room temperature of 30 min. Then 100 microliters of the Compound II-Digoxigenin conjugate may be added to each tube to give a final concentration within the range of 5 to 15 nM and incubating the solution at room temperature for 20 min. 100 microliters of the ECL solution previously described may be added to each tube and ECL may be measured as previously described.

EXAMPLE 45

Preparation of Oubain-Bovine Serum Albumin Conjugate 50 mg of oubain octahydrate (Aldrich) was dissolved in 5 ml of deionized $H_2O$. 81 mg of $NaIO_4$ was added to the dissolved oubain and the mixture was incubated for 2 hrs at room temperature. The reaction was stopped by passing the mixture over a Dowex IX-8 ion exchange resin column (5 ml) which had been equilibrated with deionized $H_2O$ until the pH was between 5 and 6. The oxidized oubain fraction was collected when the drops entering the waste container showed signs of mixing.

100 mg of crystalline, lyophilized bovine serum albumin (Sigma) (BSA) was dissolved in 5 ml of 0.1 M potassium phosphate buffered saline, pH 7.4, containing 0.05% azide. The oxidized oubain solution was added dropwise to the BSA solution with stirring. The resulting solution was allowed to react for 1 hr at room temperature before adding 30 mg of $NaCNBH_4$ (Aldrich). The solution was then stirred overnight at room temperature.

The solution was concentrated (11 ml to 4 ml) using polyethylene glycol-8000 and free oubain and excess borohydride were removed from the solution by gel filtration on Sephadex G-25 (column=0.6 cm×37 cm; eluant=0.1 M $K_2PO_4$/0.15M NaCl, pH 7.5, 0.05% Fractions 11–17 were pooled and the protein concentration determined by measuring absorbance at 280 nm (after dilution).

EXAMPLE 46

Preparation of Oubain-BSA-Sepharose 2 g of cyanogen bromide activated Sepharose 4B (Pharmacia) was washed with 400 ml of 1 mM HCl in 50 ml portions on a sintered disk funnel. The resin was then washed with 20 ml of 0.1M $NaHCO_3$, 0.5M NaCl buffer, pH 9.0 (coupling buffer). After transferring the resin to a polypropylene container, 30 mg of oubain-BSA dissolved in 15 ml of coupling buffer were added. The activated resin was allowed to react with the oubain-BSA for 2 hrs with rotary mixing. The remaining activated sites were reacted with 7 ml of 0.5M ethanolamine (pH 8.0) for 2 hrs at room temperature. Using a sintered disk funnel, the resin was subjected to 100 ml washes with each of the following solutions: 0.15M PBS; 1 mM HCl; couling buffer; coupling buffer; 0.2% NP-40 in PBS; and PBS. The resin was resuspended to 11 ml and a sufficient amount of this suspension was added to a 1.0 cm inside diameter column (Pharmacia) to give a total bed volume of 3.5 ml.

EXAMPLE 47

Preparation and Affinity Purification of an Anti-Digoxin-Compound I Conjugate 450 microliters of a 1 mg/ml stock solution of a mouse anti-digoxin monoclonal antibody (Cambridge Medical Diagnostics, cat. no. 200M-014, lot no. MA 2507F) were concentrated to 100 microliters using an Amicon Centricon 30° concentrating unit. To this concentrate were added 900 microliters of 0.2 M sodium bicarbonate buffer, pH 9.6 and 0.6 mg of Compound I. The reaction (amidation) was allowed to proceed at room temperature for 2 hours before 30 microliters of 1.0 M $NaBH_4$ (aq) (Sigma) was added. The resulting solution was allowed to stand for 1 hour.

Excess Compound I and other products were separated from the antibody conjugate by Sephadex G-25 chromatography (column=1.0 $Cm_{ID}$×18 cm; eluant=0.1 M phosphate buffered saline). The sample was fractionated in 1 ml portions at a flow rate of 20 ml/hr and the absorbance at 280 nm monitored at 2.0 AUFS and 0.5 AUFS.

Fractions 5, 6, 7 and 8 were pooled, loaded onto a prewashed oubain-BSA-Sepharose affinity column (3.5 ml column with 1 cm diameter), and eluted at a flow rate of 15 ml/hr. After unretained material was eluted, the flow rate was increased to 30 ml/hr until 20 ml of eluate were collected. The saline concentration of the mobile phase were increased to 0.5M and another 20 ml were eluted through the column.

Oubain specific anti-digoxin-Compound I conjugate was removed by addition of 4 M and 6 M KSCN. Fractions corresponding to anti-digoxin-Compound I conjugate were pooled and dialyzed against 10 mM phosphate buffered saline (4.1; pH 7.4) followed by 0.1 M phosphate buffer (4.1; pH 7.0).

EXAMPLE 48

Heterogeneous Electrochemiluminescent Immunoassay for Digoxin 10 mg of solid digoxin were dissolved in 10 ml of $DMSO:H_2O$ (8:2), to give a digoxin concentration of 1 mg/ml (hereinafter Stock Standard).

Working standards were prepared from the Stock Standard to the following concentrations in 0.15 M phosphate buffer, pH 7.0, containing 0.1% BSA and 0.15 M NaF (hereinafter ECL Buffer): 80 ng/ml, 40 ng/ml, 20 ng/ml, 10 ng/ml, 5 ng/ml and 0 ng/ml.

75 microliters of anti-digoxin-Compound I conjugate (diluted 1:90) and 75 microliters of the each standard were pipetted into a class tube, mixed on a vortex and incubated at room temperature for 20 min.

50 microliters of prewashed oubain-BSA-Biomag* particles were added to each tube, mixed on a vortex and incubated at room temperature for 5 min. Biomag* particles were separated and supernatant was transferred to a separate tube.

100 microliters of supernatant were mixed with 400 microliters of 0.125 M potassium phosphate 0.125 M citric acid; 32 mM oxalic acid; 1.25% Triton X-100 in a tube.

The sample was placed into a Berthold instrument and the electrochemiluminescence was measured as previously described except the procedure was modified by stepping the applied potential from open circuit to 2.2V and integrating the photon counts for 10 sec.

The electrode was cleaned between measurements using phosphate-citrate buffer as follows:
  (a) Pulse electrode using 3 sec intervals alternating between −2.2V and +2.2V for 1 min.
  (b) Poise the electrode at +2.2V for 10 seconds.
  (c) Rinse electrode with deionized water $H_2O$ and blot dry.

The results are shown in FIG. 7.

EXAMPLE 49

Labelling DNA with an Electrochemiluminescent Moiety

The following two methods have been used to label DNA with an electrochemiluminescent moiety.

Synthesis A 1.0 $A_{260}$ of the custom synthesized 38 mer (MBI 38)

TCACCAATAAACCGCAAACACCATCCCGTCCTGCCAGT* where T* is thymidine modified at carbon 5 with

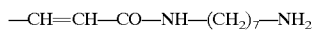

—CH=CH—CO—NH—$(CH_2)_7$—$NH_2$ were dissolved in 100 microliters of 0.01 M phosphate buffer, pH 8.7. 100 microliters of a solution of bis(2,2'-bipyridine)[4-(butan-1-al)-4'-methyl-2,2'-bipyridine] ruthenium (II) diperchlorate (Compound I) (2.3 mg in 300 microliters of 0.01 M potassium phosphate buffer, pH 8.7). The contents were stirred and allowed to stand at room temperature overnight.

100 microliters of a saturated aqueous solution of sodium borohydride was added to the mixture to convert the reversible imine Schiff's base linkage into nonreversable amine linkage. The reaction was allowed to run at room temperature for 2 hrs. The solution was then treated carefully with a few drops of dil. acetic acid to quench excess of sodium borohydride. The reaction solution was loaded onto a P-2 gel filtration column (18 inches×½ inch) which had been pre-equilibrated with 0.1 M triethylammonium acetate, pH 6.77. The column was eluted with the same buffer and 2 ml fractions were collected at a flow rate of 20 ml/hr. DNA eluted in fractions 9 and 10 were well separated fran unreacted ruthenium bipyridyl complex. The collected DNA sample exhibited typical UV absorption and additionally showed a fluorescent emission spectrum at 620 nm when excited at 450 nm. The fluoresent emission shows the presence of the ruthenium bipyridyl moiety in the DNA sample. The product travels as a single orange fluorescent band on polyacrylamide gel electrophoresis. The electrophoretic mobility of the labeled DNA (MBI 38-Compound I Conjugate) is approximately the same as the unlabeled DNA.

Synthesis B

The ruthenium complex was first converted into an N-hydroxysuccinimide derivative by dissolving 3 mg in 60 microliters of anhydrous dimethylformamide and treating it with a solution of N-hydroxysuccinimide (52 mg) in 200 microliters of anhydrous DMF in the presence of 94 mg dicyclohexylcarbodiimide (DCC). The reaction was allowed to proceed for 4 hrs at 0° C. Precipitated dicyclohexylurea was removed by centrifugation and the supernatant (200 microliters) was added to the solution of amino-linked DNA (described in Synthesis A) in 0.01 M phosphate buffer pH 8.77 ($2A_{260}$ in 100 microliters of buffer). The reaction was allowed to proceed overnight at room temperature. A considerable amount of solid appeared in the reaction which was removed by filtration through glass wool. The filtrate was concentrated and dissolved in 0.5 ml of 1 M triethylammonium acetate (pH 6.8). The reaction mixture was then chromatographed as described in Sythesis A. The labeled DNA exhibited all spectral and electrophoretic characteristics as discussed for the material prepared in Synthesis A.

EXAMPLE 50

Electrogenerated Chemiluminescent Properties of Labeled DNA

The labeled DNA sample from Example 49, Synthesis A (MBI 38-Compound I) was used to study its electrochemiluminescent properties. Various concentrations of labeled DNA were dissolved in 0.5 ml of 0.1 M phosphate buffer, pH 4.2, containing 0.1 M citrate, 25 mM oxalate and 1.0% Triton X-100 and measured on a modified Berthold luminometer. FIG. 8 shows the response of the electrochemiluminescent signal to various DNA concentrations.

EXAMPLE 51

Hybridization Studies of Compound I-labeled Oligonucleotide

The complementary strand to the 38 mer described in Example 50 was synthesized using the ABI model 380 B DNA Synthesizer and was designated MGEN-38.

To determine if the covalent attachment of Compound I to the oligonucleotide affected the hybridization properties of the MBI 38 oligonucleotide, the following experiment was devised. Various concentrations of the target fragment (MGEN-38) were spotted on a sheet of Gelman RP nylon membrane, fixed and probed with either MBI 38 or MBI 38-Compound I. Both fragments were treated with T4 polynucleotide kinase and gamma $^{32}$P[ATP] and labeled with $^{32}$P at the 5' end. The hybridization sensitivities of DNA and Compound I-labelled DNA were then compared.

Concentrations of MGEN-38 DNA, ranging from 50 ng down to 0.05 ng, were spotted on a nylon membrane and allowed to air dry. Duplicate membranes were set up. The blots were treated for 2 min each in: 1.5M NaCl-0.5M NaOH to fully denature the DNA; 1.5M, NaCl-0.5M TRIS to neutralize the blot, and finally in 2×SSC. The blot was baked in a vacuum oven at 800° C. for 2 hrs.

The hybridization probe was prepared as follows: 3 micrograms of MBI 38 and MBI 38-Compound I were kinased with 10 units of T4 kinase and 125 microcuries of gamma $^{32}$P-ATP). The percentage of isotope incorporation into DNA was determined and shown below.

| | |
|---|---|
| MBI 38 total count | $4.1 \times 10^6$ cpm/microliter |
| incorporated Counts | $3.1 \times 10^4$ cpm/microliter |
| % incorporation = 75.6% | |

| | |
|---|---|
| MBI 38-Compound I total count | 3.2 × 10⁶ cpm/microliter |
| incorporated count | 2.6 × 10⁵ cpm/microliter |
| % incorporation = 81.2% | |

Prehybridization and hybridization solutions were prepared according to Maniatis (24). Blots were prehybridized for 4 hrs at 53° C. with 50 micrograms/ml of calf thymus DNA. The blots were then placed in hybridization solution containing the respective probes at 10,000,000 cpm, and allowed to hybridize overnight (12 hrs) at 53° C. The following day, the blots were washed as follows:

twice with 2×SSC+0.1% SDS at 53° C. for 15 minutes each wash twice with 0.2×SSC+0.1% SDS (same as above)

twice with 0.16×SSC+0.1% SDS (same as above)

The blots were then air dried and exposed to Kodak X-omat* film at −70° C.

Analysis of the X-ray (see FIG. 9) showed that very similar hybridization patterns were observed between the MBI 38 and MBI 38-Compound I probe. In both cases hybridization of probe to 0.5 ng of target was observed, and faint traces of hybridization were observed down to 0.05 ng of target DNA. No hybridization activity by the probe was detected for the negative control DNA (phage lambda DNA spotted at 50 ng).

EXAMPLE 52

Compound I-labeled DNA Probe Hybridization Specificity Study

Genomic DNA from several *E. coli* and non-*E. coli* strains were isolated according to methods described by Maniatis (24). The organisms used were:

*E. coli* strain EC8—natural isolate
*E. coli* strain PC1A—enteropathogenic strain
*E. coli* strain 10H07—enterotoxigenic strain
*E. coli* strain EC50—natural isolate
*E. coli* strain B—lab strain
*E. coli* strain K12—lab strain
*Enterobacter aerogenes*
*Citrobacter freundii*
*Salmonella paratyphi* B
*Salmonella potsdam*

DNA from the above-mentioned strains were spotted in duplicate in 3 micrograms aliquots on a Gelman RP nylon membrane and on a S & S nitrocellulose membrane. For negative control, 50 ng of phage lamda DNA were spotted. Positive control consisted of various concentrations of the complementary strand, MGEN-38, ranging from 50 ng down to 0.5 ng. The blots were prepared and treated as described in Example 51.

The probing DNA consisted of 3.0 micrograms of the MBI 38-Compound I fragment which was T4 kinased with 125 microcuries of gamma $^{32}$P-ATP to incorporate radioactivity. The following amount of activity was incorporated.

MBI 38-Compound total counts—3.35×106 cpm/microliter
incorporated counts—1.50×10⁶ cpm/microliter
% incorporation—44.7%

For this assay, 2,600,000 cpm of activity was used for probing each filter. The hybridization solutions, conditions, washing solutions and protocols were the same as those described in Example 51.

The X-ray film of the blot (FIG. 10) shows that both the positive and negative controls reacted accordingly. No hybridization activity was detected with lambda DNA (50 ng), and strong hybridization was observed for the complementary sequence, MGEN-38, down to 0.5 ng concentration. These findings are in total agreement with the results of the sensitivity study.

EXAMPLE 53

Preparation of 2,2'-bipyridinium-hexachloroosmate (VI)

1.01 g of ammonium hexachloroosmate (VI), $(NH_4)_2OsCl_6$ (Alfa) (1.00 equivalents) were dissolved in 50 ml of 3N HCl (aq) at 70° C. To the hot, stirred solution was added dropwise a solution of 2,2'-bipyridine in 3N HCl (aq). A red salt,

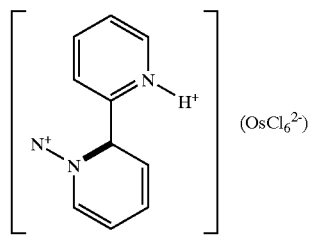

(hereinafter $(bpyH_2^{2+})OsCl_6^{2-}$), with a molecular weight of 562.2 g/mole, precipitated from the solution.

Precipitation was completed by cooling the solution at 0° C. in an ice bath for 2 hrs. The product was collected by suction filtration on a glass fritted filter. The precipitate was washed successively with 5–10 ml portions of ice cold 3N HCl (aq) and water. After a final washing with 20 ml of anhydrous diethyl ether, the product was dried at 70° C. under vacuum for 48 hrs. Yield=1.01 g orange powder (78% based on $(NH_4)_2OsCl_6$). The product was used without further purification.

EXAMPLE 54

Preparation of 2,2'-bipyridine-tetrachloroosmate (VI)

0.9 g (1.60 mmol) of the $(bpyH_2^{2+})(OsCl_6^{2-})$ salt prepared in Example 53 was weighed into a pyrex test tube. The test tube was placed into a pyrex furnace tube fitted with an argon inlet and outlet and a thermometer (400° C. max. reading).

The entire assembly was placed in a tube furnace and flushed with argon. The furnace was activated and brought to a temperature of 270–300° C. A slow stream of argon was passed through the tube throughout the reaction. The argon outlet was vented into the fume hood to carry HCl produced during the reaction out of the laboratory. As the temperature approached 270° C., pyrolysis of the reactant began. HCl gas was observed to evolve from the solid. Vigorous evolution of HCl was observed for 30 min and then slowly began to subside. After 6 hrs the oven was shut off and the sample cooled to room temperature. The product $(bpy)OsCl_4$, a finely divided red-brown solid, was purified by suspension in a stirred 3N HCl (aq) solution for 12 hrs followed by suspension for 6 hrs in stirred anhydrous diethyl ether. Isolation of the product via suction filtration on a glass fritted filter gave 0.75 g (95%) yield of 2,2'-bipyridinetetrachloroosmate (VI), hereinafter (bpy)OsCl$_4$, (MW= 489.3 g/mole).

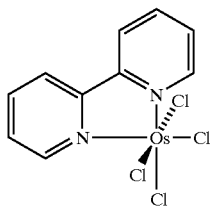

The product was used without further purification.

EXAMPLE 55

Preparation of cis-(2,2'-bipyridine)[cis-bis(1,2-diphenylphosphino)ethylent]-dichloroosmium (II)

Into a 50 ml round bottom flask equipped with a stirbar and reflux condenser were added 230 mg (0.47 mmol) (bpy)OsCl$_4$ prepared as in Example 54 and 465 mg (1.17 mmol) cis-bis(1,2-diphenylphosphino)ethylene (DPPene). 25 ml diglyme were added and the contents were refluxed under an argon atmosphere for 5 hrs. The dark green-black solution was cooled to room temperature under argon atmosphere and transferred to a 200 ml beaker. Addition of 80 ml anhydrous diethyl ether gave a dark green precipitate. The precipitate was collected by suction filtration on a glass fritted filter (medium porosity) and washed with five 20 ml portions of anhydrous diethyl ether. The precipitate was then dissolved in 15 ml CH$_2$Cl$_2$ to give a forest green solution. The solution was allowed to gravity drip through a glass fritted filter (medium porosity) into approximately 300 ml stirred anhydrous diethyl ether. Precipitation of the gray-green cis-(2,2'-bipyridine)[cis-bis(1,2-diphenylphosphino)ethylene-dichloroosmium II complex, hereinafter cis-(bpy)(DPP-ene)OsCl$_2$), occurred. The complex was collected by suction filtration on a glass fritted filter (medium porosity). The product was washed quickly with 20 ml cold 1:2 v/v ethanol/water followed by seven 30 ml portions of diethyl ether. The slate-gray powder was dried over CaSO$_4$ overnight in the vacuum desiccator.

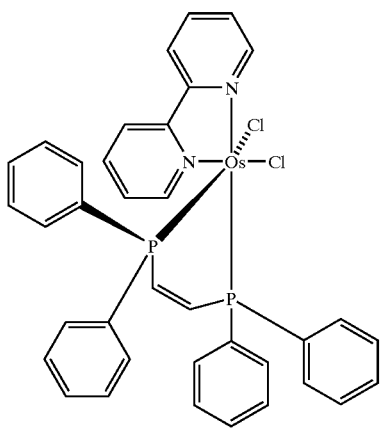

Yield: 240 mg (63% based on (bpy)OsCl$_4$; MW=814.4 g/mole. The product was used without further purification.

EXAMPLE 56

Preparation of (2,2'-bipyridine)[cis-bis(1,2-diphenylphosphino)ethylene{2-[3-(4-methyl-2,2'-bipyridine-4'-yl)propyl]-1,3-dioxolane}osmium (II) dichloride Into a 100 ml round bottom flask equipped with stirbar and reflux condenser were added 129 mg (0.158 mmol) cis-(bpy) (DPPene)OsCl2 prepared as in Example 55 and 0.3 g (1.0 mmol) of 2-[3-(4-methyl-2,2;-bipyridine-4-yl)propyl]-1,3-dioxolane, i.e., bpyoxal. To this was added 15 ml ethylene glycol. The suspension was refluxed under an argon atmosphere for 3 hrs. After cooling to room temperature, 10 ml H$_2$O were added to the contents of the flask.

A column (30 cm height×19 mm i.d.) of SP-Sephadex C-25 ion exchange resin in water was prepared. The contents of the reaction flask were loaded onto the column. The column was eluted with H$_2$O (approximately 500 ml) to remove ethylene glycol and excess bpyoxal ligand elution with 0.25 NaCl (aq) solution separated a small pale yellow band (orange fluorescence under long wave UV light) followed by a non-luminescent olive green band. These bands represented side-products of the reaction. No attempt was made to identify them and they were discarded. Once these bands were removed from the column, elution with 0.5M NaCl (aq) was begun. Three bands were eluted. The first, an orange band with orange luminescence, was identified as the chloride salt of the desired product moiety, (2,2'-bipyridine)[cis-bis](1,2-diphenyl phosphino)ethylene)2-[3-(4-methyl-2,2'-bipyridine-4'-yl)propyl-1]-1,3,-dioxolane osmium (II), hereinafter (bpy) (DPPene) (bpyoxal) Os (II)$^{2+}$. It separated cleanly from a trailing yellow band (green luminescence) and brown band (non-luminescent).

The volume of solution in the fraction (approximately 400 ml) containing the (bpy) (DDPene) (bpyoxal) Os (II)$^{2+}$ was reduced by evaporation to approximately 50 ml on a rotary evaporator. The aqueous NaCl concentrate was then extracted with three 50 ml portions of CH$_2$Cl$_2$. The CH$_2$Cl$_2$ extracts were combined, dried over anhydrous Na$_2$SO$_4$, and gravity filtered through a fluted filter paper. The red CH$_2$Cl$_2$ solution was concentrated to a volume of 10 ml by evaporation on the rotary evaporator. The complex was isolated as an orange solid by slowly dripping the CH$_2$Cl$_2$ solution into 200 ml of well-stirred petroleum ether. The precipitated complex was collected by suction filtration on a glass fritted filter (medium porosity). The product was washed three times with 15 ml portions of diethyl ether. The product was dried over CaSO$_4$ overnight in the vacuum desiccator.

Yield: 110 mg of (bpy) (DPPene) (bpyoxal) Os (II)$^{2+}$ (Cl$^-$)$_2$ *2H$_2$O (63% based on cis-(bpy) (DPPene)OsCl$_2$).

The product is a dihydrate and is analytically pure: C$_{57}$H$_{54}$N$_4$O$_4$P$_2$Cl$_2$Os*2H$_2$O (MW=1109.59 g/mole).

Theory: C, 55.20%; H, 4.87%; N, 5.05%; O, 5.77%; Cl, 6.39%. Found: C, 56.03%; H, 5.18%; N, 4.88%; O, 6.87%; Cl, 7.07%.

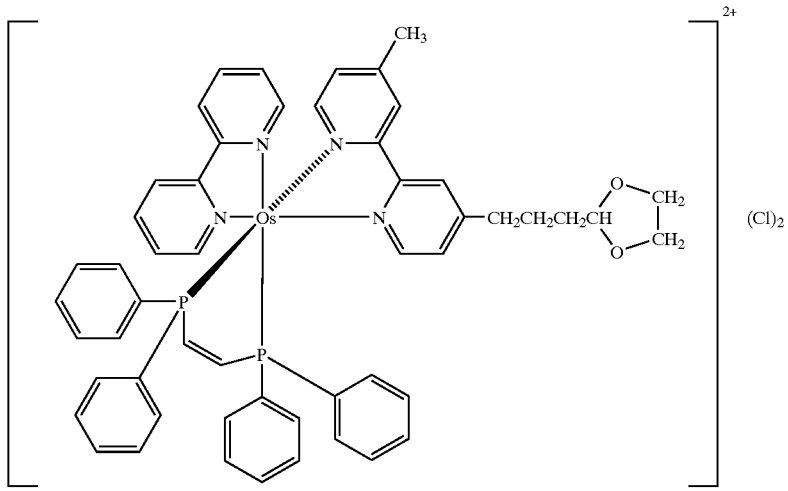

EXAMPLE 57

Preparation of cis-dichloro-bis-[4,4'carbomethoxy)-2,2'-bipyridine]ruthenium (II)

Into a 250 ml round bottom flash equipped with stirbar and reflux condenser were added 750 mg (1.55 mmol) of cis-tetra-(dimethylsulfoxide)dichlororuthenium (II) (Ru(DMSO)$_4$Cl$_2$) and 100 ml ethylene glycol. The contents of the flask were brought to a gentle boil under argon atmosphere and 756 mg (3.09 mmol) of (4,4'carbomethoxy)-2,2'-bipyridine were added. Heating under argon was continued for 5 min. The orange solution became brown/black and 0.75 g of lithium chloride and 50 ml ethylene glycol were added. The solution was heated for another 10 min. After cooling to room temperature, approximately 100 ml H$_2$O were added to the mixture. The mixture was extracted with five 200 ml portions of CH$_2$Cl$_2$.

The CH$_2$Cl$_2$ extracts were washed with six 200 ml portions of water. The water layers were tested for fluorescence (red) after each washing and washing was continued if necessary until no fluorescence could be detected in the aqueous layer. The CH$_2$Cl$_2$ extracts were dried over anhydrous Na$_2$SO$_4$. The product was isolated by evaporation of the CH$_2$Cl$_2$ solution of the product into a stirred 10-fold volume excess of anhydrous diethyl ether. The precipitated product was collected by suction filtration, washed once with 30 ml diethyl ether and dried over CaSO$_4$ overnight in a vacuum desiccator. Yield=25% dark metallic green crystals.

The product is analytically pure.

Theory: C, 44.57; H, 4.01; N, 7.43; Cl, 9.40; O, 21.2.
Found: C, 44.16; H, 3.72; N, 7.11; Cl, 9.53; O, 20.15.
MW=754.5 g/mole.

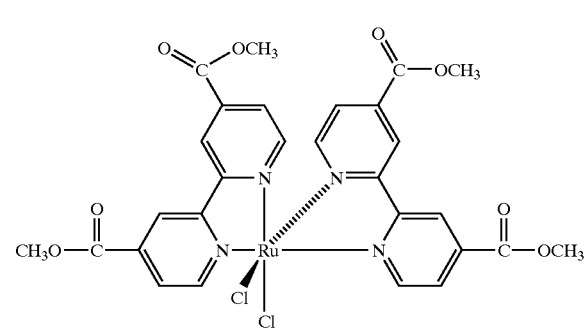

EXAMPLE 58

Preparation of bis[(4,4'-carbomethoxy)2,2'-bipyridine)2-[3-(4-methyl-2,2'-bipyridine-4-yl) propyl]-1,3-dioxolane ruthenium (II) diperchlorate To 250 mg of bis(4,4'-dicarbomethoxy-2,2'-bipyridine) ruthenium (II) dichloride (0.33 mmol) in 50 ml methanol/water (1:1) were added 105 mg (0.37 mmol) of 2-[3-(4-methyl-2,2'-bipyridine-4'-yl)-propyl)]-1,3-dioxolane (bpyoxal) and the mixture was refluxed for 12 hrs under an argon atmosphere. The solution was cooled and 0.5 ml of 70% HClO$_4$ were added. The methanol was slowly evaporated. Red crystals precipitated and were collected on a fritted funnel, washed with a small amount of cold water followed by ethanol and ether and dried to vacuo. Similar methods were used to prepare complexes from bis(4,4'-dicarbomethoxy-2,2'-bipyridine)ruthenium (II) dichloride and either 4-(4-methyl-2,2'-bipyridine-4'-yl)-butyric acid or 4-4'-methyl-2,2'-bipyridine.

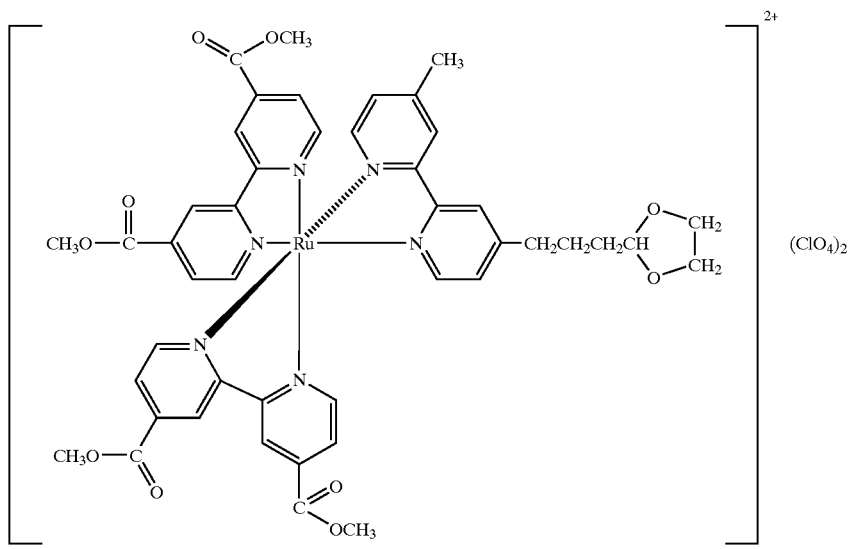

EXAMPLE 59

Compound I Labeling of Human IgG 2 ml of human IgG (2.5 mg/ml) were dialyzed against 2 liters of 0.2M sodium bicarbonate buffer, pH 9.6, overnight at 4° C. with gentle stirring. Compound I was prepared in a 100 molar excess to protein present (2.7 mg/100 microliters dimethylformamide) and allowed to dissolve. The dialyzed protein was added dropwise to the tag-aldehyde while gently stirring at room temperature for 2 hrs. A 100 molar excess (to protein) of sodium borohydride (100 microliters of a 1.24 mg/ml solution in deionized water) was added to the solution and gently stirred for an additional 30 min at room temperature. The conjugate was loaded onto a Sephadex G-25 column (1.0 cm×18.0 cm) equilibrated at room temperature with 0.2M Tris, pH 8.0, and the eluant was monitored at 280 nm. The void volume peak was collected, pooled, and dialyzed against 2 liters of the Tris buffer. The conjugate was tested for immunological activity by standard ELISA methods, and stored at 4° C. until used.

EXAMPLE 1

Biomag*/Goat-Anti-Human IgG Particle Preparation

A 2.5 ml aliquot of 5% Biomag*-amine terminated particles (Advanced Magnetics, Cambridge, Mass.) was transferred to a clean T-flask and washed 5 times with phosphate buffered saline (PBS). The wet cake was resuspended in 12.5 ml of 5% fresh glutaraldehyde (Sigma) and rotated end-over-end at ambient temperature for 3 hrs. The wet cake was transferred to a second T-flask and washed 3 times with PBS. The activated particles were resuspended to 12.5 ml with PBS, and transferred to a 15 ml centrifuge tube. To this suspension were added 12.5 mg of goat anti-human IgG 15 (H+L) (Jackson Labs) in 2 ml of PBS. The tube was rotated end-over-end for 3 hrs at room temperature and then overnight at 4° C. The next day the particles were washed 2 times with PBS containing 1% (w/v) bovine serum albumin (BSA) followed by storage in 12.5 ml of PBS containing 0.1% BSA at 4° C. until use.

EXAMPLE 61

Pseudo-Homogeneous Human IgG Electrochemiluminescence Assay Using Biomag* Magnetic Based Particle Assay Compound I-human IgG conjugate was diluted 1:50 in 0.15M phosphate buffer containing 0.1% BSA and aliquoted at 250 microliters/tube. 150 microliters of diluent (PB w/BSA as above) were added per tube, followed by the addition of either various dilutions of analyte (human IgG) or diluent (negative controls). Additionally, a non-specific analyte (goat anti-rabbit IgG) was used in some tubes to check for assay specificity. 50 microliters of 1% Biomag* coupled with goat anti-human IgG (H&L) were added to each tube. The tubes were mixed on a vortex and incubated at room temperature for 15 min with gentle shaking. The particles were magnetically removed from solution and 100 microliters of the resulting supernatant were transferred to a Berthold tube to which 400 microliters of a citrate-oxalate-Triton X-100 solution were added. The tube was mixed on a vortex and read in a modified Berthold luminometer fitted with an R-268 photomultiplier tube and a 0.29 inch diameter circular 52 gauge double platinum mesh electrode supported by a conductive paint covered polycarbonate support and connected to the voltage source through a 0.01 inch diameter platinium wire/silver paint contact. The potential applied was stepped from +1.4 to +2.15 V while a 10 second integration, was done. Between readings the electrode was electrochemically cleaned by rinsing with deionized water, then immersing in 0.1M phosphate-citrate buffer containing oxalic acid and Triton X-100 and stepping the applied potential from −2.2V to +2.2V (with 3 seconds at each potential) for 2 min and 20 seconds followed by pausing the potential at +2.2V for 10 seconds. The electrode was removed from the cleaning solution, rinsed with deionized water and blotted dry with an absorbent wiper. In this format the electrochemiluminescent signal was directly proportional to the analyte concentration.

EXAMPLE 62

Preparation of bis(2,2'-bipyridine) maleimidohexanoic acid, 4-methyl-2,2'-bipyridine-4'-butylamide ruthenium (II) diperchlorate: Compound IV 4-[4-(1-aminobutyl)])-4'-methyl-2,2'-bipyridine, prepared as described in Example 32 from 500 mg ($1.35 \times 10^{-3}$ mol) of pthalimide, was dissolved in 5 ml of dry pyridine with 0.313 g ($1.48 \times 10^{-3}$ mol) of maleimide hexanoic acid and 0.306 g ($1.48 \times 10^{-3}$ mol) of DCC. After storing overnight, the dicyclohexylurea was filtered off and the pyridine was stripped under vacuum. The residue was purified by column chromatography (activity II alumina, 5% MeOH/$CH_2Cl_2$) to give the purified product. Yield: 0.56 g (95%).

100 mg ($2.3\times10^{-4}$ mol) of maleimido-hexanoic acid, 4-methyl-2,2'-bipyridine-4'-butylamide and 100 mg ($2.06\times10^{-4}$ mol) of bis-(2,2'-bipyridine)ruthenium dichloride dihydrate were dissolved in 50 ml of ethanol/water (1:1), degassed with argon and refluxed for 4 hr. The resulting clear orange solution was diluted with 25 ml of solid $NaClO_4$, 25 ml of ethanol and 25 ml of acetone, and slowly evaporated under vacuum. When dry, another 25 ml of water and 25 ml of acetone were added and the solution was rotoevaporated to about 15–20 ml. The precipitated solid was collected, washed with water and dried. The sample was purified by preparative TLC on alumina using 1:9 methanol/choloroform. The fast running band was isolated by scraping off the plate and eluting the compound by stirring in methanol/chloroform (1:1). After filtration to remove the alumina, the orange solution was evaporated to dryness to give 86.7 mg of purified compound (72%). The structure was confirmed by NMR.

EXAMPLE 63

Labeling of hCG Peptide with Compound IV 2 mg of human chorionic gonadotropin (hCG) peptide (#109-145, JP141, Vernon Stevens, Ohio State University) were suspended in 1 ml of 0.15M citrate buffer, pH 6.0, and 1.13 mg of Compound IV were dissolved in 300 microliters of dimethylformamide. The peptide solution was added dropwise to the Compound IV solution over a one minute period. The solution was stirred gently at room temperature for 1 hr. The sample was then loaded onto a Bio-Gel P-2 column (BioRad; 1 cm×45 cm) which was equilibrated at room temperature with 0.2M Tris-base, pH 8.5 at a flow rate of 15 ml/hr and the eluant was monitored at 280 nm. The void volume of the run was collected, pooled, and loaded onto a QAE-Sephadex A-25 column (Pharmacia; 1 cm×10 cm) which was equilibrated at room temperature with 50 mM Tris-HCl, pH 7.0. This was done to remove any unlabeled peptides (which will adsorb to the positively charged resin; the positive charge of the labeled peptide allowed it to pass out of the column without further treatment). The eluant was monitored at 280 nm, and the first major peak was collected, pooled, and concentrated by lyophilization. The dried compound was resuspended in a minimal volume of PBF. The hCG peptide-Compound IV conjugate was stored at 4° C. until used.

EXAMPLE 64

Purification of Rabbit Anti-hCG Peptide by DEAE AFFI-Gel Blue Chromatography 4 ml of DEAE AFFI-Gel Blue (Bio-Rad) was poured into a chromatography column (1 cm×10 column size) and equilibrated at room temperature with 0.2M Tris-HCl containing 0.028M NaCl, pH 8.0, for 1 hr at a 40 ml/hr flow rate. The flow rate was slowed to 20 ml/hr and 1 ml of rabbit anti-hCG peptide (anti 109-145, Vernon Stevens, Ohio State University), which was predialyzed against the column buffer, was loaded onto the column. 1 ml fractions were collected and the eluant was volume peak was monitored collected, at 280 nm. The void volume peak was collected, pooled from several runs, and concentrated by placing the eluant in a 12K MWCO dialysis sack which was surrounded with polyethlyene glycol 6,000 (Sigma). The antibody was tested for immunoreactivity using standard ELISA techniques and for purity by HPLC, which resulted in one major peak, indicating a pure, active preparation.

EXAMPLE 65

Titration of hCG Peptide-Compound IV Conjugate Against Purified Rabbit Anti-hCG Peptide: Electrochemiluminescence Signal Modulation hCG peptide-Compound IV Conjugate was diluted in 0.1M phosphate buffer containing 0.1M citrate, pH 6.2. Aliquots of this mixture were placed in microfuge tubes. The previously purified anti-peptide antibody was diluted to various concentrations and added to the tubes, which were mixed on a vortex and incubated for 1 hr at room temperature. Just before reading electrochemiluminescence, an aliquot was transferred to a Berthold tube to which oxalic acid and Triton X-100 (Sigma) were added. The tubes were mixed on a vortex and read using sweep mode (+1.5 to +2.5V at 50 mV/sec of which 3 scans were done, taking the peak height of the second scan as the value) on a Berthold luminometer using an R-268 photomultiplier—tube with a double platinum mesh electrode. Between readings the electrode was cleaned electrochemically by first rinsing it with deionized water and then immersing it in 0.1M phosphate-citrate buffer, pH 6.1, containing 25 mM oxalate and 1% Trion X-100. The applied potential was switched, with three seconds at each potential, between +2.2V and −2.2V for 1 min and 50 sec and poised at +2.2V for 10 sec. The power was then shut off and the electrode removed from the cleaning solution and rinsed with deionized water and blotted dry with absorbent toweling.

The results showed a general trend in which the electrochemiluminescent signal was directly proportional to the concentration of antibody to the peptide. This is in contrast to other experiments in which the electrochemiluminescent signal drops as the electrochemiluminescent labelled analyte is contacted with antibody.

EXAMPLE 66

Electrochemiluminescence Signal Output: Stability Data of Ru (II)-Compound III Conjugate Ru(II)-Compound III conjugate was diluted to 300 nM in 0.1M phosphate-citrate buffer, pH 6.1, either with or without 1% normal human serum (NHS). One of each buffer type was incubated at 4°, 20°, 37° and 55° C. and sampled on incubation days 3, 4, and 5. The were equilibrated at room temperature and evaluated for their electrochemiluminescence signal output. 400 microliters of sample was mixed with 100 microliters of 125 mM oxalic acid-5% Triton X-100 in a tube and placed in a modified Berthold luminometer with a Hamamatsu R-268 photomultiplier tube and a double mesh platinum gauze electrode. The reading was made by sweeping the applied potential from +1.5V to +2.5V at 50 mV/second for 3 cycles and the height of the second cycle peak was recorded and converted into electrochemiluminescent counts. Between readings the electrode was cleaned electrochemically by rinsing with deionized water, immersing the electrode in 0.1M phosphate-citrate buffer containing 25 mM oxalate and 1% Triton X-100 and pulsing the potential from −2.2V to +−2.2V with a 3 sec pause at each potential for 1 min and 50 sec. The potential was poised at +2.2V for 10 sec and then removed. The electrode was removed from the cleaning solution, rinsed with deionized water and blotted dry with absorbent toweling. The results show that there was consistent signal in each buffer type over the course of the study. This indicates the stability of the reagent and its capability of generating an electrochemiluminescent signal.

EXAMPLE 67

Immunoreactivity Testing of Ru (II)-Compound III Conjugate: Stability Studies

The Ru(II)-Compound III conjugate was diluted and incubated under the conditions as described in Example 66. Samples were taken on days 3, 4, and 5 cooled to room temperature and tested for immunoreactivity by Particle Concentration Fluorescent Immunoassay (PCFIA) using a Pandex Screen Machine obtained from Pandex, Inc., Mundelein, Ill. The PCFIA was run in a competitive assay format. The latex particles (Pandex) were conjugated with theophylline-BSA. A constant amount of these particles were mixed with the Ru (II)-Compound III Conjugate test solution to final concentrations of anti-theophylline monoclonal antibody (ascites, Hyclone cat #E-3120M, lot #RD200) and a constant amount of goat anti-mouse IgG-PITC conjugate (Pandex, cat #33-020-1 lot # CO1). After incubation, the samples were processed and read on the Pandex Screen Machine. The results showed that there was no appreciable loss of activity even after 5 days incubation at 55° C.

EXAMPLE 68

Electrochemiluminescence of Various Ruthenium and Osmium Compounds

The electrochemistry of various osmium and ruthenium compounds was measured as 1 mM solutions in 10 ml of nitrogen-purged acetonitrile with 0.1 M tetrabutylammonium tetrafluoroborate as an electrolyte. The working electrode was a platinum disk electrode obtained from Bioanalytical Systems, Inc., West Lafayette, Ind. A platinum wire counter electrode and a 1.0 mm silver wire was used as a reference electrode. Measurements were made by scanning from −2.2V to +2.2V (vs SCE) at a scan rate of 100 mV/second. After each electrochemical measurement the potential difference between a Saturated Calomel Reference Electrode (SCE) and the silver wire was determined. Thus, the values reported are corrected to the potential versus SCE.

Electrochemiluminescent (ECL) measurements were made in 0.5 ml aqueous solutions containing 0.1M phosphatecitrate buffer (pH 4.2), 25 mM oxalic acid, and 1% Triton X-100. The electrode system used consisted of two platinum gauze (52 gauge) electrodes connected to a Radio Shack transistor socket (#276-548) by a 0.1 mm platinum wire. The electrodes were mounted on the outside of a 60 ml thick piece of cellulose acetate plastic. This plastic was machined so that a ¼ inch diameter hole allows solution to easily flow between the working and counter-reference electrodes. The electrodes were connected to the potentiostat so that one electrode functioned as a working electrode (which was closer to the photomultiplier tube) and one electrode functioned as the counter and reference electrode. Measurements were made by sweeping from 1.5V to 2.5V (bias potential) at a scan rate of 50 mV/second. The ECl measurements are reported as the signal to noise ratio, i.e., or signal to background ratio for a given concentration of compound. Background is defined as the luminescent counts observed with buffer and no ECl compounds added. Luminescent measurements were the peak light output observed during the first or second linear sweep.

Both electrochemiluminescent (ECL) and cyclic voltammetric measurements of each solution were performed with either a EG&G Model 273 potentiostat or a bipotentiostat from Ursar Scientific Instruments, Oxford, England. The photon flux of each ECL measurement was monitored with a Berthold Biolumat LB 9500 luminometer from Wilebad, West Germany, modified so that either a two or three electrode system could be placed in the 0.5 ml measuring solution. Both electrochemical and electrochemiluminescent measurements were recorded on a Kipp & Zonen Model BD 91 X, Y, Y' recorder from Delft, Holland.

Fluorescence measurements were made with 50 micromolar solutions of the desired compound in 3.0 ml of ECL solution, or when insoluble in ECL solution, in acetonitrile. Measurements were made on a Perkin-Elmer LS-5 Fluorescence Spectrophotometer. Prescans of the solutions' excitation and emission spectra were performed before the excitation and emission spectra were recorded so that the emission spectrum could be measured while irradiating at the maximum excitation wavelength and conversely, the excitation spectrum could be recorded while monitoring the maximum emission wavelength.

| Compound | $E_{OX_{vs}}$ | $SCE^{Ered}$ | Fluorescence Emission Max | E CL (S/N)[1] & Conc. |
|---|---|---|---|---|
| a) Ru(bipy)$_3$ | 1.07 V | −1.52 V | 625 nm | 1 × 10$^{-9}$ M (2.5) |
| b) Ru(4,4'-CO$_2$-bipy)$_3$ | 1.19 V | N. D. | 628 nm | 2 × 10$^{-9}$ M (4.05) |
| c) Ru(4,4'CO$_2$-Et-bipy)$_3$ | 1.54 V | −0.89 V | 636 nm | 1 × 10$^{-10}$ M (2.01) |
| d) Ru(bipy)$_2$ (C-8-theophylline C-4-bipy) | 1.17 V | N. D. | 624 nm | 1 × 10$^{-9}$ M (.97) |
| e) Os (bipy)$_2$ (CO)(py) | 1.82 V | −0.99 V | 585 nm | 1 × 10$^{-8}$ M |
| f) Os (DPPene) (bpy) (bpyoxal) | 1.60 V | N. D. | 630 nm | 6 × 10$^{-8}$ M (10.8) |

[1](S/N) is the signal to noise ratio, where the signal is defined as the ECL output (luminescent counts) of a compound at a given concentration, and noise is the luminescent counts of the buffer in which the compound was dissolved.

Unlike the ECL of the other compounds which were measured at pH 4.2, compound C) also displays significant ECL at the physiological pH of 7.0.

a) Tris(2,2'-bipyridine)ruthenium$^{2+}$
b) Tris(4,4'-carboxylate-2,2'-bipyridine ruthenium$^{2+}$
c) Tris(4,4'-carboethoxy-2,2'-bipyridine)ruthenium$^{2+}$
d) bis(2,2'-bipyridine)[theophylline-8-butyric-4-(4-methyl-2,2'-bipyridine)-4'-yl)-butyl]amide]ruthenium (II) dichloride
e) [bis-(2,2'-bipyridine){monocarbonyl}pyridyl]osmium (II) dihexafluorophosphate
f) (2,2'-bipyridine[cis-bis(1,2-diphenyphosphine)ethylene)] {2[3-(4-methyl-2,2'-bipuridine-4'-yl)propyl]-1,3-dioxolane}osmium (II) dichloride

EXAMPLE 69

Preparation of bis(2,2'-bipyridine)([4-(4'-methyl-2, 2'-bipyridine)butyl amine]ruthenium (II) diperchlorate 1.29 g (2.48 mmol) of bis-(2,2'-bipyridine)ruthenium (II) dichloride dehydrate (Strem) and 0.719 g (2.98 mmol) of 4-(4-[1-aminobutyl)]4'-methyl-2,2'-bipyridine (described in Example 32) were suspended in 50 ml of 50/50 ethanol/H₂O and refluxed under argon for 3 hr. The reaction solution was concentrated and subjected to chromatographic separation on Sephadex C-25, eluting first with distilled water and then with 0.25 M NaCl. Final elution was performed with 0.4 M NaCl. The fractions containing the product were concentrated to about 100 ml and perchloric acid was added until the solution became cloudy. Upon refrigeration overnight, red orange crystals of the product (1.215 g) were obtained. Elemental analysis confirmed the structure to be

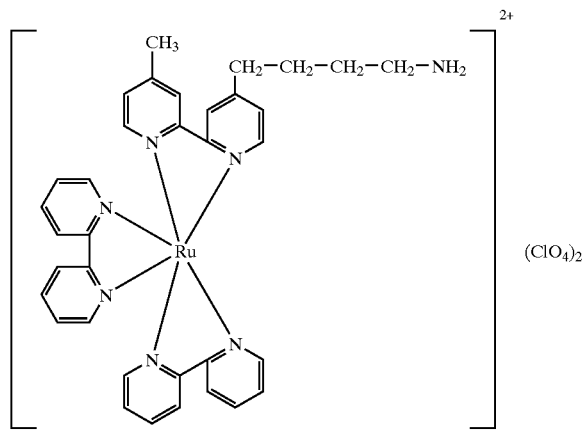

EXAMPLE 70

Preparation of theophylline-8-(3,3dimethyl)butyric acid 5,6-diamino, $N^1,N^3$-dimethyl uracil hydrate (10 g, 0.059 mol) and 3,3-dimethylglutaric acid anhydride (12.6 g, 8.85×10⁻² mol) were dissolved in 100 ml N,N-dimethyl aniline and brought to reflux using a Dean-Stark trap. The contents of the reaction became solubilized after heating and turned orange red. After 4 hrs of reflux, 1 ml of water was collected in the trap, indicating the reaction had completed. The reaction was allowed to cool to room temperature, at which time the entire mass solidified. The solid was filtered on a fritted funnel and washed until it became pale yellow in color. After two crystallizations from DMF, pure white crystals of the intermediate lactam (melting point 283.1–284.9° C.) were obtained. The lactam was boiled in water for 8 hrs. Upon cooling, the solution yielded pure white crystals (melting point 218–220° C.). Proton NMR and elemental analysis were consistent with the following structure

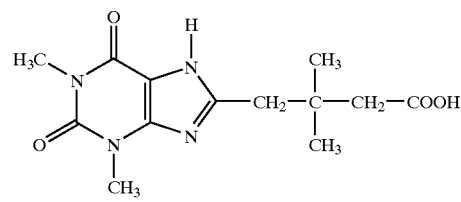

EXAMPLE 71

Preparation of bis-(2,2'bipyridine)[theophylline-8-(3,3-dimethylbutyric-{4-(4methyl-2,2'-bipyridine-4'-yl)-butyl}amide]ruthenium (II) diperchlorate 100 mg (0.34 mmol) of theophylline-8-(3,3-dimethyl)butyric acid and 0.325 g (0.34 mmol) of bis(2,2'-bipyridine)[4-(4'-methyl-2,2'-bipyridine)butyl amine ruthenium (II) diperchlorate were dissolved in 10 ml of dry pyridine along with 0.351 g (1.7 mmol) of dicyclohexylcarbodiimide. The reaction was allowed to stir for 2 days. Copious dicyclohexylurea precipitate was removed by filtration and the pyridine solution was concentrated under vacuum. The residue was dissolved in methanol and chromatographed on Sephadex LH-20. On concentration of the desired fractions the product was precipitated from ether to give an orange precipitate. Elemental analysis and proton NMR were consistent with the structure

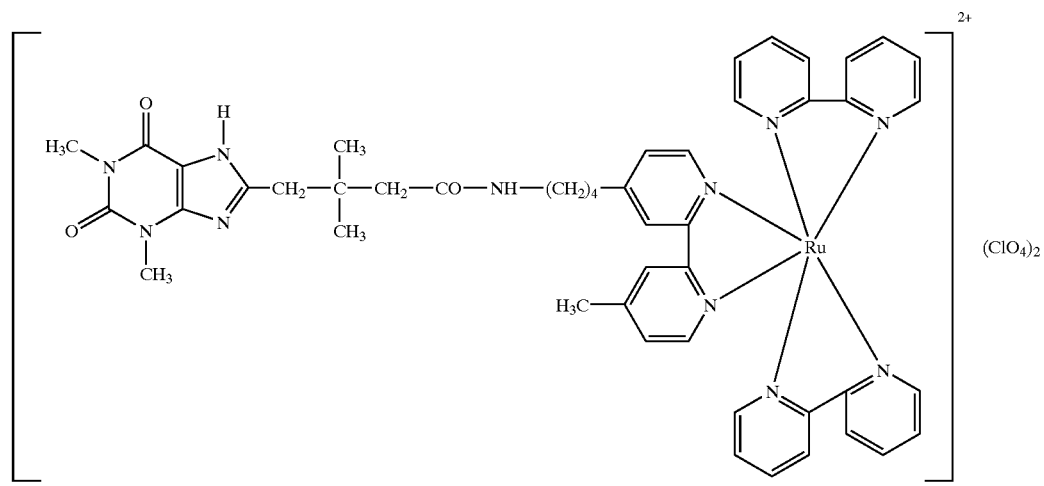

EXAMPLE 72

Preparation of theophylline-8-propyl(4-methyl-2,2'-bipyridine-4'-butyl)carboxamide 61.8 mg (1.55×10⁻⁴ mol) of 8-(gamma-aminopropyl) theophylline phthalic acid hydrazide salt were dissolved in 1 ml H₂O and acidified with HCl. The precipitated phthalic acid hydrazide was filtered off and the aqueous filtrate was evaporated and dried under vacuum to give 34.5 mg ($1.31 \times 10^{-4}$ mol) of theophylline-8-propylamine hydrochloride. This material was dissolved in 5 ml dry pyridine and 36.9 mg ($1.44 \times 10^{-4}$ mol) of 4-(4-methyl-2,2'-bipyridine-4'-yl) butyric acid and 26.4 mg ($2.62 \times 10^{-4}$ mol) of triethylamine were added to it. Finally, 29.7 mg ($1.44 \times 10^{-4}$ mol) of dicyclohexylcarbodiimide were added to the solution. The resulting cloudy solution was allowed to stir overnight. The precipitated salt and dicyclohexylurea were filtered off and the solution was stripped to dryness to give a white solid which was chromatographed on alumina using 5% methanol in dichloromethane as the eluant to yield 44.2 mg (71%) of the product as a white powder (melting point 215°–216.5° C.). Proton NMR and elemental analysis were consistent with the following structure

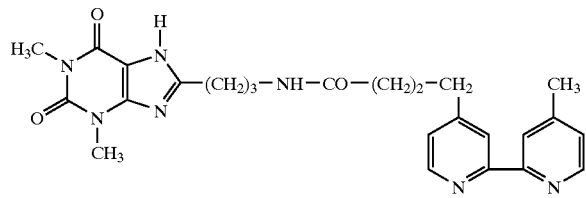

EXAMPLE 73

Preparation of bis-(2,2'-bipyridine)[theophylline-8-propyl(4-methyl-2,2'-bipyridine-4'-butyl) carboxamide]ruthenium (II) dichloride 100 mg ($2.06 \times 10^{-4}$ mol) of bis(2,2'-bipyridine)ruthenium dichloride (Strem) and 108 mg ($2.27 \times 10^{-4}$ mol) of theophylline-8-propyl(4-methyl-2,2'-bipyridine-4'-butyl) carboxamide were added to 50 ml of 50% ethanol which had been degassed with argon. The solution was heated at reflux. The resulting cherry red solution was concentrated under high vacuum at room temperature. The residue was chromatographed on Sephadex LH-20 (75 cm×19 mm I. D.) using methanol as eluent. The product band was isolated, evaporated and precipitated into anhydrous ether. The yield of the product was 156 mg (75%). Elemental analysis indicated the presence of 4 mols of methanol in the product.

Analysis: Calculated; C, 54.09; H, 5.65; N, 14.16; O, 10.29; Cl, 6.52; Found: C, 53.30; H, 5.22; N, 14.56; O, 10.63 and Cl, 6.95.

EXAMPLE 74

Preparation of bis(2,2'-bipyridine)(1-bromo-4-(4'-methyl-2,2'-bipyridine-4-yl)butane]ruthenium (II) diperchlorate 0.29 g of the ligand 1-bromo-4-(4'-methyl-2,2'-bipyridine-4-yl)butane prepared in Example 3 and 0.32 g of bis(2,2'-bipyridine)ruthenium (II) dichloride were transferred to a flask in 60 ml of 1:1 v/v ethanol/water mixture. The solution was degassed with nitrogen for 15 min. The reaction was heated at reflux under nitrogen for 3½ hrs. An aqueous saturated solution of $NaClO_4$ was added to the cooled red solution. Solvents were removed under vacuum and the deep red residue was chromatographed on an alumina column (20 cm×2.5 cm, Merck, neutral activity 3) using acetonitrile/toluene 1:1 v/v as the eluant. The product eluted as a dark red band (band #2) on the column. The desired fraction was concentrated, redissolved in approximately 10 ml volume of dichloromethane, precipitated from anhydrous ethyl ether and finally dried under vacuum to yield 320 mg (53%) of the product. The structure of the product was confirmed by elemental analysis and spectral characteristics and is shown below.

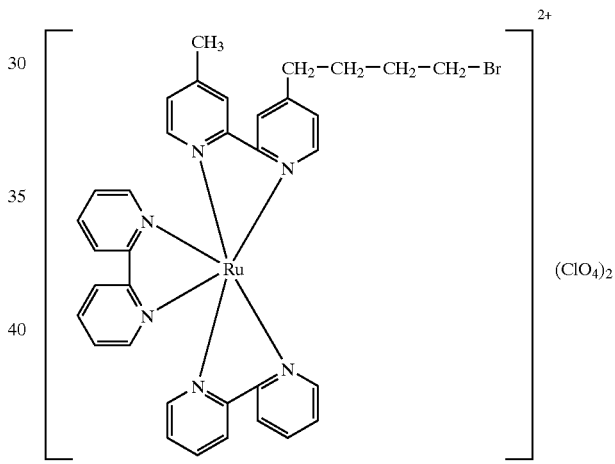

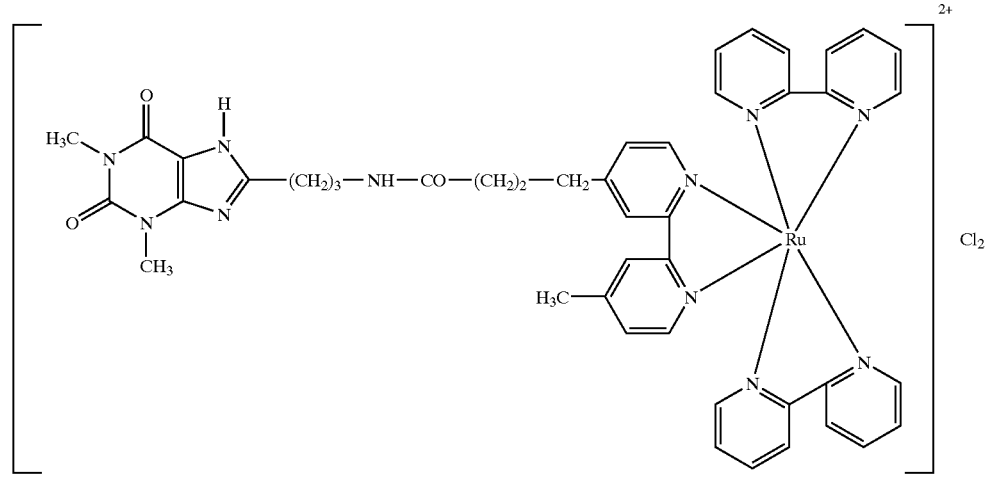

EXAMPLE 75

Preparation of bis(2,2'-bipyridine)[theophylline-9-[4-(4-methyl-2,2'bipyridine-4'-yl)butane]ruthenium (II) diperchlorate The silver salt of theophylline was prepared by mixing together an ammonia solution of theophylline (2.168 g in 25 ml conc. $NH_4OH$ and 75 ml water) and an ammonia solution of silver nitrate (2.006 g in 10 ml conc. $NH_4OH$ and 30 ml $H_2O$), the reaction being carried out in the dark. Shortly after mixing the two solutions, a white product appeared. Once the precipitation of the product was completed, the precipitate was collected by filtration on a 60 ml medium glass frit. The precipitate was washed with dilute ammonia and dried under vacuum. The structure of the silver salt of theophylline was supported by elemental analysis.

41 mg of the silver salt of theophylline and 122 mg of bis(2,2'-bipyridine)[1-bromo-4-(4'-methyl-2,2'-bipyridine-4-yl)butane]ruthenium (II) diperchlorate were dissolved in 15 ml of anhydrous dimethylformamide (DMF), the reaction being carried out in the dark. The resulting red solution was degassed with argon and heated at reflux for 24 hrs and then cooled to room temperature under argon. Cooling of the solution was continued down to ice temperature and then the black silver metal suspension was filtered off and washed with 5 ml acetone. The red filtrate was treated with 0.2 g of lithium perchlorate and after dissolution of $LiClO_4$, the solution was evaporated under vacuum and the red residue was dried overnight in the dark under vacuum. The sample was redissolved in 3–5 ml of methanol and 0.25 g of anhydrous $LiClO_4$ was added and dissolved. The resulting solution was chromatographed on a Sephadex LH-20 Column (75 cm×19 cm i.d.) using methanol as the eluant. The major product eluted as fraction #2 (dark red band). Fraction #2 was concentrated, redissolved in methanol and precipitated into ethyl ether. The product was dried under vacuum to yield 80 mg (50% yield) of material, the structure of which was confirmed by elemental analysis, infra red and emission spectra.

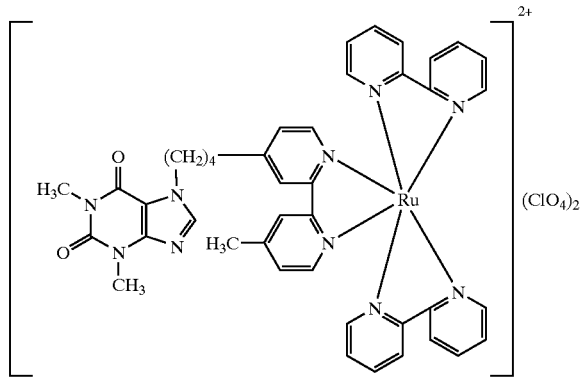

References

1. Weber, S. G., et al., Photoelectroanalytical Chemistry: Possible Interference in Serum and Selective Detection of Tris(2,2'-bypyridine)ruthenium(II) in the Presence of Interferents, Clinical Chemistry, 29, 1665–1672 (1983).
2. Rubinstein, I. and Bard, A. J., Electrogenerated Chemiluminescence. 37. Aqueous ECL Systems Based On Ru (2,2-bypyridine)$_3^{2+}$ and Oxalate or Organic Acids, J. Am. Chem. Soc., 103, 512–516(1981).
3. White, H. S. and Bard, A. J., Electrogenerated Chemiluminescence. 41. Electrogenerated Chemiluminescence and Chemiluminescence of the Ru(2,2'-bpy)$_3^{+2}$-$S_2O_8^{-2}$ System in Acetonitrile-Water Solutions, J. Am. Chem. Soc., 104, 6891 (1982).
4. Curtis, et al., Chemiluminescence; A New Method for Detecting Fluorescent Compounds Separated By Thin Layer Chromatography, J. Chromatography, 134, 343–350 (1977).
5. Sprintschnik, G., et al., Preparation and Photochemical Reactivity of Surfactant Ruthenium (II) Complexes in Monolayer Assemblies and at Water—Solid Interface, J. Am Chem. Soc., 99, 4947–4954 (1977).
6. Minnich, S. A., et al., Enzyme Immunoassay for Detection of *Salmonellae* in Foods, Appl. and Environ. Micro., 43, 1124–1127 (1982).
7. Thomason, B. M., Current Status of Immunofluorescent Methodology for *Salmonellae*, J. Food Prot., 44, 381–384 (1981).
8. Mattingly, J. A., An Enzyme Immunoassay for the Detection of All *Salmonella* Using a Combination of a Myeloma Protein and a Hybridoma Antibody, J. Immunol. Meth., 73, 147–156 (1984).
9. Thompson, N. E. et al., Detection of *Staphylococcal* enterotoxins by enzyme-linked immunosorbent assays and radio-immunoassays: Comparison of monoclonal and polyclonal antibody systems, Appl. and Environ. Micro., submitted publication.
10. American Public Health Association, Standard methods for the examination of water and wastewater. 15th ed. American Public Health Association, Inc., New York (1980).
11. American Public Health Association, Compendium of methods for the microbiological examination of foods. American Public Health Association, Washington, D.C. (1976).
12. Clark, H. F., Geldreich, E. E., Lester, H. L., and Kabler, P. W. The membrane filter in sanitary microbiology, Public Health Rep. 66:951–957 (1951).
13. Feng, P., and Hartman, P. A., Fluorogenic assays for immediate confirmation of *Escherichia coli*., Appl. Environ. Microbiol. 43:1320–1329 (1982).
14. Geldreich, E. E., Standard method Revisions (16th edition) for Conventional coliform Procedures. In: New developments in drinking water microbiology workshop, 85th Annual Meeting of the American Society for Microbiology (1985).
15. Hussong, D., Colwell, R. R., and Weiner R. M., Rate of occurrence of false-positive results from total coliforms most-probable-number analysis of shellfish and estuaries. Appl. Environ. Microbiol. 40:981–983 (1980).
16. Hussong, D., Demare, J. M., Weiner, R. M., and Colwell, R. R., Bacteria associated with false-positive most-probable-number coliform test results for shellfish and estuaries, Appl./Environ. Microbiol 41:35–45 (1981).
17. Lin, S., Evaluation of coliform tests for chlorinated secondary effluents, J. Water Pollut. Control Fed. 45:498–506 (1973).

18. Mckee, J. E., McLaughlin, R. T. and Lesgourgues, P., Application of molecular filter techniques to the bacterial assay of sewage III. Effects of physical and chemical disinfection, Sewage Ind. Waste 30:245–252 (1958).
19. Mead, J. A. R., Smith, J. N., and Williams, R. T., The biosynthesis of the glucuronides of umbelliferone and 4-methylumbelliferone and their use in fluorimetric determination of beta-glucuronidase, Biochem. J. 61:569–574 (1954).
20. Olson, B. H., Enhanced accuracy of coliform testing in seawater by modification of the most-probable-number method. Apl. Environ. Microbiol, 36:438–444 (1978).
21. Presnell, M. W., Evaluation of membrane filter methods for enumerating coliforms and fecal coliforms in estuarine waters, Proc. National Shellfish Sanitation Workshop. 1974:127–131 (1974).
22. Presswood, W. G. and Strong, D. K., Modification of mFC medium by eliminating rosolic acid, Appl. Environ. Microbiol. 36:90–94 (1978).
23. Warr, G. W. and Marchalonis, J. J., Purification of Antibodies. In: *Antibody, as a Tool*, J. Wiley and Sons, NY, pp. 59–96. (1982)
24. Maniatis, T., Fritsch, E. F. and Sambrook, J., Molecular Cloning: A Laboratory Manual, p. 150–160, Cold Spring Harbor Press, Cold Spring Harbor, N.Y. (1982).

repeatedly emit electrochemiluminescence upon exposure to an amount of electrochemical energy from a suitable source;

(b) exposing the resulting sample to an amount of electrochemical energy from a suitable source effective to induce the reagent to repeatedly emit electrochemiluminescence; and (c) detecting emitted luminescence to determine whether the enzyme is present in or absent from the sample;

wherein cleavage of the polymer by the enzyme increases the electrochemiluminescence and wherein the metal-containing organic compound conjugated to the polymer comprises ruthenium.

2. A method of detecting the presence or absence of an enzyme in a sample, which comprises:

(a) contacting said sample with a reagent comprising a metal-containing organic compound conjugated to a polymer, wherein said polymer is a substrate for and cleaved by said enzyme and said metal-containing organic compound is capable of being induced to repeatedly emit electrochemiluminescence upon exposure to an amount of electrochemical energy from a suitable source;

(b) exposing the resulting sample to an amount of electrochemical energy from suitable source effective to induce the reagent to repeatedly emit electrochemiluminescence; and

What is claimed is:

1. A method of detecting the presence or absence of an enzyme in a sample, which comprises:

(a) contacting said sample with a reagent comprising a metal-containing organic compound conjugated to a polymer, wherein said polymer is a substrate for and cleaved by said enzyme and said metal-containing organic compound is capable of being induced to (c) detecting emitted luminescence to determine whether the enzyme is present in or from the sample;

wherein cleavage of the polymer by the enzyme increases the electrocheminescence and wherein the metal-containing organic compound conjugated to the polymer comprises osmium.

* * * * *

UNITED STATES PATENT AND TRADEMARK OFFICE
CERTIFICATE OF CORRECTION

PATENT NO. : 6,916,606 B2
DATED : July 12, 2005
INVENTOR(S) : Massey et al.

It is certified that error appears in the above-identified patent and that said Letters Patent is hereby corrected as shown below:

Title page,
Item [75], Inventors, "Gaithersburg," should read -- Rockville, --.

Column 86,
Line 25, "from suitable" should read -- from a suitable --.
Line 61, "or from" should read -- or absent from --.
Line 63, "electrocheminescence" should read -- electrochemiluminescence --.

Signed and Sealed this

Fourth Day of October, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 38
<212> TYPE: DNA
<213> ORGANISM: Artificial
<220> FEATURE:
<223> OTHER INFORMATION: The sequence is a custom synthesized 38-mer.
<220> FEATURE:
<221> NAME/KEY: Modification
<222> LOCATION: (38)..(38)
<223> OTHER INFORMATION: The last T is modified at carbon 5 with
    -CH=CH-CO-NH-(CH2)7-NH2

<400> SEQUENCE: 1
tcaccaataa accgcaaaca ccatcccgtc ctgccagt          38